(12) United States Patent
Behrendorff et al.

(10) Patent No.: US 10,174,303 B2
(45) Date of Patent: Jan. 8, 2019

(54) GENETICALLY ENGINEERED MICROORGANISMS FOR THE PRODUCTION OF CHORISMATE-DERIVED PRODUCTS

(71) Applicant: LanzaTech New Zealand Limited, Skokie, IL (US)

(72) Inventors: James Bruce Yarnton Haycock Behrendorff, Skokie, IL (US); Michael Koepke, Skokie, IL (US); Loan Phuong Tran, Skokie, IL (US); Wyatt Eric Allen, Skokie, IL (US)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 0 days.

(21) Appl. No.: 15/166,224

(22) Filed: May 26, 2016

(65) Prior Publication Data

US 2016/0348087 A1   Dec. 1, 2016

Related U.S. Application Data

(60) Provisional application No. 62/167,101, filed on May 27, 2015.

(51) Int. Cl.
*C12N 1/20* (2006.01)
*C12P 1/04* (2006.01)
(Continued)

(52) U.S. Cl.
CPC ............... *C12N 9/88* (2013.01); *C12N 1/20* (2013.01); *C12N 15/52* (2013.01); *C12P 1/04* (2013.01); *C12P 7/62* (2013.01); *C12Y 401/0304* (2013.01); *C12Y 402/99021* (2013.01); *C12Y 504/04002* (2013.01); *C12Y 504/99005* (2013.01)

(58) Field of Classification Search
None
See application file for complete search history.

(56) References Cited

U.S. PATENT DOCUMENTS 4,681,852 A * 7/1987 Tribe ................ C12N 15/52
435/108
2010/0210017 A1 8/2010 Gill et al.
(Continued)

FOREIGN PATENT DOCUMENTS

CA  2890922 A1  5/2014
WO  2008028055 A2  3/2008

OTHER PUBLICATIONS

Abrini, Arch Microbiol, 161: 345-351, 1994.
(Continued)

*Primary Examiner* — Richard C Ekstrom
(74) *Attorney, Agent, or Firm* — Andrea E Schoen

(57) ABSTRACT

The invention provides genetically engineered microorganisms and methods for producing chorismate-derived products, such as para-hydroxybenzoic acid, salicylate, 2-aminobenzoate, 2,3-dihydroxybenzoate, and 4-hydroxycyclohexane carboxylic acid. Typically, the microorganism comprises at least one of (a) an exogenous chorismate pyruvate lyase, (b) an exogenous isochorismate synthase, (c) an exogenous isochorismate pyruvate lyase, and (d) a prephenate synthase comprising a disruptive mutation.

24 Claims, 32 Drawing Sheets

Specification includes a Sequence Listing.

(51) Int. Cl.
    *C12N 9/88*     (2006.01)
    *C12P 7/62*     (2006.01)
    *C12N 15/52*     (2006.01)

(56) References Cited

U.S. PATENT DOCUMENTS

| | | | |
|---|---|---|---|
| 2010/0298599 A1* | 11/2010 | Rangachari | C12P 7/42 562/508 |
| 2011/0256600 A1 | 10/2011 | Simpson et al. | |
| 2013/0217096 A1 | 8/2013 | Heijstra et al. | |
| 2014/0212976 A1* | 7/2014 | Mueller | C12N 9/0036 435/440 |
| 2014/0370557 A1 | 12/2014 | Yan et al. | |
| 2015/0004662 A1 | 1/2015 | Osterhout | |
| 2016/0273005 A1* | 9/2016 | Magnus | C12N 9/88 |

OTHER PUBLICATIONS

Averesch, Engineer Comm, 1: 19-28, 2014.
Bentley, Crit Rev Biochem Mol Biol, 25.5: 307-384, 1990.
Bertsch, Biotechnol Biofuels, 8: 210, 2015.
Dosselaere, Crit Rev Microbiol, 27: 75-131, 2001.
Drake, Acetogenic Prokaryotes, in: The Prokaryotes, 3rd edition, p. 354, New York, NY, 2006.
Dürre, Handbook on Clostridia, CRC Press, pp. 813-814, 2005.
Heap, J Microbiol Meth, 80: 49-55, 2010.
Hu, J Basic Microbiol, 43: 399-406, 2003.
Jones, Microbiol Rev, 50: 484-524, 1986.
Kronick, Clinica Chimica Acta, 132: 205-208, 1983.
Ragsdale, Biochim Biophys Acta, 1784: 1873-1898, 2008.
Tanner, Int J System Bacteriol, 43: 232-236, 1993.
Wang, J Bacteriol, 195: 4373-4386, 2013.

\* cited by examiner

| Microorganism | Genbank Accession | Microorganism | Genbank Accession |
|---|---|---|---|
| Proteobacteria | WP_001326644.1 | Bartonella clarridgeiae | WP_013544696.1 |
| Escherichia coli | WP_032343343.1 | Providencia alcalifaciens | WP_036955412.1 |
| Enterobacteriaceae | WP_001295693.1 | Providencia rustigianii | WP_006816067.1 |
| Shigella flexneri | WP_005071384.1 | Bartonella rattimassiliensis | WP_007347862.1 |
| Shigella sp. SF-2015 | WP_005002785.1 | Edwardsiella anguillarum | WP_034163029.1 |
| Escherichia | WP_000019214.1 | Edwardsiella | WP_045427790.1 |
| Shigella sonnei | WP_052990089.1 | Phaseolibacter flectens | WP_028684858.1 |
| Escherichia albertii | WP_000019228.1 | Providencia stuartii | WP_004925912.1 |
| Citrobacter youngae | WP_006688307.1 | Edwardsiella ictaluri | WP_015869674.1 |
| Citrobacter freundii | WP_054527959.1 | Edwardsiella piscicida | WP_015460726.1 |
| Citrobacter | WP_048213934.1 | Sodalis praecaptivus | WP_051440195.1 |
| Citrobacter pasteurii | WP_005132668.1 | Sodalis glossinidius | WP_011411956.1 |
| Citrobacter freundii complex | WP_032942095.1 | Edwardsiella tarda | WP_035597793.1 |
| Enterobacter cloacae | WP_063411731.1 | Providencia sneebia | WP_008916956.1 |
| Citrobacter amalonaticus | WP_061075585.1 | Providencia burhodogranariea | WP_008913736.1 |
| Gammaproteobacteria | WP_042999031.1 | Edwardsiella hoshinae | WP_024524687.1 |
| Enterobacter | WP_014882105.1 | Candidatus Sodalis pierantonius | WP_025246620.1 |
| Enterobacter cloacae complex | WP_045355219.1 | Photobacterium aquae | WP_047877737.1 |
| Enterobacter sp. BIDMC 29 | WP_041911565.1 | Photobacterium marinum | WP_007469524.1 |
| Enterobacter sp. 35730 | WP_045268808.1 | Photobacterium sanguinicancri | WP_062688249.1 |
| Enterobacter sp. T1-1 | WP_029882656.1 | Photobacterium swingsii | WP_048898785.1 |
| Enterobacter cloacae complex 'Hoffmann cluster IV' | WP_008500083.1 | Photobacterium damselae | WP_044173922.1 |
| Enterobacter asburiae | WP_023617246.1 | Photobacterium sanctipauli | WP_036818650.1 |
| Enterobacter sp. BIDMC92 | WP_047957525.1 | Agarivorans albus | WP_016399749.1 |
| Enterobacter sp. 638 | WP_011915505.1 | Photobacterium profundum | WP_006233275.1 |
| Citrobacter farmeri | WP_042321063.1 | Vibrio maritimus | WP_042478790.1 |
| Citrobacter koseri | WP_012134646.1 | Vibrio metoecus | WP_055052109.1 |
| Enterobacter hormaechei | WP_023299087.1 | Grimontia celer | WP_062666858.1 |
| Escherichia fergusonii | WP_000019211.1 | Vibrio | WP_001072883.1 |
| Enterobacter cancerogenus | WP_042321179.1 | Agarivorans gilvus | WP_055733842.1 |
| Enterobacter sp. GN02454 | WP_047742368.1 | Vibrio alginolyticus | WP_053311436.1 |
| Salmonella enterica | WP_000019223.1 | Grimontia indica | WP_002535407.1 |
| Lelliottia amnigena | WP_059179835.1 | Photobacterium ganghwense | WP_047887262.1 |
| Enterobacter sp. Bisph1 | WP_039055748.1 | Grimontia sp. AD028 | WP_046303386.1 |
| Salmonella bongori | WP_020845807.1 | Vibrio neptunius | WP_045975676.1 |

Fig. 13

| Microorganism | Genbank Accession | Microorganism | Genbank Accession |
|---|---|---|---|
| Enterobacter sp. FY-07 | WP_061498857.1 | Vibrio coralliilyticus | WP_043006692.1 |
| Escherichia vulneris | WP_042388891.1 | Photobacterium aphoticum | WP_047873744.1 |
| Yokenella regensburgei | WP_040902665.1 | Photobacterium leiognathi | WP_053987423.1 |
| Trabulsiella odontotermitis | WP_054179777.1 | Plesiomonas | WP_010862816.1 |
| Trabulsiella guamensis | WP_038158396.1 | Vibrio xuii | WP_053441696.1 |
| Enterobacter sp. MT20 | WP_061706855.1 | Vibrio sp. VPAP30 | WP_049845305.1 |
| Kosakonia radicincitans | WP_043955711.1 | Vibrio tubiashii | WP_038197373.1 |
| Kluyvera intermedia | WP_047372194.1 | Salinivibrio socompensis | WP_025673764.1 |
| Enterobacter sp. Bisph2 | WP_039077918.1 | Grimontia marina | WP_062709804.1 |
| Klebsiella oxytoca | WP_004109561.1 | Vibrio galatheae | WP_045956983.1 |
| Enterobacter xiangfangensis | WP_058715018.1 | Grimontia hollisae | WP_005501667.1 |
| Leclercia adecarboxylata | WP_039031929.1 | Photobacterium sp. SKA34 | WP_006647642.1 |
| Enterobacter aerogenes | WP_045362420.1 | Vibrio cholerae | WP_032480537.1 |
| Klebsiella | WP_014227537.1 | Vibrio caribbeanicus | WP_009602602.1 |
| Enterobacter massiliensis | WP_044180994.1 | Vibrionales bacterium SWAT-3 | WP_008224249.1 |
| Citrobacter rodentium | WP_012907701.1 | Enterovibrio calviensis | WP_017016798.1 |
| Raoultella terrigena | WP_045853463.1 | Vibrio bivalvicida | WP_054963396.1 |
| Klebsiella sp. OBRC7 | WP_009654674.1 | Vibrio orientalis | WP_004409565.1 |
| Klebsiella sp. RIT-PI-d | WP_049838501.1 | Vibrio sp. HI00D65 | WP_063524665.1 |
| Raoultella ornithinolytica | WP_041143590.1 | Vibrio ordalii | WP_038198194.1 |
| Klebsiella pneumoniae | WP_023342419.1 | Vibrio splendidus | WP_032554291.1 |
| Klebsiella sp. 10982 | WP_025713803.1 | Vibrio nigripulchritudo | WP_045967092.1 |
| Enterobacteriaceae bacterium strain FGI 57 | WP_015966334.1 | Photobacterium phosphoreum | WP_045031601.1 |
| Pluralibacter gergoviae | WP_048284191.1 | Salinivibrio sp. KP-1 | WP_046074636.1 |
| Kluyvera cryocrescens | WP_061283371.1 | Photobacterium gaetbulicola | WP_044622288.1 |
| Franconibacter helveticus | WP_024553577.1 | Photobacterium | WP_045083799.1 |
| Kluyvera ascorbata | WP_035896877.1 | Enterovibrio norvegicus | WP_016961855.1 |
| Franconibacter pulveris | WP_029593165.1 | Photobacterium angustum | WP_005372020.1 |
| Shimwellia blattae | WP_002445222.1 | Vibrio brasiliensis | WP_040895525.1 |
| Enterobacteriaceae bacterium LSJC7 | WP_017373629.1 | Aliivibrio fischeri | WP_012534390.1 |
| Cronobacter | WP_007796820.1 | Vibrio pacinii | WP_038175692.1 |
| Erwinia sp. SCU-B244 | WP_058912420.1 | Vibrio litoralis | WP_051241116.1 |
| Cronobacter sakazakii | WP_054624115.1 | Vibrio sp. HENC-03 | WP_009705152.1 |
| Cronobacter turicensis | WP_007764634.1 | Vibrio genomosp. F6 | WP_017051810.1 |
| Cronobacter malonaticus | WP_032994815.1 | Photobacterium aquimaris | WP_060997736.1 |
| Cronobacter muytjensii | WP_038867328.1 | Vibrio parahaemolyticus | WP_024699858.1 |
| Enterobacter sp. Ag1 | WP_008455844.1 | Vibrio harveyi | WP_033007672.1 |
| Cronobacter condimenti | WP_007667577.1 | Vibrio fortis | WP_032553387.1 |

Fig. 13 cont'd

| Microorganism | Genbank Accession | Microorganism | Genbank Accession |
|---|---|---|---|
| Cronobacter universalis | WP_007702330.1 | Vibrio campbellii | WP_051118327.1 |
| Cedecea neteri | WP_039299465.1 | Vibrio sp. CAIM 1540 | WP_047049487.1 |
| Cronobacter dublinensis | WP_007752848.1 | Photobacterium iliopiscarium | WP_045035868.1 |
| Klebsiella michiganensis | WP_045780974.1 | Moritella dasanensis | WP_017222441.1 |
| Buttiauxella agrestis | WP_034456982.1 | Vibrio harveyi group | WP_045372302.1 |
| Siccibacter colletis | WP_031521381.1 | Psychromonas arctica | WP_028869261.1 |
| Cedecea davisae | WP_016517422.1 | Vibrio rotiferianus | WP_029560889.1 |
| Mangrovibacter sp. MFB070 | WP_036102985.1 | Bermanella marisrubri | WP_050758020.1 |
| Enterobacter ludwigii | WP_061718382.1 | Vibrio nereis | WP_053396837.1 |
| Pantoea sp. RIT-PI-b | WP_049851273.1 | Vibrio sp. OY15 | WP_033907265.1 |
| Pantoea sp. GM01 | WP_009128583.1 | Aliivibrio wodanis | WP_060993987.1 |
| Pantoea sp. 3.5.1 | WP_031375526.1 | Vibrio renipiscarius | WP_040988992.1 |
| Pantoea sp. YR343 | WP_008109935.1 | Vibrio sp. AND4 | WP_043991786.1 |
| Erwinia billingiae | WP_013200342.1 | Vibrio shilonii | WP_050798660.1 |
| Pantoea sp. AS-PWVM4 | WP_021184075.1 | Vibrio ichthyoenteri | WP_006713584.1 |
| Pantoea | WP_038643645.1 | Vibrio azureus | WP_033004368.1 |
| Pantoea sp. BL1 | WP_045832390.1 | Vibrio sp. 3062 | WP_063605216.1 |
| Erwinia typographi | WP_034898291.1 | Vibrio diazotrophicus | WP_042489735.1 |
| Erwinia | WP_014539619.1 | Vibrio crassostreae | WP_048662880.1 |
| Erwinia iniecta | WP_052902020.1 | Vibrio sp. MED222 | WP_009848243.1 |
| Pantoea sp. PSNIH2 | WP_038629825.1 | Vibrio tasmaniensis | WP_032500146.1 |
| Erwinia pirifloringrans | WP_023656527.1 | Vibrio hyugaensis | WP_045466146.1 |
| Pantoea agglomerans | WP_033780412.1 | Moritella viscosa | WP_045112351.1 |
| Erwinia toletana | WP_017801681.1 | Vibrio sp. J2-17 | WP_050654326.1 |
| Erwinia mallotivora | WP_034935024.1 | Vibrio navarrensis | WP_039422096.1 |
| Pantoea sp. IMH | WP_024966000.1 | Psychromonas ingrahamii | WP_011771703.1 |
| Erwinia amylovora | WP_004160504.1 | Idiomarina xiamenensis | WP_008489429.1 |
| Type-F symbiont of Plautia stali | WP_058956993.1 | Vibrio sagamiensis | WP_039980960.1 |
| Pantoea sp. Sc1 | WP_009092618.1 | Vibrio owensii | WP_042980126.1 |
| Pantoea anthophila | WP_046101010.1 | Vibrio sp. J2-4 | WP_050649045.1 |
| Erwinia persicina | WP_062748343.1 | Aliivibrio salmonicida | WP_012551314.1 |
| Pantoea sp. At-9b | WP_013507482.1 | Vibrio rhizosphaerae | WP_038185523.1 |
| bacteria symbiont BFo1 of Frankliniella occidentalis | WP_048917577.1 | Aliivibrio logei | WP_017020963.1 |
| Erwinia tasmaniensis | WP_012442801.1 | Vibrio genomosp. F10 | WP_017036869.1 |
| Erwinia sp. Leaf53 | WP_056235041.1 | Vibrio breoganii | WP_017243149.1 |
| Pantoea sp. PSNIH1 | WP_039381957.1 | Alteromonas macleodii | WP_041693341.1 |
| Pantoea ananatis | WP_029569357.1 | Vibrio hepatarius | WP_053410680.1 |
| Type-D symbiont of Plautia stali | WP_058972255.1 | Vibrio mytili | WP_041155288.1 |
| Pantoea stewartii | WP_006121550.1 | Vibrio scophthalmi | WP_005599707.1 |
| Pantoea dispersa | WP_058757568.1 | Psychromonas sp. SP041 | WP_025564742.1 |

Fig. 13 cont'd

| Microorganism | Genbank Accession | Microorganism | Genbank Accession |
|---|---|---|---|
| Type-B symbiont of Plautia stali | WP_059028282.1 | Vibrio sp. S234-5 | WP_045569648.1 |
| Pantoea sp. OXWO6B1 | WP_063877979.1 | Vibrio sp. 2423-01 | WP_061893561.1 |
| Yersinia | WP_019212311.1 | Marinobacter lipolyticus | WP_036190774.1 |
| Erwinia tracheiphila | WP_016191385.1 | Vibrio sp. MEBiC08052 | WP_059123026.1 |
| Yersinia frederiksenii | WP_004711220.1 | Alteromonas mediterranea | WP_012516591.1 |
| Pantoea sp. A4 | WP_026042541.1 | Vibrio toranzoniae | WP_060468829.1 |
| Yersinia rohdei | WP_032817534.1 | Vibrio cyclitrophicus | WP_016798923.1 |
| Yersinia aldovae | WP_049689167.1 | Vibrio rumoiensis | WP_017024312.1 |
| Rouxiella chamberiensis | WP_045048258.1 | Vibrio sinaloensis | WP_039481766.1 |
| Yersinia enterocolitica | WP_057648693.1 | Vibrio sp. N418 | WP_009384140.1 |
| Candidatus Hamiltonella defensa | WP_016857191.1 | Marinobacterium rhizophilum | WP_020679626.1 |
| Yersinia mollaretii | WP_050536989.1 | Psychromonas hadalis | WP_022942336.1 |
| Yersinia kristensenii | WP_004391858.1 | Vibrio kanaloae | WP_017055514.1 |
| Yersinia intermedia | WP_005191489.1 | Marinobacterium litorale | WP_027854294.1 |
| Serratia odorifera | WP_004957855.1 | Vibrio sp. ECSMB14106 | WP_046224925.1 |
| Yersinia bercovieri | WP_005271235.1 | Pseudomonas sp. NBRC 111130 | WP_054884750.1 |
| Serratia fonticola | WP_059199031.1 | Gallibacterium genomosp. 2 | WP_039136020.1 |
| Yersinia pekkanenii | WP_049613832.1 | Pseudomonas sp. 2-92(2010) | WP_028618504.1 |
| Serratia marcescens | WP_015962093.1 | Moritella sp. PE36 | WP_006030970.1 |
| Serratia rubidaea | WP_054305351.1 | Vibrio mimicus | WP_032467641.1 |
| Serratia proteamaculans | WP_012147158.1 | Shewanella waksmanii | WP_028772807.1 |
| Serratia ficaria | WP_061799193.1 | Vibrio fluvialis | WP_032081097.1 |
| Serratia liquefaciens | WP_044553804.1 | Pseudomonas vranovensis | WP_028942480.1 |
| Serratia sp. S4 | WP_017894211.1 | Idiomarina atlantica | WP_034733921.1 |
| Serratia grimesii | WP_037416107.1 | Gallibacterium genomosp. 1 | WP_039174494.1 |
| Serratia | WP_020837172.1 | Shewanella frigidimarina | WP_059745295.1 |
| Serratia plymuthica | WP_062868878.1 | Pseudomonas putida | WP_043209917.1 |
| Yersinia ruckeri | WP_004719425.1 | Vibrio halioticoli | WP_023405283.1 |
| Yersinia pseudotuberculosis | WP_050117587.1 | Simiduia agarivorans | WP_015047857.1 |
| Yersinia pestis | WP_054104465.1 | Alteromonas australica | WP_052806549.1 |
| Serratia sp. YD25 | WP_063918667.1 | Alteromonas marina | WP_039222473.1 |
| Yersinia pseudotuberculosis complex | WP_033848617.1 | Pseudomonas fluorescens | WP_034101515.1 |
| Serratia symbiotica | WP_061770918.1 | Pseudomonas sp. FeS53a | WP_044401466.1 |
| Serratia sp. FS14 | WP_044030326.1 | gamma proteobacterium IMCC1989 | WP_009670102.1 |
| Serratia sp. Leaf50 | WP_055774138.1 | Spiribacter salinus | WP_016352700.1 |

Fig. 13 cont'd

| Microorganism | Genbank Accession | Microorganism | Genbank Accession |
|---|---|---|---|
| Enterobacteriaceae bacterium B14 | WP_051014381.1 | Gallibacterium anatis | WP_039166724.1 |
| Serratia sp. M24T3 | WP_009638599.1 | Aggregatibacter actinomycetemcomitans | WP_005538626.1 |
| Yersinia nurmii | WP_049598056.1 | Cellvibrio sp. BR | WP_007638851.1 |
| Tatumella saanichensis | WP_029686453.1 | Aggregatibacter aphrophilus | WP_050694113.1 |
| Photorhabdus luminescens | WP_040154039.1 | Idiomarina sediminum | WP_051207005.1 |
| Xenorhabdus poinarii | WP_045959602.1 | Shewanella sediminis | WP_012144760.1 |
| Bartonella senegalensis | WP_019221445.1 | Vibrio furnissii | WP_055466655.1 |
| Xenorhabdus szentirmaii | WP_038235621.1 | Vibrio ezurae | WP_021715061.1 |
| Pectobacterium carotovorum | WP_039355229.1 | Pseudomonas sp. TTU2014-105ASC | WP_058063592.1 |
| Serratia sp. DD3 | WP_023490517.1 | Vibrio proteolyticus | WP_021707164.1 |
| Chania multitudinisentens | WP_024913341.1 | Balneatrix alpica | WP_051527455.1 |
| Pectobacterium betavasculorum | WP_039303019.1 | Pseudomonas parafulva | WP_039582433.1 |
| Pectobacterium atrosepticum | WP_011092244.1 | Shewanella loihica | WP_011867537.1 |
| Photorhabdus heterorhabditis | WP_054478023.1 | Vibrio vulnificus | WP_039541844.1 |
| Pectobacterium wasabiae | WP_012822481.1 | Nitrococcus mobilis | WP_040661924.1 |
| Xenorhabdus | WP_047769935.1 | Pseudomonas sp. 5 | WP_045186199.1 |
| Xenorhabdus nematophila | WP_038219455.1 | Pseudomonas trivialis | WP_049710900.1 |
| Bartonella henselae | WP_011181000.1 | Pseudomonas stutzeri | WP_038663939.1 |
| Bartonella koehlerae | WP_034459798.1 | Pseudomonas tuomuerensis | WP_039606725.1 |
| Tatumella morbirosei | WP_038023855.1 | Pseudomonas rhodesiae | WP_040266714.1 |
| Serratia sp. ATCC 39006 | WP_021014322.1 | Pseudomonas sp. ARP3 | WP_047881785.1 |
| Ewingella americana | WP_034793486.1 | Alteromonas sp. ALT199 | WP_025257082.1 |
| Hafnia alvei | WP_043490453.1 | Cellvibrio sp. pealriver | WP_049631176.1 |
| Rahnella | WP_013577374.1 | Psychromonas aquimarina | WP_028862328.1 |
| Rahnella aquatilis | WP_047612327.1 | Pseudomonas | WP_043314995.1 |
| Serratia sp. Leaf51 | WP_056776024.1 | Marinobacter daepoensis | WP_029654624.1 |
| Pectobacterium sp. SCC3193 | WP_014698702.1 | Sedimenticola selenatireducens | WP_037375012.1 |
| Bartonella bacilliformis | WP_041849739.1 | Pseudomonas sp. TKP | WP_024078144.1 |
| Dickeya sp. DW 0440 | WP_035339654.1 | Pseudomonas corrugata | WP_024777876.1 |
| Budvicia aquatica | WP_036017158.1 | Pseudomonas sp. AAC | WP_043268085.1 |
| Photorhabdus asymbiotica | WP_036770256.1 | Colwellia psychrerythraea | WP_033093585.1 |
| Brenneria sp. EniD312 | WP_009114521.1 | Shewanella sp. P1-14-1 | WP_055024157.1 |
| Xenorhabdus doucetiae | WP_045972447.1 | Pseudomonas fluorescens group | WP_033897276.1 |
| Proteus vulgaris | WP_036938822.1 | Pseudomonas mediterranea | WP_047704174.1 |
| Bartonella bovis | WP_010702680.1 | Marinobacter subterrani | WP_048497131.1 |

Fig. 13 cont'd

| Microorganism | Genbank Accession | Microorganism | Genbank Accession |
|---|---|---|---|
| Proteus mirabilis | WP_036971463.1 | Pseudohongiella spirulinae | WP_058022208.1 |
| Proteus hauseri | WP_023583078.1 | Pseudomonas sp. URHB0015 | WP_027616796.1 |
| Bartonella birtlesii | WP_006590207.1 | Pseudomonadaceae | WP_027588895.1 |
| Bartonella quintana | WP_042995424.1 | Marinobacter santoriniensis | WP_040886922.1 |
| Bartonella vinsonii | WP_015399203.1 | Vibrio metschnikovii | WP_040903602.1 |
| Xenorhabdus sp. NBAII XenSa04 | WP_047683929.1 | Pseudomonas sp. NBRC 111123 | WP_060483806.1 |
| Xenorhabdus bovienii | WP_038187361.1 | Pseudomonas sp. URMO17WK12:I8 | WP_027917043.1 |
| Bartonella sp. DB5-6 | WP_007553455.1 | Marinobacter sp. C1S70 | WP_022993199.1 |
| Bartonella taylorii | WP_004859565.1 | Pseudomonas fuscovaginae | WP_054057810.1 |
| Xenorhabdus khoisanae | WP_047963672.1 | Pseudomonas sp. M1 | WP_024128089.1 |
| Xenorhabdus cabanillasii | WP_038260250.1 | Pseudomonas poae | WP_015373328.1 |
| Bartonella washoensis | WP_006924009.1 | Marinobacter hydrocarbonoclasticus | WP_014422862.1 |
| bacteria symbiont BFo2 of Frankliniella occidentalis | WP_048911280.1 | Marinobacter sp. CP1 | WP_053113189.1 |
| Bartonella florencae | WP_019218918.1 | Marinobacter similis | WP_052471995.1 |
| Bartonella elizabethae | WP_005773162.1 | Moritella marina | WP_019441181.1 |
| Dickeya dadantii | WP_038924493.1 | Vibrio sp. RC586 | WP_001072884.1 |
| Lonsdalea quercina | WP_026739591.1 | Shewanella colwelliana | WP_028764686.1 |
| Photorhabdus temperata | WP_046974225.1 | Pseudomonas cremoricolorata | WP_038411439.1 |
| Dickeya dianthicola | WP_024104487.1 | Aestuariibacter salexigens | WP_051275567.1 |
| Arsenophonus nasoniae | WP_034249744.1 | Pseudomonas simiae | WP_047542440.1 |
| Dickeya zeae | WP_016943166.1 | Pseudomonas sp. SHC52 | WP_041020540.1 |
| Pragia fontium | WP_047782060.1 | Saccharospirillum impatiens | WP_051208090.1 |
| Bartonella melophagi | WP_007476822.1 | Pseudomonas chloritidismutans | WP_042927861.1 |
| Dickeya | WP_038917764.1 | Nitrincola sp. A-D6 | WP_036522654.1 |
| Leminorella grimontii | WP_027275775.1 | Shewanella sp. cp20 | WP_041509787.1 |
| Bartonella alsatica | WP_005864859.1 | gamma proteobacterium HTCC2207 | WP_007231113.1 |
| Dickeya sp. NCPPB 3274 | WP_042858576.1 | Pseudomonas sp. p21 | WP_063912245.1 |
| Bartonella queenslandensis | WP_039758997.1 | Alteromonas | WP_032094739.1 |
| Arsenophonus endosymbiont of Nilaparvata lugens | WP_032116478.1 | Pseudomonas batumici | WP_040071885.1 |
| Bartonella doshiae | WP_004855905.1 | Pseudomonas sp. Ant30-3 | WP_028620438.1 |
| Bartonella schoenbuchensis | WP_010704040.1 | Marinobacter sp. EVN1 | WP_023009487.1 |
| Providencia rettgeri | WP_004261323.1 | Pseudomonas monteilii | WP_060477249.1 |

Fig. 13 cont'd

| Microorganism | Genbank Accession | Microorganism | Genbank Accession |
|---|---|---|---|
| Dickeya sp. 2B12 | WP_033570629.1 | Actinobacillus | WP_005625006.1 |
| Dickeya solani | WP_022632063.1 | Pseudomonas sp. URMO17WK12:I4 | WP_027908969.1 |
| Tatumella | WP_025900954.1 | Pseudomonas sp. FGI182 | WP_025341124.1 |
| Morganella morganii | WP_024475151.1 | Pseudomonas agarici | WP_017132350.1 |
| Morganella | WP_004241531.1 | Pseudomonas veronii | WP_017849993.1 |
| Bartonella tribocorum | WP_038473768.1 | | |
| Dickeya chrysanthemi | WP_040002537.1 | | |
| Brenneria goodwinii | WP_048636333.1 | | |
| Dickeya paradisiaca | WP_015855063.1 | | |
| Candidatus Regiella insecticola | WP_006705673.1 | | |
| Dickeya sp. NCPPB 569 | WP_042868420.1 | | |
| Bartonella grahamii | WP_034451706.1 | | |
| Moellerella wisconsensis | WP_053907569.1 | | |
| Bartonella rattaustraliani | WP_019222387.1 | | |

Fig. 13 cont'd

| Microorganism | Genbank Accession | Microorganism | Genbank Accession |
|---|---|---|---|
| Pseudomonas | WP_003114686.1 | Bacillus sp. NH7I_1 | WP_060697735.1 |
| Pseudomonas aeruginosa | WP_023089494.1 | Bacillus sp. WP8 | WP_039180923.1 |
| Pseudomonas sp. 2_1_26 | WP_009316330.1 | Bacillus sp. Aph1 | WP_034271361.1 |
| Microvirgula aerodenitrificans | WP_028498979.1 | Azospirillum sp. B506 | WP_049975975.1 |
| Burkholderia contaminans | WP_039366334.1 | Virgibacillus pantothenticus | WP_050350407.1 |
| Burkholderia cepacia | WP_059525390.1 | Bacillus sp. B-jedd | WP_048826224.1 |
| Burkholderia cepacia complex | WP_027789658.1 | Bacillus simplex | WP_061142094.1 |
| Burkholderia cenocepacia | WP_043887199.1 | Virgibacillus sp. SK37 | WP_040955898.1 |
| Burkholderia oklahomensis | WP_010108306.1 | Bacillus thermotolerans | WP_039238772.1 |
| Burkholderia | WP_048024784.1 | unclassified Bacillaceae | WP_040037859.1 |
| Burkholderia anthina | WP_059640804.1 | Bacillus sp. Root920 | WP_056766977.1 |
| Burkholderia lata | WP_011354275.1 | Anoxybacillus thermarum | WP_043966577.1 |
| Burkholderia sp. MSh1 | WP_031398726.1 | Bacillus coahuilensis | WP_010174447.1 |
| Burkholderia sp. MSh2 | WP_034198724.1 | Bacillus safensis | WP_044332225.1 |
| Burkholderia sp. ABCPW 11 | WP_059505050.1 | Alkalibacillus haloalkaliphilus | WP_017187026.1 |
| Burkholderia seminalis | WP_059556868.1 | Bacillus sp. J33 | WP_034263269.1 |
| Burkholderia pseudomallei | WP_004551415.1 | Viridibacillus arenosi | WP_038188166.1 |
| Burkholderia thailandensis | WP_009900942.1 | Bacillus sp. FJAT-14578 | WP_028395275.1 |
| Burkholderia glumae | WP_052498364.1 | Oceanobacillus kimchii | WP_017797441.1 |
| Burkholderia plantarii | WP_055139495.1 | Bacillus decisifrondis | WP_053592881.1 |
| Pseudomonas mandelii | WP_050482791.1 | Virgibacillus halodenitrificans | WP_019379016.1 |
| Pseudomonas fluorescens | WP_047337084.1 | Gracilibacillus sp. Awa-1 | WP_058306868.1 |
| Nitrococcus mobilis | WP_005004375.1 | Bacillus sp. MSP13 | WP_039074850.1 |
| Pseudomonas protegens | WP_041752315.1 | Lysinibacillus macroides | WP_053996681.1 |
| Pseudomonas sp. PH1b | WP_025129888.1 | Bacillus sp. FJAT-27251 | WP_053364401.1 |
| Pseudomonas putida | WP_023535698.1 | Lysinibacillus massiliensis | WP_036180684.1 |
| Pseudomonas sp. ABAC61 | WP_058436407.1 | Lysinibacillus sp. FJAT-14745 | WP_053485081.1 |
| Pseudomonas veronii | WP_032804924.1 | Sphaerobacter thermophilus | WP_052295394.1 |
| Pseudomonas sp. ARP3 | WP_053060097.1 | Bacillus sp. SA2-6 | WP_046525629.1 |
| Pseudomonas sp. PAMC 25886 | WP_010169497.1 | Bacillus selenatarsenatis | WP_041968022.1 |

Fig. 14

| Microorganism | Genbank Accession | Microorganism | Genbank Accession |
|---|---|---|---|
| Pseudomonas sp. MRSN12121 | WP_044463386.1 | Gracilimonas tropica | WP_020401972.1 |
| Pseudomonas rhodesiae | WP_040269528.1 | Oceanobacillus oncorhynchi | WP_042530686.1 |
| Pseudomonas sp. 2(2015) | WP_045198122.1 | Bacillus muralis | WP_057915654.1 |
| Pseudomonas sp. BRG-100 | WP_032876543.1 | Bacillus malacitensis | WP_059291772.1 |
| Pseudomonas chlororaphis | WP_052712847.1 | Anoxybacillus sp. KU2-6(11) | WP_035048665.1 |
| Pseudomonas sp. CFII68 | WP_018605339.1 | Domibacillus enclensis | WP_052698560.1 |
| Pseudomonas helleri | WP_048388690.1 | Bacillus axarquiensis | WP_059352147.1 |
| Pseudomonas sp. Root569 | WP_056846015.1 | Brevibacterium halotolerans | WP_059335649.1 |
| Pseudomonas sp. FH1 | WP_033901147.1 | Lysinibacillus xylanilyticus | WP_049667404.1 |
| Pseudomonas sp. 2-92(2010) | WP_050587840.1 | Bacillus tequilensis | WP_024714703.1 |
| Pseudomonas libanensis | WP_059396815.1 | Bacillus sp. UNC322MFChir4.1 | WP_035432514.1 |
| Pseudomonas simiae | WP_047543762.1 | Solibacillus | WP_008408138.1 |
| Alcanivorax dieselolei | WP_014994844.1 | Sporosarcina koreensis | WP_060206543.1 |
| Pseudomonas thivervalensis | WP_053121146.1 | Lysinibacillus sphaericus | WP_010860294.1 |
| Pseudomonas synxantha | WP_057025332.1 | Lysinibacillus sp. F5 | WP_058845031.1 |
| bacterium JKG1 | WP_029214447.1 | Paenisporosarcina sp. TG-14 | WP_017380005.1 |
| Gracilibacillus halophilus | WP_003467031.1 | Bacillus licheniformis | WP_043925819.1 |
| Pseudomonas syringae | WP_024668534.1 | Lysinibacillus odysseyi | WP_036151007.1 |
| bacterium mt3 | WP_054949256.1 | Anoxybacillus sp. BCO1 | WP_042894993.1 |
| Pseudomonas sp. ADP | WP_058489589.1 | Viridibacillus arvi | WP_053416717.1 |
| Pseudomonas syringae group genomosp. 7 | WP_055005986.1 | Geobacillus thermodenitrificans | WP_029760552.1 |
| Pseudomonas syringae group genomosp. 3 | WP_057415224.1 | Geobacillus sp. PA-3 | WP_060476126.1 |
| Pseudomonas amygdali | WP_005762842.1 | Geobacillus sp. G11MC16 | WP_008880976.1 |
| Azospirillum lipoferum | WP_014188759.1 | Bacillus velezensis | WP_029974105.1 |
| Bacillus aquimaris | WP_052011500.1 | Halapricum salinum | WP_049992575.1 |
| Pseudomonas syringae group | WP_007245942.1 | Bacillus stratosphericus | WP_039964166.1 |
| Pseudomonas caricapapayae | WP_055009862.1 | Bacillales | WP_014114896.1 |
| Bradyrhizobium | WP_024580699.1 | Solibacillus silvestris | WP_014823056.1 |
| Oscillochloris trichoides | WP_006562625.1 | Bhargavaea cecembensis | WP_008300106.1 |
| Bacillus enclensis | WP_058298109.1 | Sporosarcina sp. EUR3 2.2.2 | WP_024534129.1 |
| Pseudomonas savastanoi | WP_004665562.1 | Bacillus sp. | WP_052586469.1 |

Fig. 14 continued

| Microorganism | Genbank Accession | Microorganism | Genbank Accession |
|---|---|---|---|
| Bacillus sp. SG-1 | WP_006836445.1 | Bacillus xiamenensis | WP_008360695.1 |
| Pseudomonas avellanae | WP_005617735.1 | Bacilli bacterium VT-13-104 | WP_047184596.1 |
| Microbulbifer variabilis | WP_020415351.1 | Bacillus sp. DW5-4 | WP_034325145.1 |
| Pseudomonas fuscovaginae | WP_054064572.1 | Bacillus altitudinis | WP_047945217.1 |
| Bacillus vietnamensis | WP_051758539.1 | Planomicrobium sp. ES2 | WP_052652109.1 |
| Bacillus sp. LL01 | WP_047970983.1 | Geobacillus subterraneus | WP_063167279.1 |
| Caldalkalibacillus thermarum | WP_007503034.1 | Geobacillus | WP_042381875.1 |
| Bacillus marisflavi | WP_048013478.1 | Oceanobacillus caeni | WP_060668740.1 |
| Pseudomonas cichorii | WP_025259793.1 | Lysinibacillus sp. ZYM-1 | WP_054612847.1 |
| Aeribacillus pallidus | WP_063386559.1 | Lysinibacillus varians | WP_025220363.1 |
| Bacillus azotoformans | WP_035196603.1 | Brevibacterium frigoritolerans | WP_063589832.1 |
| Desmospora sp. 8437 | WP_040387746.1 | Bacillus sp. BSC154 | WP_041906541.1 |
| Bacillus horikoshii | WP_063559773.1 | Terribacillus aidingensis | WP_038565035.1 |
| Halobacillus halophilus | WP_014644096.1 | Alicyclobacillus pomorum | WP_051375075.1 |
| Bacillus humi | WP_057999505.1 | Gracilibacillus boraciitolerans | WP_035724544.1 |
| Salimicrobium jeotgali | WP_008587369.1 | Virgibacillus soli | WP_057982217.1 |
| Jeotgalibacillus malaysiensis | WP_039810607.1 | Bacillus sp. 37MA | WP_018394222.1 |
| Geobacillus sp. Y4.1MC1 | WP_013400205.1 | Planomicrobium glaciei | WP_053167718.1 |
| Pseudomonas agarici | WP_060783693.1 | Bacillus cihuensis | WP_028392653.1 |
| Bacillus sp. Leaf406 | WP_056534732.1 | Bacillus cereus | WP_016116829.1 |
| Desulfovibrio desulfuricans | WP_041724102.1 | Geobacillus sp. JS12 | WP_063193197.1 |
| Anaerobacillus macyae | WP_053216218.1 | Kurthia massiliensis | WP_010288409.1 |
| Pontibacillus halophilus | WP_026801400.1 | Bacillus sp. Soil768D1 | WP_057215430.1 |
| Geobacillus toebii | WP_062755081.1 | Bacillus sonorensis | WP_006636053.1 |
| Bacillus sp. m3-13 | WP_010195203.1 | Bacillus sp. FJAT-20673 | WP_063574832.1 |
| Geobacillus thermoglucosidasius | WP_042384399.1 | Lysinibacillus boronitolerans | WP_036078490.1 |
| Pontibacillus marinus | WP_027447035.1 | Bacillus sp. Leaf13 | WP_056521250.1 |
| Geobacillus sp. WCH70 | WP_015864892.1 | Bacillus sp. 72 | WP_051927823.1 |
| Thalassobacillus sp. TM-1 | WP_062440761.1 | Geobacillus sp. JF8 | WP_020961008.1 |
| Bacillus sp. CHD6a | WP_060666910.1 | Bacillus butanolivorans | WP_053347927.1 |
| Bacillaceae | WP_003248477.1 | Geobacillus sp. C56-T3 | WP_013144393.1 |
| Bacillus sp. SA1-12 | WP_046590138.1 | Bacillus pseudomycoides | WP_006096312.1 |
| Bacillus massiliogorillae | WP_042345107.1 | Roseiflexus sp. RS-1 | WP_011954829.1 |

Fig. 14 continued

| Microorganism | Genbank Accession | Microorganism | Genbank Accession |
|---|---|---|---|
| Pontibacillus chungwhensis | WP_036782710.1 | Bacillus sp. 95MFCvi2.1 | WP_018782033.1 |
| Thermogemmatispora carboxidivorans | WP_052888923.1 | Bacillus cereus group | WP_040119032.1 |
| Salinibacillus aidingensis | WP_044163325.1 | Lysinibacillus fusiformis | WP_004225913.1 |
| Bacillus sp. X1(2014) | WP_038536892.1 | Bacillus mycoides | WP_041488594.1 |
| Lentibacillus jeotgali | WP_010532310.1 | Lysinibacillus sp. LK3 | WP_048391047.1 |
| Bacillus ginsengihumi | WP_035353906.1 | Bacillus sp. Soil745 | WP_057279191.1 |
| Jeotgalibacillus soli Cunha et al. 2012 | WP_052474929.1 | Bacillus sp. FJAT-27916 | WP_049669789.1 |
| Bacillus shackletonii | WP_055738952.1 | Thermomicrobium roseum | WP_012642614.1 |
| Pontibacillus yanchengensis | WP_036821077.1 | Geobacillus sp. CAMR5420 | WP_033026053.1 |
| Bacillus niacini | WP_034673537.1 | Bacillus sp. 105MF | WP_018764645.1 |
| Bacillus sp. J37 | WP_026561814.1 | Bacillus manliponensis | WP_034642812.1 |
| Bacillus vireti | WP_024027849.1 | Bacillus sp. FJAT-27245 | WP_053367481.1 |
| Bacillus cibi | WP_029566209.1 | Lysinibacillus sp. BF-4 | WP_036142602.1 |
| Bacillus alveayuensis | WP_052659551.1 | Lysinibacillus | WP_036119793.1 |
| Bacillus indicus | WP_029278756.1 | Opitutus terrae | WP_012376455.1 |
| Bacillus bataviensis | WP_007086491.1 | Domibacillus robiginosus | WP_050181303.1 |
| Thalassobacillus devorans | WP_028783548.1 | Bacillus aminovorans | WP_063975020.1 |
| Chloroflexus aggregans | WP_012615533.1 | Bacillus sp. 1NLA3E | WP_041580669.1 |
| Bacillus fordii | WP_018707485.1 | Sporosarcina newyorkensis | WP_009497990.1 |
| Virgibacillus sp. SK-1 | WP_053218805.1 | Bacillus sp. GeD10 | WP_006915660.1 |
| Bacillus smithii | WP_048623884.1 | Paenisporosarcina sp. TG20 | WP_019414907.1 |
| Halobacillus kuroshimensis | WP_027956472.1 | Planococcus antarcticus | WP_006831222.1 |
| Geobacillus caldoxylosilyticus | WP_017434868.1 | Bacillus sp. UNC437CL72CviS29 | WP_026593876.1 |
| Bacillus massilioanorexius | WP_019243994.1 | Bacillus sp. 123MFChir2 | WP_020061371.1 |
| Geobacillus stearothermophilus | WP_043905856.1 | Halobacterium sp. CBA1132 | WP_058982752.1 |
| Bacillus circulans | WP_061798785.1 | Streptomyces sp. MBT76 | WP_058042239.1 |
| Ktedonobacter racemifer | WP_007913623.1 | Bacillus sp. FJAT-13831 | WP_017153674.1 |
| Jeotgalibacillus alimentarius | WP_052474147.1 | Bacillus gaemokensis | WP_033676253.1 |
| Bacillus sp. FJAT-27445 | WP_059171493.1 | Bacilli | WP_000616738.1 |
| Bacillus | WP_009795315.1 | Sporolactobacillus laevolacticus | WP_023509936.1 |
| Bacillus nealsonii | WP_016202883.1 | Alicyclobacillus contaminans | WP_051321775.1 |
| Sporosarcina globispora | WP_053434007.1 | Bacillus cytotoxicus | WP_012095948.1 |

Fig. 14 continued

| Microorganism | Genbank Accession | Microorganism | Genbank Accession |
|---|---|---|---|
| Oceanobacillus picturae | WP_036574619.1 | Conexibacter woesei | WP_035127957.1 |
| Gracilibacillus lacisalsi | WP_018934096.1 | Halobacterium hubeiense | WP_059056695.1 |
| Oceanobacillus sp. S5 | WP_040979050.1 | Bacillus sp. H1a | WP_025148828.1 |
| Alicyclobacillus macrosporangiidus | WP_051662824.1 | Bacillus thuringiensis | WP_023523256.1 |
| Bacillus sp. UNC438CL73TsuS30 | WP_026572089.1 | Patulibacter americanus | WP_022928512.1 |
| Bacillus sp. ZYK | WP_017756202.1 | Bacillus sp. B14905 | WP_043990721.1 |
| Bacillus psychrosaccharolyticus | WP_051387396.1 | Planococcus kocurii | WP_058385831.1 |
| Ornithinibacillus contaminans | WP_047979667.1 | Planococcus sp. CAU13 | WP_033543886.1 |
| Anoxybacillus tepidamans | WP_027410481.1 | Sporosarcina ureae | WP_029055120.1 |
| Oceanobacillus manasiensis | WP_042222742.1 | Geobacillus icigianus | WP_033018318.1 |
| Bacillus methanolicus | WP_004439139.1 | Sporolactobacillus terrae | WP_051577709.1 |
| Halobacillus sp. BBL2006 | WP_035548017.1 | Tuberibacillus calidus | WP_027724185.1 |
| Oceanobacillus massiliensis | WP_010647294.1 | Geobacillus vulcani | WP_031407519.1 |
| Bacillus flexus | WP_061784908.1 | Bacillus coagulans | WP_035188982.1 |
| Chloroflexus sp. Y-396-1 | WP_028459931.1 | Bacillus sp. LK2 | WP_048374368.1 |
| Ornithinibacillus californiensis | WP_047983652.1 | Kurthia huakuii | WP_029499533.1 |
| Halobacillus | WP_035511377.1 | Halalkalibacillus halophilus | WP_027964378.1 |
| Bacillus encimensis | WP_063383670.1 | Domibacillus tundrae | WP_052728327.1 |
| Bacillus sp. JS | WP_041521409.1 | bacterium SIT5 | WP_062354774.1 |
| Anoxybacillus flavithermus | WP_006320635.1 | Planococcus sp. PAMC 21323 | WP_038703416.1 |
| Bacillus badius | WP_063441135.1 | Geobacillus kaustophilus | WP_044736356.1 |
| Bacillus rubiinfantis | WP_042354695.1 | Exiguobacterium | WP_035412678.1 |
| Desulfitibacter alkalitolerans | WP_051534294.1 | Streptomyces sp. NRRL S-813 | WP_051844821.1 |
| Bacillus sp. RP1137 | WP_029319903.1 | Kurthia sp. JC8E | WP_010304177.1 |
| Balneola vulgaris | WP_018127710.1 | Roseiflexus castenholzii | WP_012122664.1 |
| Bacillus aryabhattai | WP_045295385.1 | Bacillus anthracis | WP_000616727.1 |
| Bacillus niameyensis | WP_062109560.1 | Bacillus sp. OxB-1 | WP_041070670.1 |
| Bacillus sp. FJAT-25547 | WP_057761139.1 | Halolamina rubra | WP_049981866.1 |
| Bacillus acidiproducens | WP_051086254.1 | Bacillus sp. FJAT-27997 | WP_049682973.1 |
| Bacillus thermoamylovorans | WP_034768563.1 | Salinarchaeum sp. Harcht-Bsk1 | WP_020447809.1 |

Fig. 14 continued

| Microorganism | Genbank Accession | Microorganism | Genbank Accession |
|---|---|---|---|
| Bacillus sp. URHB0009 | WP_027322137.1 | Bacillus sp. GZT | WP_062923621.1 |
| Halobacillus sp. BAB-2008 | WP_008637585.1 | Sporosarcina sp. ZBG7A | WP_039044539.1 |
| Bacillus sp. A053 | WP_040082038.1 | Bacillus sp. UMTAT18 | WP_046199487.1 |
| Bacillus sp. UNC41MFS5 | WP_026563219.1 | Halobacteriaceae archaeon SB9 | WP_058581597.1 |
| Bacillus sp. Soil531 | WP_057274095.1 | Halopiger djelfamassiliensis | WP_049923288.1 |
| Bacillus siamensis | WP_016938462.1 | Alicyclobacillus herbarius | WP_051343768.1 |
| Bacillus farraginis | WP_058005647.1 | Exiguobacterium indicum | WP_058704972.1 |
| Bacillus subtilis | WP_014477756.1 | Natronococcus amylolyticus | WP_005555286.1 |
| Bacillus subterraneus | WP_044395766.1 | Lysinibacillus manganicus | WP_036190256.1 |
| Bacillus gobiensis | WP_053603894.1 | Exiguobacterium sp. BMC-KP | WP_053452202.1 |
| Paucisalibacillus sp. EB02 | WP_042143024.1 | Halorubrum sp. BV1 | WP_049982315.1 |
| Bacillus amyloliquefaciens | WP_047476771.1 | Haloarcula vallismortis | WP_004517947.1 |
| Bacillus sp. SIT10 | WP_050616161.1 | Halostagnicola sp. A56 | WP_050051196.1 |
| Bacillus sp. Root147 | WP_057233096.1 | Haloarcula japonica | WP_004592792.1 |
| Bacillus koreensis | WP_053400748.1 | Streptomyces sp. ATexAB-D23 | WP_018554385.1 |
| Bacillus sp. 278922_107 | WP_028411869.1 | Alicyclobacillus ferrooxydans | WP_054969223.1 |
| Pontibacillus litoralis | WP_052127216.1 | Solirubrobacter sp. URHD0082 | WP_051323957.1 |
| Lysinibacillus contaminans | WP_053582362.1 | Halorubrum hochstenium | WP_008580740.1 |
| Bacillus sp. JFL15 | WP_049627228.1 | Haloferax mucosum | WP_008317500.1 |
| Anoxybacillus kamchatkensis | WP_019417289.1 | Haloarcula amylolytica | WP_008309243.1 |
| Bacillus sp. FJAT-25496 | WP_057772306.1 | Exiguobacterium oxidotolerans | WP_029332750.1 |
| Bacillus glyciniformans | WP_048355295.1 | Haloarcula | WP_050038036.1 |
| Bacillus sp. FF4 | WP_042460803.1 | Exiguobacterium acetylicum | WP_050677396.1 |
| Bacillus sp. SDLI1 | WP_060964475.1 | Haloarcula sp. CBA1127 | WP_058995943.1 |
| Bacillus atrophaeus | WP_010789607.1 | Halopenitus sp. DYS4 | WP_058366711.1 |
| Oceanobacillus iheyensis | WP_011066719.1 | Halorubrum tebenquichense | WP_006630090.1 |
| Bacillus megaterium | WP_013085283.1 | Haladaptatus paucihalophilus | WP_007978613.1 |
| Bacillus sp. Root239 | WP_057244921.1 | Solirubrobacter soli | WP_028064223.1 |
| Chloroflexus sp. MS-G | WP_031458749.1 | Oscillatoriales cyanobacterium MTP1 | WP_058883121.1 |
| Anoxybacillus geothermalis | WP_044745973.1 | Haloarcula marismortui | WP_011223264.1 |
| Lysinibacillus sinduriensis | WP_036197348.1 | Sporosarcina sp. D27 | WP_025786354.1 |

Fig. 14 continued

| Microorganism | Genbank Accession | Microorganism | Genbank Accession |
|---|---|---|---|
| Anoxybacillus | WP_009361645.1 | Exiguobacterium sp. Leaf187 | WP_055966688.1 |
| Bacillus endophyticus | WP_019391067.1 | Haloarcula hispanica | WP_014040312.1 |
| Bacillus cecembensis | WP_057988977.1 | Halosimplex carlsbadense | WP_006884453.1 |
| Bacillus vallismortis | WP_061571926.1 | Exiguobacterium sp. ZWU0009 | WP_047395159.1 |
| Bacillus sp. G1(2015b) | WP_058838176.1 | Halorhabdus utahensis | WP_015788577.1 |
| Bacillus sp. NSP9.1 | WP_026588395.1 | Planococcus halocryophilus | WP_008497280.1 |
| Bacillus sp. FJAT-27231 | WP_049663918.1 | Verrucomicrobia bacterium SCGC AAA168-F10 | WP_038126170.1 |
| Paucisalibacillus globulus | WP_026906974.1 | Exiguobacterium sp. OS-77 | WP_035398779.1 |
| Ureibacillus thermosphaericus | WP_016837030.1 | Halalkalicoccus jeotgali | WP_008417532.1 |
| Virgibacillus sp. Vm-5 | WP_038243188.1 | Planococcus donghaensis | WP_008428950.1 |
| Bacillus subtilis group | WP_013390633.1 | Halorubrum halophilum | WP_050032715.1 |
| Chloroflexus | WP_012259490.1 | Exiguobacterium sibiricum | WP_012369533.1 |
| Bacillus sp. EGD-AK10 | WP_021480367.1 | Psychrobacillus sp. FJAT-21963 | WP_056832867.1 |
| Bacillus kribbensis | WP_035322454.1 | Bacillus sp. FJAT-25509 | WP_056473274.1 |
| Bacillus sp. REN51N | WP_040056994.1 | Halorubrum arcis | WP_007992958.1 |
| Virgibacillus sp. CM-4 | WP_021288888.1 | Haloarcula sp. SL3 | WP_053968146.1 |
| Paenisporosarcina sp. HGH0030 | WP_016426536.1 | Haloferax mediterranei | WP_004056921.1 |
| Bacillus sp. EB01 | WP_043934015.1 | Haloarcula argentinensis | WP_005534453.1 |
| Bacillus panaciterrae | WP_028399695.1 | Bacillus sp. FJAT-22090 | WP_053588542.1 |
| Bacillus sp. 171095_106 | WP_028410453.1 | Halolamina pelagica | WP_054583766.1 |
| Ornithinibacillus scapharcae | WP_010097123.1 | Geobacillus sp. 12AMOR1 | WP_047818914.1 |
| Bacillus nakamurai | WP_061520043.1 | Microcystis aeruginosa | WP_004163819.1 |
| Jeotgalibacillus campisalis | WP_041060570.1 | Halorubrum sp. T3 | WP_017343453.1 |
| Bacillus mojavensis | WP_029441396.1 | Exiguobacterium sp. NG55 | WP_035387788.1 |
| Anoxybacillus suryakundensis | WP_055440175.1 | Halorubrum | WP_004598556.1 |
| Bacillus sp. FF3 | WP_042474379.1 | Exiguobacterium marinum | WP_026826747.1 |
| Bacillus sp. TH008 | WP_046130688.1 | Halorubrum aidingense | WP_007999743.1 |
| Bacillus sp. AM 13(2015) | WP_059375200.1 | | |
| Bacillus pumilus | WP_044142126.1 | | |
| Bacillus sp. CMAA 1185 | WP_046160765.1 | | |
| Bacillus sp. FJAT-18017 | WP_053598618.1 | | |
| Bacillus firmus | WP_048011096.1 | | |

Fig. 14 continued

| Microorganism | Genbank Accession | Microorganism | Genbank Accession |
|---|---|---|---|
| Pseudomonas | WP_003106950.1 | Brevundimonas diminuta | WP_003165630.1 |
| Pseudomonas aeruginosa | WP_023131684.1 | Erythrobacter sp. NAP1 | WP_007164103.1 |
| Pseudomonas aeruginosa group | WP_009877106.1 | Erwinia persicina | WP_062742761.1 |
| Microvirgula aerodenitrificans | WP_028498980.1 | Leisingera sp. ANG-M1 | WP_039168607.1 |
| Burkholderia cepacia complex | WP_006484772.1 | Shinella | WP_050742571.1 |
| Burkholderia anthina | WP_059584467.1 | Sphingomonas sp. KC8 | WP_010125831.1 |
| Burkholderia cenocepacia | WP_060211908.1 | Pseudomonas taeanensis | WP_025166189.1 |
| Burkholderia | WP_011547168.1 | Caulobacter sp. OV484 | WP_047404747.1 |
| Burkholderia pseudomallei | WP_004549567.1 | Pseudomonas sp. NBRC 111135 | WP_054910491.1 |
| Burkholderia lata | WP_011354276.1 | Pseudomonas sp. Leaf15 | WP_056858237.1 |
| Burkholderia contaminans | WP_039366337.1 | Ruegeria pomeroyi | WP_011047295.1 |
| Burkholderia cepacia | WP_059525391.1 | Candidatus Filomicrobium marinum | WP_046475955.1 |
| Burkholderia thailandensis | WP_009897990.1 | Ensifer sp. Br816 | WP_018234899.1 |
| Burkholderia oklahomensis | WP_010108308.1 | Caulobacter | WP_056050097.1 |
| Pseudomonas fluorescens | WP_016979925.1 | Rhizobium sp. Leaf341 | WP_062692519.1 |
| Pseudomonas sp. 2-92(2010) | WP_028616070.1 | Rhizobium | WP_062470505.1 |
| Pseudomonas azotoformans | WP_061436824.1 | Ensifer sojae | WP_034859346.1 |
| Pseudomonas sp. FH1 | WP_033901146.1 | Ruegeria mobilis | WP_005628022.1 |
| Pseudomonas thivervalensis | WP_053121148.1 | Sedimentitalea nanhaiensis | WP_027263471.1 |
| Pseudomonas synxantha | WP_057025331.1 | Porphyrobacter cryptus | WP_027441928.1 |
| Pseudomonas sp. CHM02 | WP_025854584.1 | Porphyrobacter sp. AAP60 | WP_054117689.1 |
| Pseudomonas mandelii | WP_033056094.1 | Ewingella americana | WP_034789690.1 |
| Pseudomonas fluorescens group | WP_043050251.1 | Chromobacterium vaccinii | WP_046155509.1 |
| Alcanivorax dieselolei | WP_014994845.1 | Ruminococcus albus | WP_043538032.1 |
| Nitrococcus mobilis | WP_005004372.1 | Variovorax paradoxus | WP_042576834.1 |
| Pseudomonas sp. 2(2015) | WP_045198124.1 | Parvularcula bermudensis | WP_013300785.1 |
| Pseudomonas sp. PH1b | WP_025129887.1 | Rubellimicrobium thermophilum | WP_021097656.1 |
| Pseudomonas sp. PAMC 25886 | WP_010169498.1 | Dechloromonas aromatica | WP_011289796.1 |

Fig. 15

| Microorganism | Genbank Accession | Microorganism | Genbank Accession |
|---|---|---|---|
| Pseudomonas putida | WP_023535597.1 | Variovorax boronicumulans | WP_062477800.1 |
| Pseudomonas helleri | WP_048388689.1 | Sphingomonas sp. MM-1 | WP_015457563.1 |
| Pseudomonas sp. Os17 | WP_060839803.1 | Phaeobacter inhibens | WP_061049393.1 |
| Pseudomonas sp. ABAC61 | WP_058436409.1 | Variovorax sp. Root473 | WP_056580651.1 |
| Pseudomonas protegens | WP_041752761.1 | Silicibacter sp. TrichCH4B | WP_009177420.1 |
| Pseudomonas sp. St29 | WP_060843902.1 | Phaeospirillum molischianum | WP_040566020.1 |
| Vibrio | WP_029223919.1 | Pseudomonas sp. PAMC 26793 | WP_017477817.1 |
| Zymobacter palmae | WP_027706238.1 | Pseudomonas simiae | WP_047543395.1 |
| Vibrio splendidus | WP_017095663.1 | Sinorhizobium arboris | WP_027999396.1 |
| Vibrio nigripulchritudo | WP_022598767.1 | Caulobacter sp. AP07 | WP_007669693.1 |
| Vibrio vulnificus | WP_011081756.1 | Porphyrobacter mercurialis | WP_039096260.1 |
| Pseudomonas sp. ADP | WP_058489588.1 | Oceanicola sp. S124 | WP_010137633.1 |
| Pseudomonas fuscovaginae | WP_054061580.1 | Pseudogulbenkiania ferrooxidans | WP_021478802.1 |
| Desulfovibrio desulfuricans | WP_012624972.1 | Erythrobacter gangjinensis | WP_047005672.1 |
| Pseudoalteromonas luteoviolacea | WP_063364351.1 | Klebsiella oxytoca | WP_004131235.1 |
| Pseudomonas entomophila | WP_011533710.1 | Labrenzia aggregata | WP_006935802.1 |
| Pseudomonas sp. KG01 | WP_048731723.1 | Caulobacter sp. K31 | WP_012287297.1 |
| Pseudomonas cichorii | WP_025259794.1 | Erythrobacter longus | WP_051698842.1 |
| Pseudomonas rhizosphaerae | WP_043188773.1 | Pseudomonas endophytica | WP_055101787.1 |
| Azospirillum lipoferum | WP_014188758.1 | Providencia burhodogranariea | WP_008911142.1 |
| Pseudomonas fulva | WP_042556657.1 | Caulobacter sp. CCH5-E12 | WP_062099535.1 |
| Brenneria sp. EniD312 | WP_009114600.1 | Ruegeria atlantica | WP_058276921.1 |
| Lonsdalea quercina | WP_026739756.1 | Brevundimonas aveniformis | WP_029086159.1 |
| Azospirillum sp. B506 | WP_042693433.1 | Phaeobacter gallaeciensis | WP_014879244.1 |
| Pseudomonas monteilii | WP_060393461.1 | Erythrobacter atlanticus | WP_048885888.1 |
| Pseudomonas syringae | WP_017708113.1 | Ensifer sp. USDA 6670 | WP_029959387.1 |
| Pseudomonas syringae group | WP_005762840.1 | Hellea balneolensis | WP_026940740.1 |
| Pseudomonas amygdali | WP_005738477.1 | Sinorhizobium meliloti | WP_010968657.1 |
| Pseudomonas savastanoi | WP_019741432.1 | Sinorhizobium sp. CCBAU 05631 | WP_037425973.1 |

Fig. 15 continued

| Microorganism | Genbank Accession | Microorganism | Genbank Accession |
|---|---|---|---|
| Pseudomonas syringae group genomosp. 3 | WP_054091058.1 | Ruegeria sp. CECT 5091 | WP_058284168.1 |
| Microbulbifer variabilis | WP_020415350.1 | Ruegeria sp. ANG-R | WP_039538859.1 |
| Tolypothrix campylonemoides | WP_041041287.1 | Caulobacter vibrioides | WP_035017242.1 |
| Nodosilinea nodulosa | WP_017298636.1 | Rhodobacteraceae bacterium KLH11 | WP_008755607.1 |
| Leptolyngbya sp. NIES-2104 | WP_059001045.1 | Caulobacter segnis | WP_013078409.1 |
| Agrobacterium tumefaciens | WP_035225456.1 | Klebsiella | WP_004871378.1 |
| Calothrix sp. PCC 7103 | WP_019493169.1 | Yersinia | WP_050084882.1 |
| Cellvibrio sp. OA-2007 | WP_062064078.1 | Pseudomonas libanensis | WP_057012799.1 |
| Scytonema tolypothrichoides | WP_048868701.1 | Rhodobacter sp. SW2 | WP_008031693.1 |
| Pantoea sp. RIT-PI-b | WP_049853162.1 | Labrenzia sp. DG1229 | WP_035899651.1 |
| Stanieria cyanosphaera | WP_015195188.1 | Ruegeria halocynthiae | WP_037310730.1 |
| Pseudomonas chlororaphis | WP_009049359.1 | Pantoea | WP_045815650.1 |
| Runella limosa | WP_028525382.1 | Mannheimia varigena | WP_025216860.1 |
| Pedobacter sp. V48 | WP_048904841.1 | Enterobacteriaceae | WP_049084995.1 |
| Pedobacter sp. PACM 27299 | WP_062550966.1 | Pseudomonas fragi | WP_016779407.1 |
| Pantoea rodasii | WP_039334894.1 | Caulobacter sp. Root655 | WP_056724929.1 |
| Crinalium epipsammum | WP_015201559.1 | Acidovorax delafieldii | WP_060977469.1 |
| Brenneria goodwinii | WP_048636391.1 | Caulobacter henricii | WP_062145109.1 |
| Pseudomonas frederiksbergensis | WP_039591223.1 | Sinorhizobium fredii | WP_037432167.1 |
| Snodgrassella alvi | WP_037473754.1 | Rhizobium giardinii | WP_018324075.1 |
| Pedobacter sp. R20-19 | WP_029287121.1 | Porphyrobacter sp. HL-46 | WP_036800189.1 |
| Pseudomonas agarici | WP_017133639.1 | Erythrobacter marinus | WP_047093931.1 |
| Bradyrhizobium | WP_024580698.1 | Altererythrobacter marensis | WP_047806000.1 |
| Hassallia byssoidea | WP_039743314.1 | Kordiimonas gwangyangensis | WP_020399032.1 |
| Type-E symbiont of Plautia stali | WP_058962445.1 | Pseudomonas sp. 313 | WP_017639561.1 |
| Pseudomonas kilonensis | WP_046062292.1 | Yersinia intermedia | WP_005183468.1 |
| Alcanivorax hongdengensis | WP_008930023.1 | Ensifer | WP_025425846.1 |
| Oscillatoria nigro-viridis | WP_015179369.1 | Ruegeria conchae | WP_010442824.1 |
| Microcoleus vaginatus | WP_006635331.1 | Paenibacillus zanthoxyli | WP_025690613.1 |

Fig. 15 continued

| Microorganism | Genbank Accession | Microorganism | Genbank Accession |
| --- | --- | --- | --- |
| Pseudomonas sp. GM60 | WP_008035544.1 | Labrenzia sp. CP4 | WP_062491890.1 |
| Pedobacter sp. Hv1 | WP_055131283.1 | Labrenzia | WP_031269713.1 |
| Serratia plymuthica | WP_006316853.1 | Novosphingobium barchaimii | WP_058735897.1 |
| Serratia | WP_037395580.1 | Xenophilus azovorans | WP_038209862.1 |
| Pseudomonas sp. GM80 | WP_008085601.1 | Dysgonomonas capnocytophagoides | WP_026625288.1 |
| Serratia sp. C-1 | WP_062789569.1 | Caulobacter sp. Root656 | WP_057183767.1 |
| Pseudomonas sp. 45MFCol3.1 | WP_019648555.1 | Thermopetrobacter sp. TC1 | WP_038034810.1 |
| Pseudomonas sp. GM48 | WP_007992678.1 | Thalassospira lucentensis | WP_022734083.1 |
| Pseudomonas sp. GM18 | WP_007937000.1 | Arthrobacter sp. H14 | WP_026535687.1 |
| Synechocystis sp. PCC 7509 | WP_028954191.1 | Brevundimonas abyssalis | WP_021697031.1 |
| Pseudomonas sp. QTF5 | WP_030131028.1 | Parvularcula oceani | WP_031555700.1 |
| bacterium UASB14 | WP_045505933.1 | Blastomonas sp. AAP53 | WP_017670274.1 |
| Pseudomonas sp. GM79 | WP_008074041.1 | Labrenzia alexandrii | WP_055672130.1 |
| Pseudomonas sp. CF161 | WP_043230378.1 | Pseudomonas deceptionensis | WP_048359292.1 |
| Alcanivorax | WP_063521418.1 | Type-D symbiont of Plautia stali | WP_058970253.1 |
| Pseudomonas sp. Root329 | WP_056741929.1 | Erythrobacter | WP_050600626.1 |
| Gilliamella apicola | WP_034883414.1 | Paludibacterium yongneupense | WP_051229471.1 |
| Pseudomonas sp. GM49 | WP_007993749.1 | Caulobacter sp. Root1472 | WP_056761772.1 |
| Aquabacterium parvum | WP_058086343.1 | Ensifer adhaerens | WP_053248748.1 |
| Acidithiobacillus thiooxidans | WP_024893728.1 | Sphingomonas sp. 35-24ZXX | WP_033923881.1 |
| Pseudomonas sp. GM41(2012) | WP_008154661.1 | Achromobacter sp. RTa | WP_043546625.1 |
| Pseudomonas brassicacearum | WP_025213967.1 | Pseudorhodobacter wandonensis | WP_050522986.1 |
| Leptolyngbya boryana | WP_017288016.1 | Aphanizomenon flos-aquae | WP_039203516.1 |
| Pseudomonas sp. 11/12A | WP_047527806.1 | Sphingomonas endophytica | WP_058756259.1 |
| Pseudomonas sp. GM102 | WP_007905729.1 | Devosia sp. A16 | WP_055048936.1 |
| Candidatus Solibacter usitatus | WP_011686428.1 | Rhizobium sp. Root483D2 | WP_060636130.1 |
| Myxosarcina sp. GI1 | WP_036484294.1 | Ensifer sp. WSM1721 | WP_026622024.1 |
| Alcanivorax sp. 19-m-6 | WP_035233016.1 | Enterobacter cancerogenus | WP_034824240.1 |
| Pseudomonas sp. GM50 | WP_008008459.1 | Cystobacter fuscus | WP_002621816.1 |

Fig. 15 continued

| Microorganism | Genbank Accession | Microorganism | Genbank Accession |
|---|---|---|---|
| Acaryochloris sp. CCMEE 5410 | WP_010467794.1 | Sphingomonas sp. Y57 | WP_047167465.1 |
| Pseudomonas sp. G5(2012) | WP_020800719.1 | Sinorhizobium sp. PC2 | WP_046119906.1 |
| Acaryochloris marina | WP_012162817.1 | Sphingomonas jaspsi | WP_037503921.1 |
| Pseudoalteromonas | WP_042149186.1 | Thalassospira sp. MCCC 1A01148 | WP_062953912.1 |
| Pantoea sp. A4 | WP_026042421.1 | Ensifer sp. TW10 | WP_026613300.1 |
| Alcanivorax jadensis | WP_035250216.1 | Fulvimarina pelagi | WP_040488894.1 |
| Bacteria | WP_009562838.1 | Rhizobium sp. CF097 | WP_037119901.1 |
| Pseudomonas sp. RIT-PI-q | WP_059404196.1 | Pseudarthrobacter chlorophenolicus | WP_015937239.1 |
| Serratia grimesii | WP_037426347.1 | Devosia | WP_055878182.1 |
| Scytonema millei | WP_039714778.1 | Coccidioides immitis RS | XP_001248209.2 |
| Calothrix sp. 336/3 | WP_035158367.1 | Blastomonas sp. AAP25 | WP_054134089.1 |
| Chroococcidiopsis thermalis | WP_015152152.1 | Sphingomonas sp. Ag1 | WP_046409195.1 |
| beta proteobacterium L13 | WP_017510054.1 | Oceanicaulis sp. HL-87 | WP_036514352.1 |
| Alcanivorax sp. HI0083 | WP_063518558.1 | Penicillium digitatum Pd1 | XP_014534104.1 |
| Pseudopedobacter saltans | WP_013633880.1 | Maritalea myrionectae | WP_027835180.1 |
| Pseudomonas gingeri | WP_017124151.1 | Sinorhizobium sp. GL28 | WP_058323580.1 |
| Vogesella sp. EB | WP_047967847.1 | Erythrobacter sp. SD-21 | WP_006832002.1 |
| Clostridiales bacterium VE202-28 | WP_025484850.1 | Sinorhizobium/Ensifer group | WP_057248140.1 |
| Cellvibrio sp. BR | WP_007642494.1 | Afifella pfennigii | WP_051631353.1 |
| Hungatella hathewayi | WP_039892287.1 | Croceicoccus naphthovorans | WP_047820461.1 |
| Tatumella sp. UCD-D_suzukii | WP_025903659.1 | Arthrobacter nitrophenolicus | WP_035752355.1 |
| Tatumella ptyseos | WP_029990876.1 | Sphingomonas | WP_056359867.1 |
| Niabella aurantiaca | WP_018629826.1 | Thalassospira | WP_037991166.1 |
| Lachnoclostridium | WP_024296203.1 | Anabaena cylindrica | WP_015215725.1 |
| Draconibacterium sediminis | WP_045033031.1 | Corynebacterium halotolerans | WP_048742456.1 |
| Desulfovibrio frigidus | WP_031479260.1 | Ensifer sp. ZNC0028 | WP_043613157.1 |
| Acinetobacter brisouii | WP_004902992.1 | Brevundimonas sp. Leaf363 | WP_056103760.1 |
| Pseudorhodobacter aquimaris | WP_050528496.1 | Serratia fonticola | WP_024485202.1 |

Fig. 15 continued

| Microorganism | Genbank Accession | Microorganism | Genbank Accession |
|---|---|---|---|
| Rubrobacter aplysinae | WP_047866623.1 | Altererythrobacter epoxidivorans | WP_061923692.1 |
| Acinetobacter sp. ANC 3789 | WP_004749213.1 | alpha proteobacterium JLT2015 | WP_038280972.1 |
| Tatumella morbirosei | WP_038017563.1 | Arthrobacter sp. Leaf137 | WP_056079511.1 |
| Altererythrobacter troitsensis | WP_057882776.1 | Sphingomonas sp. Root710 | WP_056378476.1 |
| Dinoroseobacter shibae | WP_012177956.1 | Sphingomonas wittichii | WP_037526704.1 |
| Loktanella vestfoldensis | WP_026352351.1 | Corynebacterium freneyi | WP_052054332.1 |
| Sphingopyxis | WP_003044487.1 | Sphingomonas sp. SRS2 | WP_046195859.1 |
| Acinetobacter | WP_005173592.1 | Porphyrobacter sp. AAP82 | WP_017664013.1 |
| Sediminimonas qiaohouensis | WP_026756407.1 | Agaricus bisporus var. bisporus H97 | XP_006455303.1 |
| [Clostridium clariflavum | WP_014254971.1 | Agaricus bisporus var. burnettii JB137-S8 | XP_007330894.1 |
| uncultured Sulfuricurvum sp. RIFRC-1 | WP_015653945.1 | Erythrobacter vulgaris | WP_040963667.1 |
| Lysinibacillus macroides | WP_053993407.1 | Sphingomonas sp. Leaf231 | WP_056631646.1 |
| Dysgonomonas sp. HGC4 | WP_050708384.1 | Cucumibacter marinus | WP_029039849.1 |
| Leisingera sp. ANG-M7 | WP_039183947.1 | alpha proteobacterium Mf 1.05b.01 | WP_029638849.1 |
| Sphingopyxis sp. A083 | WP_058811316.1 | Brevundimonas sp. Leaf280 | WP_055755221.1 |
| Clostridium sp. DL-VIII | WP_009170495.1 | Sinorhizobium | WP_011974380.1 |
| Lactococcus raffinolactis | WP_061774007.1 | Arthrobacter enclensis | WP_058267449.1 |
| Acinetobacter lwoffii | WP_004280839.1 | Nocardia otitidiscaviarum | WP_039817058.1 |
| Leisingera | WP_019294976.1 | Citromicrobium | WP_010237878.1 |
| Pantoea anthophila | WP_046102129.1 | Rhizobium sp. OK665 | WP_037105052.1 |
| Pseudorhodobacter antarcticus | WP_050519835.1 | Rhizobium sp. Root482 | WP_056330571.1 |
| Kaistia granuli | WP_018185327.1 | Litoreibacter arenae | WP_021100138.1 |
| Bradyrhizobium elkanii | WP_051003151.1 | Bradyrhizobium tropiciagri | WP_050420370.1 |
| Aquabacterium sp. NJ1 | WP_052162578.1 | Pseudomonas psychrotolerans | WP_058768510.1 |
| Halothiobacillus neapolitanus | WP_012824911.1 | Erythrobacter litoralis | WP_011414053.1 |
| Dysgonomonas gadei | WP_006801167.1 | Oceanicaulis alexandrii | WP_022700009.1 |
| Type-F symbiont of Plautia stali | WP_058957646.1 | Phaeobacter | WP_040172007.1 |
| Roseibium sp. TrichSKD4 | WP_009758811.1 | | |

Fig. 15 continued

| Microorganism | Genbank Accession | Microorganism | Genbank Accession |
|---|---|---|---|
| Leisingera sp. ANG-M6 | WP_039194316.1 | Labrenzia alba | WP_055675296.1 |
| Bradyrhizobium viridifuturi | WP_050629432.1 | Pseudomonas stutzeri | WP_045164245.1 |
| Acinetobacter gerneri | WP_004870294.1 | Brevundimonas naejangsanensis | WP_024353237.1 |
| Acinetobacter sp. HR7 | WP_034585714.1 | Rhizobium sp. Leaf371 | WP_062595152.1 |
| Kaistia adipata | WP_029075359.1 | Pseudomonas nitroreducens | WP_024762244.1 |
| Pantoea sp. Sc1 | WP_009089455.1 | Sphingopyxis alaskensis | WP_041383077.1 |
| Sphingopyxis terrae | WP_062902254.1 | Phaeospirillum fulvum | WP_051185933.1 |
| Bradyrhizobium embrapense | WP_050400635.1 | Raoultella ornithinolytica | WP_041145659.1 |
| Raoultella terrigena | WP_045858268.1 | Ruegeria sp. TM1040 | WP_011539677.1 |
| Sinorhizobium americanum | WP_037378402.1 | Shinella sp. DD12 | WP_023515461.1 |
| Leisingera sp. ANG-Vp | WP_039134607.1 | | |
| Erythrobacter sp. JL475 | WP_034954745.1 | | |

Fig. 15 continued

GENETICALLY ENGINEERED MICROORGANISMS FOR THE PRODUCTION OF CHORISMATE-DERIVED PRODUCTS

CROSS REFERENCE TO RELATED APPLICATIONS

This application claims the benefit of U.S. Provisional Patent Application No. 62/167,101 filed May 27, 2015, the entirety of which is incorporated herein by reference.

FIELD OF THE INVENTION

The present invention relates to genetically engineered microorganisms and methods for the production of chorismate-derived products by microbial fermentation, particularly by microbial fermentation of a gaseous substrate.

BACKGROUND OF THE INVENTION

The current generation of biologically-produced commodity chemicals that use either food or non-food crops to produce sugar or cellulose-based feedstocks have drawbacks relating to land use, food security, supply volatility, and environmental issues.

It has long been recognized that catalytic processes may be used to convert gases containing carbon monoxide (CO) and/or carbon dioxide ($CO_2$) and hydrogen ($H_2$) into a variety of fuels and chemicals. However, microorganisms may also be used to biologically convert such gases into fuels and chemicals. Biological processes have several advantages over catalytic processes, including higher specificity, higher yields, lower energy costs, and greater catalyst resistance to poisoning.

CO is a major free energy-rich byproduct of the incomplete combustion of organic materials such as coal or oil and oil-derived products. For example, the steel industry in Australia is reported to produce and release into the atmosphere over 500,000 tonnes of CO annually.

The ability of microorganisms to grow on CO as a sole carbon source was first discovered in 1903. This was later determined to be a property of microorganisms that use the acetyl coenzyme A (acetyl-CoA) biochemical pathway of autotrophic growth, also known as the Wood-Ljungdahl pathway. A large number of anaerobic microorganisms including carboxydotrophic, photosynthetic, methanogenic, and acetogenic microorganisms have been shown to metabolize CO to various end products, namely $CO_2$, $H_2$, methane, n-butanol, acetate, and ethanol.

The aromatic compound para-hydroxybenzoic acid (pHBA) is a major monomer used in liquid crystal polymers and also used as a precursor for the production of parahydroxybenzoates or parahydroxybenzoic esters, commonly referred to as parabens. Liquid crystal polymers include Kevlar and Vectran, which have multiple uses. Parabens and their salts are used in a range of industries including the cosmetic, pharmaceutical and food industries. They are effective preservatives and can be used for their bactericidal and fungicidal properties in cosmetic and food formulations.

Accordingly, there remains a need for additional microorganisms and methods for producing pHBA and other high-value chorismate-derived products.

SUMMARY OF THE INVENTION

The invention provides a genetically engineered microorganism capable of producing chorismate-derived products. In particular, the invention provides a genetically engineered microorganism capable of producing at least one chorismate-derived product, wherein the bacterium comprises at least one of (a) an exogenous chorismate pyruvate lyase (EC 4.1.3.40), (b) an exogenous isochorismate synthase (EC 5.4.4.2), (c) an exogenous isochorismate pyruvate lyase (EC 4.2.99.21), and (d) a prephenate synthase (EC 5.4.99.5) comprising a disruptive mutation. In particular embodiments, the genetically engineered microorganism is a C1-fixing bacterium, such as a *Clostridium* bacterium, capable of producing at least one chorismate-derived product by fermentation of a C1-containing gaseous substrate.

For example, the chorismate pyruvate lyase may be ubiC, the isochorismate synthase may be pchA, the isochorismate pyruvate lyase may be pchB, and the prephenate synthase may be pheA. The disruptive mutation in prephenate synthase may reduce or eliminate the expression or activity of the prephenate synthase. Such a disruptive mutation may yield a bacterium that produces a reduced amount of prephenate or prephenate-derived products compared to a parental bacterium and/or a bacterium that produces substantially no tyrosine or phenylalanine.

The microorganism of the invention may comprise at least one nucleic acid encoding at least one of (a) the exogenous chorismate pyruvate lyase, (b) the exogenous isochorismate synthase, (c) the exogenous isochorismate pyruvate lyase, and (d) the prephenate synthase comprising a disruptive mutation. In certain embodiments, the nucleic acid is codon optimized for expression in *Clostridium*.

The chorismate-derived product may be any product produced directly or indirectly from chorismate. In particular, the chorismate-derived product may comprise a 6-membered carbon ring, for example, a benzene or cyclohexane ring, substituted with a carboxyl group or carboxylate anion and further substituted with one or more OH groups and/or one or more $NH_2$ groups. Chorismate-derived products include, but are not limited to, para-hydroxybenzoic acid, salicylate, 2-aminobenzoate, dihydroxybenzoate, and 4-hydroxycyclohexane carboxylic acid.

In one embodiment, the microorganism of the invention expresses a chorismate pyruvate lyase of ubiC and produces a chorismate-derived product of para-hydroxybenzoic acid. In one embodiment the microorganism of the invention further expresses feedback-insensitive DAHP synthase.

In one embodiment, the microorganism of the invention expresses an isochorismate synthase of pchA and an isochorismate pyruvate lyase of pchB and produces a chorismate-derived product of salicylate. In one embodiment the microorganism of the invention further expresses feedback-insensitive DAHP synthase.

In one embodiment, the microorganism of the invention comprises a prephenate synthase comprising a disruptive mutation and produces a one or more of chorismate-derived product of 2-aminobenzoate, 2,3-dihydroxybenzoate, 3,4-dihydroxybenzoate and 4-hydroxycyclohexane carboxylic acid.

In one embodiment, the microorganism of the invention produces at least one chorismate-derived product not produced by a parental microorganism or a greater amount of at least one chorismate-derived product than a parental microorganism.

In one embodiment, the bacterium of the invention is derived from a C1-fixing parental bacterium. In a preferred embodiment, the bacterium of the invention is derived from a parental bacterium selected from the group consisting of *Clostridium autoethanogenum*, *Clostridium ljungdahlii*, and *Clostridium ragsdalei*. In a particularly preferred embodiment, the bacterium of the invention is derived from a parental bacterium of *Clostridium autoethanogenum* deposited under DSMZ accession number DSM23693.

The invention further provides a method of producing a fermentation product, comprising fermenting the microorganism of the invention in the presence of a C1-containing gaseous substrate. Generally, the fermentation product is a chorismate-derived product. In a preferred embodiment, the gaseous substrate comprises at least one C1 carbon source.

BRIEF DESCRIPTION OF THE DRAWINGS

FIG. 9a shows quantification of pHBA detected in each sample at 24, 96, 144, and 192 hour time points. Three replicate cultures were sampled for the negative control strain (*C. autoethanogenum* LZ1561) and the two biological replicates of *C. autoethanogenum* LZ1561 carrying pARO_01. FIG. 9b shows mean of n=3 technical replicates ±1 SD.

FIG. 13 is a table identifying exemplary sources of chorismate pyruvate lyase (EC 4.1.3.40).

FIG. 14 is a table identifying exemplary sources of isochorismate synthase (EC 5.4.4.2).

FIG. 15 is table of identifying exemplary sources of isochorismate pyruvate lyase (EC 4.2.99.21).

DETAILED DESCRIPTION OF THE INVENTION

Figure 1:
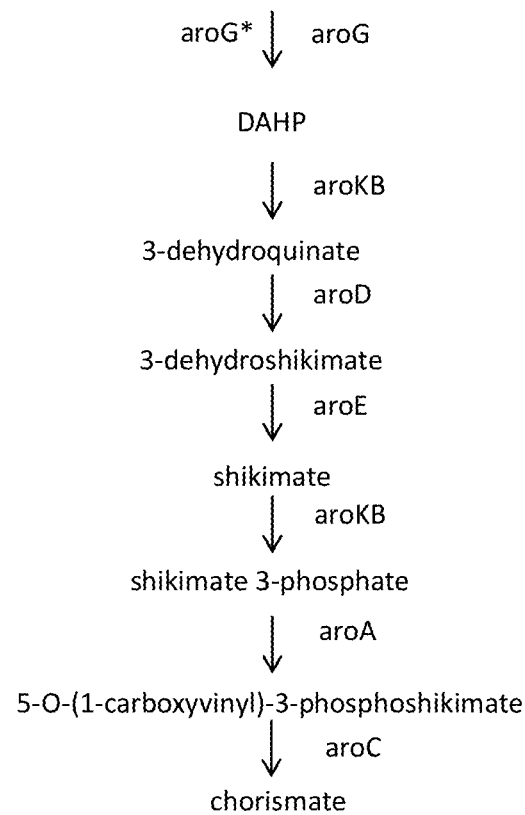
FIG. 1 is a diagram showing production of chorismate via a native shikimate pathway in Clostridia.

Clostridia natively produce chorismate, which serves as a precursor to the aromatic amino acids tryptophan, tyrosine, and phenylalanine, from phosphoenolpyruvate and erythrose-4-phosphate via the shikimate pathway (FIG. 1). This pathway is described in detail in Bentley, *Crit Rev Biochem Mol Biol*, 25.5: 307-384, 1990. The invention provides a genetically engineered bacterium capable of producing at least one chorismate-derived product by fermentation of a gaseous substrate.

The inventors have demonstrated that chorismate-derived products can be sustainably produced and recovered from a C1-carbon source. The invention provides a method of producing at least one chorismate-derived product using a C1-containing gaseous substrate as the main carbon and energy source. In this way, the present invention has a number of advantages over processes that rely on sugar- or cellulose-based substrates. For example, sugar- or cellulose-based substrates are typically also useful for food (e.g. sugar cane) and their intensive land use has negative environmental consequences. Further, the invention provides an alternative method for the production of chorismate-derived products, optionally via the use of waste gases (e.g. CO from industrial processes). Thus, the invention provides a source of revenue from waste gases and, furthermore, captures the carbon in those waste gases to reduce the carbon emissions that would occur if the gases were flared to the atmosphere.

Heterotrophic microorganisms such as *E. coli* and *S. cerevisiae* produce relatively high levels of ATP through glycolysis. In contrast, microorganisms which use C1-carbon sources (e.g., CO or $CO_2$) have poor ATP availability. For example, analysis of the reaction kinetics in a typical carboxydotrophic microorganism *C. autoethanogenum* gives a predicted ATP yield when producing pHBA, a chorismate-derived product) of −0.4 ATP per mol of CO fixed. As such, it would not be expected that any pHBA would be produced due to the energy constraints. Similarly it would not be expected that other chorismate-derived products would be produced by a carboxydotrophic microorganism due to the metabolic burden of producing such compounds under autotrophic conditions. The inventors have surprisingly shown however that a number of chorismate-derived products can be produced from a gaseous substrate. Further, said products can be produced from industrial waste gases which provide practical, economic, and environmental benefits over other substrates.

In particular, the invention provides genetically engineered microorganisms capable of producing at least one chorismate-derived product by introducing at least one of (a) a nucleic acid encoding an exogenous chorismate pyruvate lyase, (b) a nucleic acid encoding an exogenous isochorismate synthase (a.k.a., isochorismate mutase), (c) a nucleic acid encoding an exogenous isochorismate pyruvate lyase, and (d) a nucleic acid encoding a prephenate synthase comprising a disruptive mutation. In a preferred embodiment, the genetically engineered microorganism is a C1-fixing bacterium capable of producing at least one chorismate-derived product by fermentation of a gaseous substrate. In preferred embodiments the C1-fixing bacterium is a *Clostridium* bacterium.

A "chorismate-derived product" or "product derived from chorismate" or similar terms encompass products produced directly or indirectly from chorismate (or chorismic acid). Chorismate-derived products typically comprise a 6-membered carbon ring, for example, a benzene or cyclohexane ring, substituted with a carboxyl group or carboxylate anion and further substituted with one or more OH groups and/or one or more NH2 groups. Specifically, chorismate-derived products include, but are not limited to, para-hydroxybenzoic acid, salicylate, 2-aminobenzoate, 2,3-dihydroxybenzoate, 3,4-dihydroxybenzoate, and 4-hydroxycyclohexane carboxylic acid.

The microorganism of the invention may comprise an exogenous chorismate pyruvate lyase enzyme (EC 4.1.3.40) that catalyzes the conversion of chorismate to para-hydroxybenzoic acid and pyruvate in the first committed step of ubiquinone biosynthesis. The enzyme may be derived from any microorganism having such an enzyme. The enzyme may be a UbiC enzyme. The UbiC enzyme may be derived from *Escherichia coli, Klebsiella oxytoca, Citrobacter freundii*, or any other microorganism having a UbiC enzyme. In one embodiment, the UbiC enzyme is derived from *Escherichia coli* and comprises SEQ ID NO: 1 or a functionally equivalent variant thereof.

Similarly, the microorganism of the invention may comprise a nucleic acid encoding an exogenous chorismate pyruvate lyase. The nucleic acid may be a chorismate pyruvate lyase gene derived from any microorganism having such a gene. The chorismate pyruvate lyase gene may be a ubiC gene. The ubiC gene may be derived from *Escherichia coli, Klebsiella oxytoca, Citrobacter freundii*, or any other microorganism having a ubiC gene. In one embodiment, the ubiC gene is derived from *Escherichia coli* and comprises SEQ ID NO: 2 or a codon-optimized or functionally equivalent variant thereof.

The UbiC enzyme or ubiC gene may also be modified (e.g., mutated) to enhance solubility, stability, or other gene/enzyme properties. Such modifications may result in increased product titers. Example 4 describes an experimental protocol to engineer a UbiC enzyme to decrease product inhibition through retention of para-hydroxybenzoic acid. One particular modification involves engineering the ubiC gene to express a UbiC enzyme with two surface-active serines instead of cysteines. The serine residues result in less protein aggregation and, in turn, improved solubility. Accordingly, in a particular embodiment, the UbiC enzyme comprises a mutation to replace at least one surface-active cysteine with a serine.

In alternative embodiments, the chorismate pyruvate lyase (EC 4.1.3.40) may be or may be derived, for example, from any of the sources identified in FIG. 13.

Figure 2:
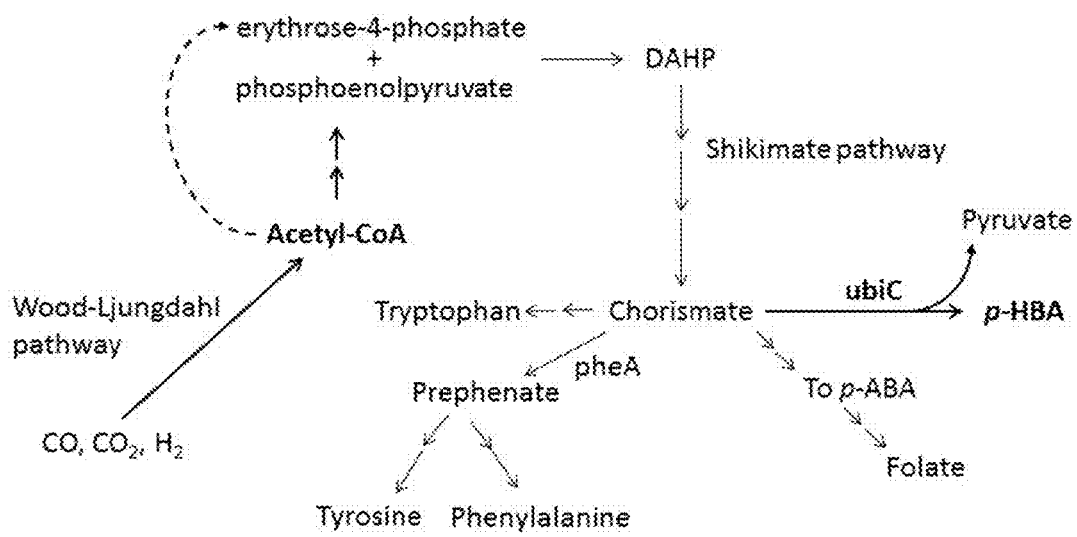
FIG. 2 is a diagram showing the pathway for production of pHBA in a genetically engineered *Clostridium* bacterium.

Introduction of an exogenous chorismate pyruvate lyase (e.g., ubiC) or a nucleic acid encoding an exogenous chorismate pyruvate lyase (e.g., ubiC) results in production of para-hydroxybenzoic acid, a chorismate-derived product, by the microorganism of the invention. The production of para-hydroxybenzoic acid is illustrated in FIG. 2. C1 fixing bacteria including the species *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kivui*, do not natively produce para-hydroxybenzoic acid. In fact, since ubiquinone is generally only produced in aerobically respiring microorganisms, chorismate pyruvate lyase is not typically found in carboxydotrophic microorganisms. Although it may be expected that the diversion of chorismate to produce pHBA instead of amino acids would have detrimental effects on the growth or survival of the microorganism, the inventors have shown that the microorganism is not affected to a degree that significantly compromises survival and growth under standard conditions.

Para-hydroxybenzoic acid may also be referred to, for example, as pHBA, 4-hydroxybenzoic acid, p-hydroxybenzoic acid, or para-hydroxybenzoate. References to any of these terms, as used herein, encompass both the acid and anion forms of the molecule.

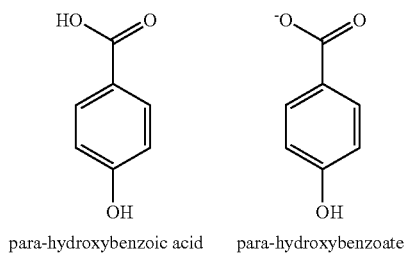

para-hydroxybenzoic acid     para-hydroxybenzoate

The microorganism of the invention may comprise an exogenous isochorismate synthase enzyme, also referred to as isochorismate mutase, (EC 5.4.4.2) that catalyzes the conversion of chorismate to isochorismate. The enzyme may be derived from any microorganism having such an enzyme. The enzyme may be a PchA enzyme. The PchA enzyme may be derived from *Pseudomonas aeruginosa* or any other microorganism having a PchA enzyme. In one embodiment, the PchA enzyme is derived from *Pseudomonas aeruginosa* and comprises SEQ ID NO: 3 or a functionally equivalent variant thereof.

Similarly, the microorganism of the invention may comprise a nucleic acid encoding an exogenous isochorismate synthase. The nucleic acid may be an isochorismate synthase gene derived from any microorganism having such a gene. The isochorismate synthase gene may be a pchA gene. The pchA gene may be derived from *Pseudomonas aeruginosa* or any other microorganism having a pchA gene. In one embodiment, the pchA gene is derived from *Pseudomonas aeruginosa* and comprises SEQ ID NO: 4 or a codon-optimized or functionally equivalent variant thereof.

In alternative embodiments, the isochorismate synthase (EC 5.4.4.2) may be or may be derived, for example, from any of the sources identified in FIG. 14.

The microorganism of the invention may comprise an exogenous isochorismate pyruvate lyase enzyme (EC 4.2.99.21) that catalyzes the conversion of isochorismate to salicylate and pyruvate. The enzyme may be derived from any microorganism having such an enzyme. The enzyme may be a PchB enzyme. The PchB enzyme may be derived from *Pseudomonas aeruginosa* or any other microorganism having a PchB enzyme. In one embodiment, the PchB enzyme is derived from *Pseudomonas aeruginosa* and comprises SEQ ID NO: 5 or a functionally equivalent variant thereof.

Similarly, the microorganism of the invention may comprise a nucleic acid encoding an exogenous isochorismate pyruvate lyase. The nucleic acid may be an isochorismate pyruvate lyase gene derived from any microorganism having such a gene. The isochorismate pyruvate lyase gene may be a pchB gene. The pchB gene may be derived from *Pseudomonas aeruginosa* or any other microorganism having a pchB gene. In one embodiment, the pchB gene is derived from *Pseudomonas aeruginosa* and comprises SEQ ID NO: 6 or a codon-optimized or functionally equivalent variant thereof.

In alternative embodiments, the isochorismate pyruvate lyase (EC 4.2.99.21) may be or may be derived, for example, from any of the sources identified in FIG. 15.

Figure 3:
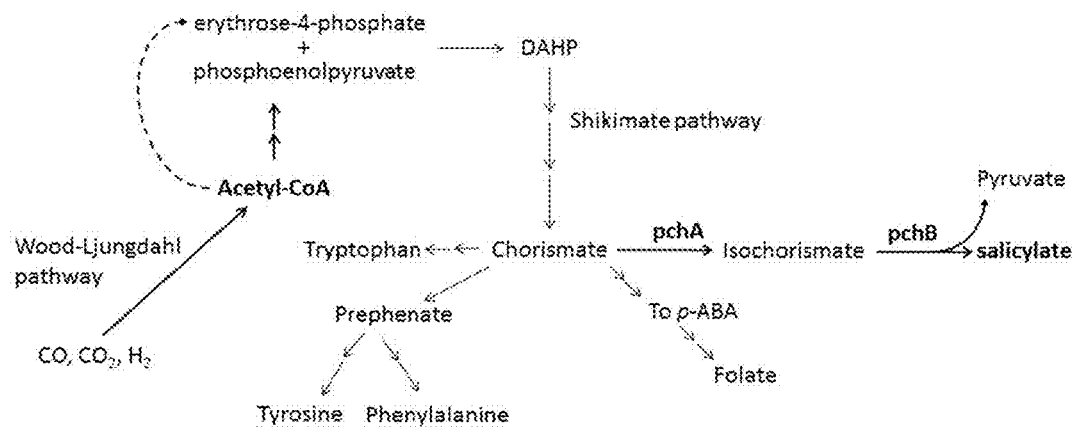
FIG. 3 is a diagram showing the pathway for production of salicylate in a genetically engineered *Clostridium* bacterium.

Introduction of (1) an exogenous isochorismate synthase (e.g., pchA) and (2) an exogenous isochorismate pyruvate lyase (e.g., pchB) results in production of salicylate, a chorismate-derived product, by the microorganism of the invention. The production of salicylate is illustrated in FIG. 3, whereby chorismate is converted to isochorismate by isochorismate synthase and then further converted to salicylate and pyruvate by isochorismate pyruvate lyase. C1 fixing bacteria including the species *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kivui*, do not natively produce salicylate.

Salicylate may also be referred to, for example, as 2-hydroxybenzoate, salicylic acid, or 2-hydroxybenzoic acid. References to any of these terms, as used herein, encompass both the acid and anion forms of the molecule.

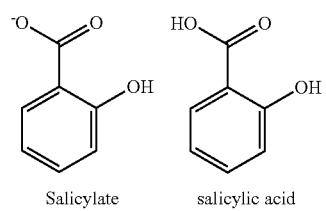

Salicylate     salicylic acid (d) Prephenate Synthase Comprising a Disruptive Mutation The microorganism of the invention may comprise a prephenate synthase enzyme (EC 5.4.99.5) comprising a disruptive mutation. Prephenate synthase typically catalyzes the conversion of chorismate to prephenate (i.e., a chorismate↔prephenate mutase reaction). Accordingly, a prephenate synthase enzyme comprising a disruptive mutation is unable or less able to catalyze the conversion of chorismate to prephenate. The prephenate synthase comprising a disruptive mutation may be pheA comprising a disruptive mutation. The prephenate synthase may also be referred to as chorismate mutase.

In some embodiments, the pheA may be a bifunctional enzyme that carries out both prephenate synthase (i.e., chorismate mutase) (EC 5.4.99.5) and prephenate dehydratase (EC 4.2.1.51) reactions. In microorganisms where these two reactions are carried out by separate enzymes, knocking out EC 5.4.99.5 activity will result in significantly decreased or eliminated production of prephenate or compounds downstream of prephenate, while knocking out EC 4.2.1.51 activity alone would not achieve the same phenotype, since prephenate may still be produced. In one embodiment, the pheA is derived from *Clostridium autoethanogenum* and comprises SEQ ID NO: 11 or a functionally equivalent variant thereof.

Similarly, the microorganism of the invention may comprise a nucleic acid encoding a prephenate synthase comprising a disruptive mutation. The nucleic acid may be a pheA gene comprising a disruptive mutation. In one embodiment, the disruptive mutation is a knockout mutation of a pheA gene. In one embodiment, the pheA gene is derived from *Clostridium autoethanogenum* and comprises SEQ ID NO: 10 or a codon-optimized or functionally equivalent variant thereof.

Disrupting prephenate synthase results in reduced or eliminated production of phenylalanine and tyrosine. Surprisingly, disrupting prephenate synthase also results in the production of additional products that are not typically produced or that are produced only at very low levels.

Figure 4:
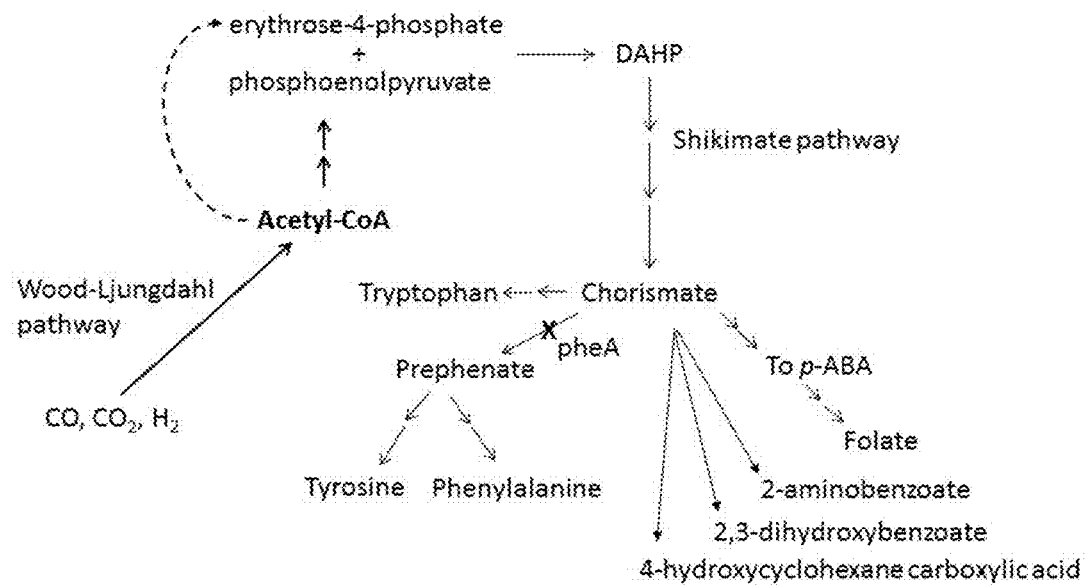
FIG. 4 is a diagram showing the pathway for production of aromatic products in a genetically engineered *Clostridium* bacterium comprising a disruptive mutation in a nucleic acid encoding pheA.

In particular, the introduction of a disruptive mutation to prephenate synthase (e.g., pheA) or a nucleic acid encoding prephenate synthase (e.g., pheA) results in production of one or more of 2-aminobenzoate, dihydroxybenzoate, and 4-hydroxycyclohexane carboxylic acid, all chorismate-derived products, by the microorganism of the invention. The production pathways of these products is illustrated in FIG. 4. Many microorganisms, including species of Clostridia such as *Clostridium autoethanogenum, Clostridium ljungdahlii*, and *Clostridium ragsdalei*, do not natively produce these products or only produce very low levels of these products.

Exemplary sources for pheA are provided. However, it should be appreciated that other suitable sources for pheA may be available The prephenate dehydratase be or may be derived, for example, from any of the following sources, the sequences of which are publically available:

| Description | Microorganism | Genbank accession |
| --- | --- | --- |
| bifunctional chorismate mutase/ prephenate dehydratase | *Acetobacterium woodii* | AFA49374.1 |
| prephenate dehydratase | *Blautia producta* | WP_033143345.1 |
| prephenate dehydratase | *Clostridium aceticum* | WP_044823168.1 |
| prephenate dehydratase | *Clostridium autoethanogenum* | AGY75132.1 |
| bifunctional chorismate mutase/ prephenate dehydratase | *Clostridium carboxidivorans* | WP_007060905.1 |
| bifunctional chorismate mutase/ prephenate dehydratase | *Clostridium coskatii* | WP_063600678.1 |
| bifunctional chorismate mutase/ prephenate dehydratase | *Clostridium drakei* | WP_032076381.1 |

| Description | Microorganism | Genbank accession |
| --- | --- | --- |
| bifunctional chorismate mutase/ prephenate dehydratase | *Clostridium ljungdahlii* | WP_063554005.1 |
| prephenate dehydratase | *Clostridium magnum* | KZL89370.1 |
| bifunctional chorismate mutase/ prephenate dehydratase | *Clostridium scatologenes* | WP_029159263.1 |
| chorismate mutase | *Eubacterium limosum* | WP_058695931.1 |
| chorismate mutase | *Oxobacter pfennigii* | WP_054874911.1 |
| prephenate dehydratase | *Sporomusa ovata* | EQB25731.1 |
| prephenate dehydratase | *Thermoanaerobacter kivui* | WP_049685038.1 |

2-aminobenzoate may also be referred to, for example, as 2-aminobenzoic acid, o-aminobenzoic acid, anthranilic acid, anthranilate, or vitamin L1. References to any of these terms, as used herein, encompass both the acid and anion forms of the molecule.

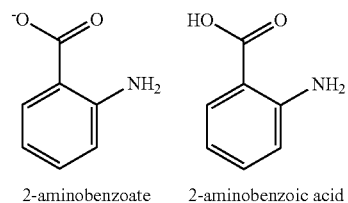

2-aminobenzoate     2-aminobenzoic acid

Dihydroxybenzoate may be referred to, for example, as 2,3-dihydroxybenzoate, 2,3-dihydroxybenzoic acid, 3,4-dihydroxybenzoate, 3,4-dihydroxybenzoic acid or Protocatechuic acid. References to any of these terms, as used herein, encompass both the acid and anion forms of the molecule.

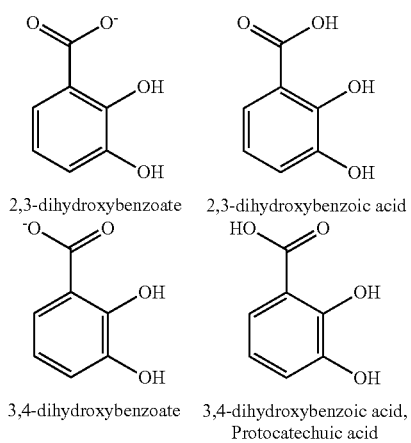

2,3-dihydroxybenzoate    2,3-dihydroxybenzoic acid 3,4-dihydroxybenzoate    3,4-dihydroxybenzoic acid, Protocatechuic acid 4-hydroxycyclohexane carboxylic acid may also be referred to, for example, as cis-4-hydroxycyclohexane carboxylic acid or 4-hydroxycyclohexane-1-carboxylate. References to any of these terms, as used herein, encompass both the acid and anion forms of the molecule.

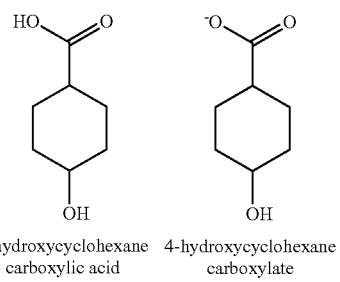

4-hydroxycyclohexane carboxylic acid    4-hydroxycyclohexane carboxylate

In another embodiment, the microorganism of the invention further comprises a nucleic acid encoding a feedback-insensitive DAHP synthase DAHP synthase catalyses the first committed step in the shikimate pathway (FIG. 1) in which erythrose-4-phosphate and phosphoenolpyruvate are converted to 3-deoxy-D-arabinoheptosonate-7-phosphate. The inventors believe that this step in the pathway is subject to feedback inhibition by aromatic amino acids (tryptophan, phenylalanine, tyrosine) as described for *E. coli* (Hu et al. J. Basic Microbiol. 2003, 43:399-406). Accordingly, the inventors have, based on this prior art, developed a feedback-insensitive DAHP synthase, which is believed to reduce the risk of flux to chorismate-derived products being reduced by this feedback inhibition. Nucleic acids encoding appropriate DAHP synthases are known to those of skill in the art. However, by way of example, the nucleic acid encoding a DAHP synthase may be derived from *Escherichia coli*, *Clostridium beijerinckii*, or *Saccharomyces cerevisiae*. In one embodiment, the DAHP synthase may be feedback-insensitive DAHP synthase from *Escherichia coli*, having the nucleic acid sequence of SEQ ID NO: 7 and the amino acid sequence of SEQ ID NO: 8. The feedback-insensitive DAHP synthase may be introduced on the same vector as a gene encoding one of the aforementioned enzymes or on a different vector. The feedback-insensitive DAHP synthase may have its own promoter or may follow the promoter for one of the aforementioned enzymes in a bicistronic arrangement, wherein a single promoter drives the transcription of a single mRNA that encodes both the enzyme and the feedback-insensitive DAHP synthase.

In one embodiment, the microorganism of the invention comprises an exogenous chorismate pyruvate lyase enzyme (EC 4.1.3.40), and an exogenous feedback-insensitive DAHP synthase. In particular embodiments the microorganism comprises an exogenous UbiC enzyme, and an exogenous feedback-insensitive DAHP synthase. In a specific embodiment, the invention comprises exogenous ubiC gene having the nucleic acid sequence of SEQ ID NO: 1, and an exogenous feedback-insensitive DAHP synthase having the nucleic acid sequence of SEQ ID NO: 7. In one embodiment, the microorganism comprising both an exogenous chorismate pyruvate lyase enzyme and an exogenous feedback-insensitive DAHP synthase demonstrates greater production of para-hydroxybenzoic acid compared to a microorganism without a feedback-insensitive DAHP synthase.

Similarly, the microorganism of the invention may comprise a nucleic acid encoding both an exogenous chorismate pyruvate lyase and feedback-insensitive DAHP synthase.

In one embodiment, the microorganism of the invention comprises (i) an exogenous isochorismate mutase, (EC 5.4.4.2), (ii) an isochorismate pyruvate lyase enzyme (EC 4.2.99.21), and (iii) an exogenous feedback-insensitive DAHP synthase. In particular embodiments the microorganism comprises an exogenous PchA enzyme, an exogenous PchB enzyme, and an exogenous feedback-insensitive DAHP synthase. In one embodiment, the microorganism comprising an exogenous feedback-insensitive DAHP synthase demonstrates greater production of salicylic acid compared to a microorganism without a feedback-insensitive DAHP synthase.

Similarly, the microorganism of the invention may comprise a nucleic acid encoding both an exogenous chorismate pyruvate lyase and feedback-insensitive DAHP synthase.

In another embodiment, the microorganism of the invention does not comprise a feedback-insensitive DAHP synthase and instead merely comprises an endogenous DAHP synthase. Where production or natural concentration of aromatic amino acids is expected to be low enough so as to not induce feedback inhibition, it is not necessary to introduce a feedback-insensitive DAHP synthase.

The microorganism of the invention may produce chorismate-derived products at any concentration or in any amount. In one embodiment, the microorganism of the invention produces chorismate-derived products at a concentration of at least about 5 mg/L, 10 mg/L, 15 mg/L, 20 mg/L, 30 mg/L, 50 mg/L, 75 mg/L, 100 mg/L, 200 mg/L, 500 mg/L, 750 mg/L, 1 g/L, 1.5 g/L or 2 g/L. In one embodiment, the microorganism of the invention produces at least one chorismate-derived product at a concentration of at least 10 mg/L, 50 gm/L, 100 mg/L, 500 mg/L, 800 mg/L, or 1 g/L Furthermore, the microorganism of the invention may be engineered to produce products at a certain selectivity or at a minimum selectivity. In one embodiment, a target chorismate-derived product accounts for at least about 5%, 10%, 15%, 20%, 30%, 50%, or 75% of all fermentation products produced by the microorganism of the invention. In one embodiment, the target chorismate-derived product accounts for at least 10% of all fermentation products produced by the microorganism of the invention, such that the microorganism of the invention has a selectivity for the target chorismate-derived product of at least 10%. In another embodiment, the target chorismate-derived product accounts for at least 30% of all fermentation products produced by the microorganism of the invention, such that the microorganism of the invention has a selectivity for the target chorismate-derived product of at least 30%.

The invention further provides a method of producing a fermentation product, specifically a chorismate-derived product, comprising fermenting the microorganism of the invention in the presence of a gaseous substrate.

The invention also provides chorismate-derived products produced by fermenting a microorganism of the invention in the presence of a gaseous substrate.

Definitions and Background

The term "genetic modification" or "genetic engineering" broadly refers to manipulation of the genome or nucleic acids of a microorganism. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms. As used herein, the term "recombinant" may also be used to describe a microorganism that comprises a mutated nucleic acid or protein, including a mutated form of an endogenous nucleic acid or protein.

"Endogenous" refers to a nucleic acid or protein that is present or expressed in the wild-type or parental microorganism from which the microorganism of the invention is derived. For example, an endogenous gene is a gene that is natively present in the wild-type or parental microorganism from which the microorganism of the invention is derived. In one embodiment, the expression of an endogenous gene may be controlled by an exogenous regulatory element, such as an exogenous promoter.

"Exogenous" refers to a nucleic acid or protein that is not present in the wild-type or parental microorganism from which the microorganism of the invention is derived. In one embodiment, an exogenous gene or enzyme may be derived from a heterologous (i.e., different) strain or species and introduced to or expressed in the microorganism of the invention. In another embodiment, an exogenous gene or enzyme may be artificially or recombinantly created and introduced to or expressed in the microorganism of the invention. Exogenous nucleic acids may be adapted to integrate into the genome of the microorganism of the invention or to remain in an extra-chromosomal state in the microorganism of the invention, for example, in a plasmid.

"Enzyme activity" refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction.

"Mutated" refers to a nucleic acid or protein that has been modified in the microorganism of the invention compared to the wild-type or parental microorganism from which the microorganism of the invention is derived. In one embodiment, the mutation may be a deletion, insertion, or substitution in a gene encoding an enzyme. In another embodiment, the mutation may be a deletion, insertion, or substitution of one or more amino acids in an enzyme.

In particular, a "disruptive mutation" is a mutation that reduces or eliminates (i.e., "disrupts") the expression or activity of a gene or enzyme. The disruptive mutation may partially inactivate, fully inactivate, or delete the gene or enzyme. The disruptive mutation may be a knockout (KO) mutation. The disruptive mutation may be any mutation that reduces, prevents, or blocks the biosynthesis of a product produced by an enzyme. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The disruptive mutation may be introduced using any method known in the art.

"Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes of the invention are codon optimized for expression in *Clostridium*, particularly *Clostridium autoethanogenum*, *Clostridium ljungdahlii*, or *Clostridium ragsdalei*. In a further preferred embodiment, the genes of the invention are codon optimized for expression in *Clostridium autoethanogenum* LZ1561, which is deposited under DSMZ accession number DSM23693.

"Overexpressed" refers to an increase in expression of a nucleic acid or protein in the microorganism of the invention compared to the wild-type or parental microorganism from which the microorganism of the invention is derived. Overexpression may be achieved by any means known in the art, including modifying gene copy number, gene transcription rate, gene translation rate, or enzyme degradation rate.

The term "variants" includes nucleic acids and proteins whose sequence varies from the sequence of a reference nucleic acid and protein, such as a sequence of a reference nucleic acid and protein disclosed in the prior art or exemplified herein. The invention may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum, Clostridium beijerinckii,* or *Clostridium ljungdahlii,* the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

Nucleic acids may be delivered to a microorganism of the invention using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the invention using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate:ferredoxin oxidoreductase promoter, an Rnf complex operon promoter, an ATP synthase operon promoter, or a phosphotransacetylase/acetate kinase operon promoter.

A "microorganism" is a microscopic organism, especially a bacterium, archea, virus, or fungus. The microorganism of the invention is typically a bacterium. As used herein, recitation of "microorganism" should be taken to encompass "bacterium."

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. In one embodiment, the parental microorganism is *Clostridium autoethanogenum, Clostridium ljungdahlii,* or *Clostridium ragsdalei.* In a preferred embodiment, the parental microorganism is *Clostridium autoethanogenum* LZ1561, which is deposited under DSMZ accession DSM23693.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *Clostridium autoethanogenum, Clostridium ljungdahlii,* or *Clostridium ragsdalei.* In a preferred embodiment, the microorganism of the invention is derived from *Clostridium autoethanogenum* LZ1561, which is deposited under DSMZ accession DSM23693.

The microorganism of the invention may be further classified based on functional characteristics. For example, the microorganism of the invention may be or may be derived from a C1-fixing microorganism, an anaerobe, an acetogen, an ethanologen, a carboxydotroph, and/or a methanogen. Table 1 provides a representative list of microorganisms and identifies their functional characteristics.

TABLE 1

|  | C1-fixing | Anaerobe | Acetogen | Ethanologen | Autotroph | Carboxydotroph | Methanotroph |
| --- | --- | --- | --- | --- | --- | --- | --- |
| *Acetobacterium woodii* | + | + | + | +/− [1] | − | − | − |
| *Alkalibaculum bacchii* | + | + | + | + | + | + | − |
| *Blautia producta* | + | + | + | − | + | + | − |

TABLE 1-continued

| | C1-fixing | Anaerobe | Acetogen | Ethanologen | Autotroph | Carboxydotroph | Methanotroph |
|---|---|---|---|---|---|---|---|
| *Butyribacterium methylotrophicum* | + | + | + | + | + | + | − |
| *Clostridium aceticum* | + | + | + | − | + | + | − |
| *Clostridium autoethanogenum* | + | + | + | + | + | + | − |
| *Clostridium carboxidivorans* | + | + | + | + | + | + | − |
| *Clostridium coskatii* | + | + | + | + | + | + | − |
| *Clostridium drakei* | + | + | + | − | + | + | − |
| *Clostridium formicoaceticum* | + | + | + | − | + | + | − |
| *Clostridium ljungdahlii* | + | + | + | + | + | + | − |
| *Clostridium magnum* | + | + | + | − | + | +/−[2] | − |
| *Clostridium ragsdalei* | + | + | + | + | + | + | − |
| *Clostridium scatologenes* | + | + | + | − | + | + | − |
| *Eubacterium limosum* | + | + | + | − | + | + | − |
| *Moorella thermoautotrophica* | + | + | + | + | + | + | − |
| *Moorella thermoacetica* (formerly *Clostridium thermoaceticum*) | + | + | + | −[3] | + | + | − |
| *Oxobacter pfennigii* | + | + | + | − | + | + | − |
| *Sporomusa ovata* | + | + | + | − | + | +/−[4] | − |
| *Sporomusa silvacetica* | + | + | + | − | + | +/−[5] | − |
| *Sporomusa sphaeroides* | + | + | + | − | + | +/−[6] | − |
| *Thermoanaerobacter kivui* | + | + | + | − | + | − | − |

[1] *Acetobacterium woodi* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1.

An "anaerobe" is a microorganism that does not require oxygen for growth. An anaerobe may react negatively or even die if oxygen is present. Typically, the microorganism of the invention is an anaerobe. In a preferred embodiment, the microorganism of the invention is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). Acetogens use the acetyl-CoA pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3rd edition, p. 354, New York, N.Y., 2006). All naturally occurring acetogens are C1-fixing, anaerobic, autotrophic, and non-methanotrophic. Typically, the microorganism of the invention is an acetogen. In a preferred embodiment, the microorganism of the invention is derived from an acetogen identified in Table 1.

An "ethanologen" is a microorganism that produces or is capable of producing ethanol. Typically, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon. Typically, the microorganism of the invention is a carboxydotroph. In a preferred embodiment, the microorganism of the invention is derived from a carboxydotroph identified in Table 1.

A "methanotroph" is a microorganism capable of utilizing methane as a sole source of carbon and energy. In certain embodiments, the microorganism of the invention is derived from a methanotroph.

More broadly, the microorganism of the invention may be derived from any genus or species identified in Table 1. In a preferred embodiment, the microorganism of the invention is a *Clostridium* bacterium.

In a preferred embodiment, the microorganism of the invention is derived from the cluster of Clostridia comprising the species *Clostridium autoethanogenum*, *Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 µm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Kopke, *Curr Opin Biotechnol*, 22: 320-325, 2011).

Thus, in summary, many of the characteristics of *Clostridium autoethanogenum, Clostridium ljungdahlii*, or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum, Clostridium ljungdahlii*, or *Clostridium ragsdalei*. Isolates and mutants of *Clostridium autoethanogenum* include JA1-1 (DSM10061) (Abrini, *Arch Microbiol*, 161: 345-351, 1994), LBS1560 (DSM19630) (WO 2009/064200), and LZ1561 (DSM23693). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

"Substrate" refers to a carbon and/or energy source for the microorganism of the invention. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product.

The substrate may comprise some amount of $H_2$. For example, the substrate may comprise about 1, 2, 5, 10, 15, 20, or 30 mol % $H_2$. In some embodiments, the substrate may comprise a relatively high amount of H2, such as about 60, 70, 80, or 90 mol % $H_2$. In further embodiments, the substrate comprises substantially no $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises substantially no $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass, or reforming of natural gas. The composition of the substrate may have a significant impact on the efficiency and/or cost of the reaction. For example, the presence of oxygen (02) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The microorganism of the invention may be cultured to produce one or more products. For instance, *Clostridium autoethanogenum* produces or can be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152). In addition to one or more target products, the microorganism of the invention may also produce ethanol, acetate, and/or 2,3-butanediol.

"Selectivity" refers to the ratio of the production of a target product to the production of all fermentation products produced by a microorganism. The microorganism of the invention may be engineered to produce products at a certain selectivity or at a minimum selectivity. In one embodiment, a target product account for at least about 5%, 10%, 15%, 20%, 30%, 50%, or 75% of all fermentation products produced by the microorganism of the invention. In one embodiment, the target product accounts for at least 10% of all fermentation products produced by the microorganism of the invention, such that the microorganism of the invention has a selectivity for the target product of at least 10%. In another embodiment, the target product accounts for at least 30% of all fermentation products produced by the microorganism of the invention, such that the microorganism of the invention has a selectivity for the target product of at least 30%.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

EXAMPLES

The following examples further illustrate the invention but, of course, should not be construed to limit its scope in any way.

Example 1

This example describes general methods for culturing *C. autoethanogenum* and *C. ljungdahlii*.

*C. autoethanogenum* DSM10061 and DSM23693 (a derivate of DSM10061) and *C. ljungdahlii* DSM13528 were sourced from DSMZ (The German Collection of Microorganisms and Cell Cultures, Inhoffenstraße 7 B, 38124 Braunschweig, Germany).

Strains were grown at 37° C. in PETC medium at pH 5.6 using standard anaerobic techniques (Hungate, *Methods Microbiol*, 3B: 117-132, 1969; Wolfe, *Adv Microbiol Physiol*, 6: 107-146, 1971). Fructose (heterotrophic growth) or 30 psi CO-containing steel mill gas (collected from New Zealand Steel site in Glenbrook, NZ; composition: 44% CO, 32% $N_2$, 22% $CO_2$, 2% $H_2$) in the headspace (autotrophic growth) was used as substrate. For solid media, 1.2% bacto agar (BD, Franklin Lakes, N.J. 07417, USA) was added.

| PETC medium component | Amount per 1.0 L of PETC medium |
|---|---|
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution (see below) | 10 ml |
| Wolfe's vitamin solution (see below) | 10 ml |
| Yeast extract (optional) | 1 g |
| Resazurin (2 g/L stock) | 0.5 ml |

-continued

| | |
|---|---|
| NaHCO₃ | 2 g |
| Reducing agent solution (see below) | 0.006-0.008% (v/v) |
| Fructose (for heterotrophic growth) | 5 g |

| Trace metal solution component | Amount per 1.0 L of trace metal solution |
|---|---|
| Nitrilotriacetic acid | 2 g |
| MnSO$_4$•H$_2$O | 1 g |
| Fe(SO$_4$)$_2$(NH$_4$)$_2$•6H$_2$O | 0.8 g |
| CoCl$_2$•6H$_2$O | 0.2 g |
| ZnSO$_4$•7H$_2$O | 0.2 mg |
| CuCl$_2$•2H$_2$O | 0.02 g |
| NaMoO$_4$•2H$_2$O | 0.02 g |
| Na$_2$SeO$_3$ | 0.02 g |
| NiCl$_2$•6H$_2$O | 0.02 g |
| Na$_2$WO$_4$•2H$_2$O | 0.02 g |

| Wolfe's vitamin solution component | Amount per 1.0 L of Wolfe's vitamin solution |
|---|---|
| Biotin | 2 mg |
| Folic acid | 2 mg |
| Pyridoxine hydrochloride | 10 mg |
| Thiamine HCl | 5 mg |
| Riboflavin | 5 mg |
| Nicotinic acid | 5 mg |
| Calcium D-(+)-pantothenate | 5 mg |
| Vitamin B12 | 0.1 mg |
| P-aminobenzoic acid | 5 mg |
| Thioctic acid | 5 mg |

| Reducing agent solution component | Amount per 100 mL of reducing agent solution |
|---|---|
| NaOH | 0.9 g |
| Cysteine-HCl | 4 g |
| Na$_2$S | 4 g |

Example 2

This example demonstrates the construction of a strain comprising a p-hydroxybenzoate expression plasmid.

Figure 7:
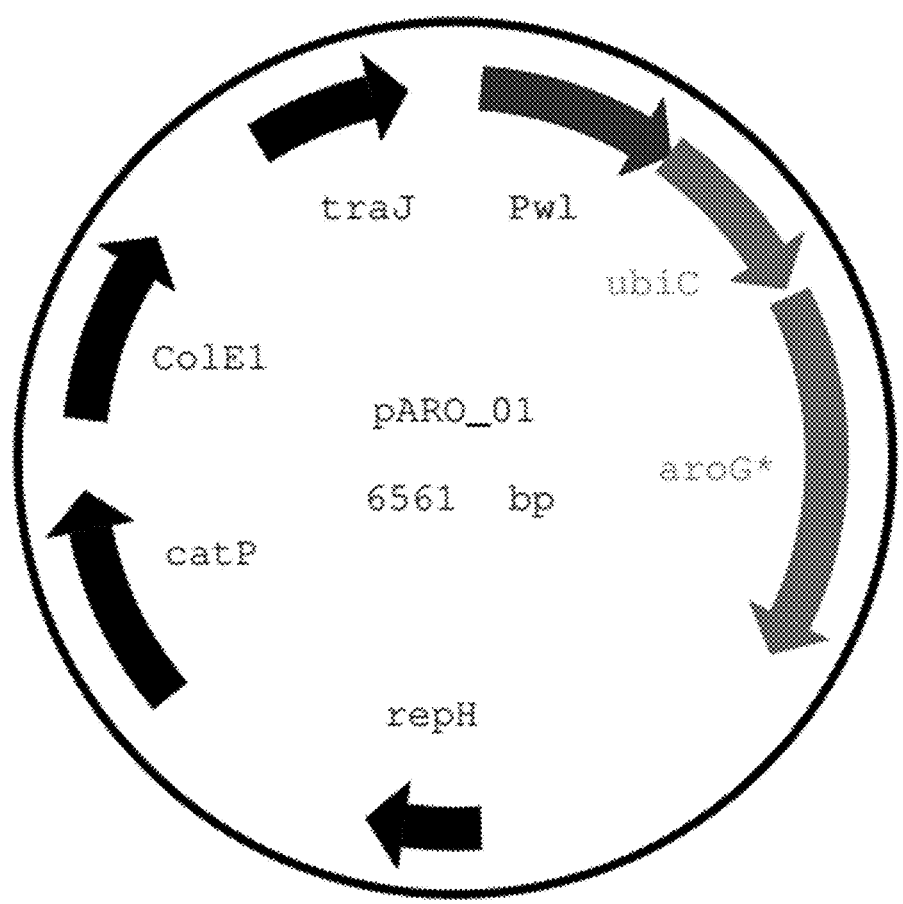
FIG. 7 is a diagram of a pARO_01 plasmid. The chorismate pyruvate lyase (ubiC) and feedback-insensitive DAHP synthase (aroG*) are under control of the Wood-Ljungdahl promoter (Pwl). Other shuttle vector features are also shown.

The nucleotide sequence for chorismate pyruvate lyase (ubiC) (SEQ ID NO: 1) was optimized (SEQ ID NO: 2) according to the *C. autoethanogenum* codon-usage table by GeneArt and cloned into the pMTL8315 expression vector (FIG. 7) under control of the Wood-Ljungdahl pathway promoter (US 20110256600). The coding sequence for a feedback-insensitive mutant 3-deoxy-D-arabino-heptulosonate-7-phosphate (DAHP) synthase (aroG*) (SEQ ID NO: 8) was also included, following ubiC in a bicistronic format (FIG. 7). The plasmid pARO_01 (SEQ ID NO: 9) was transformed into *C. autoethanogenum* LZ1561 (DSM23693) via conjugation with *E. coli* strain CA434 as donor. Donor strains were grown overnight in LB media supplemented with 25 µg/mL chloramphenicol and 100 µg/mL spectinomycin. Cells from 1.5 mL of culture were harvested by centrifugation and washed in phosphate buffered saline (PBS). Inside an anaerobic workstation, the donor cell pellet was resuspended in 200 µL of exponentially growing recipient LZ1561. The conjugation mixture was spotted on PETC-MES agar medium and incubated at 37° C. After 24 hours the cells were scraped from the conjugation plate and spread on PETC-MES agar medium supplemented with 7.5 µg thiamphenicol/mL (Sigma) and 10 µg trimethoprim/mL (Sigma). Three plasmid-bearing colonies (i.e. biological triplicates) isolates were grown in PETC-MES liquid medium containing 7.5 µg thiamphenicol/mL and with a gas blend that simulates steel mill off gas as the carbon source (50% CO, 10% H$_2$, 30% CO$_2$, 10% N$_2$, subsequently referred to as "mill gas" in this application).

Figure 8:
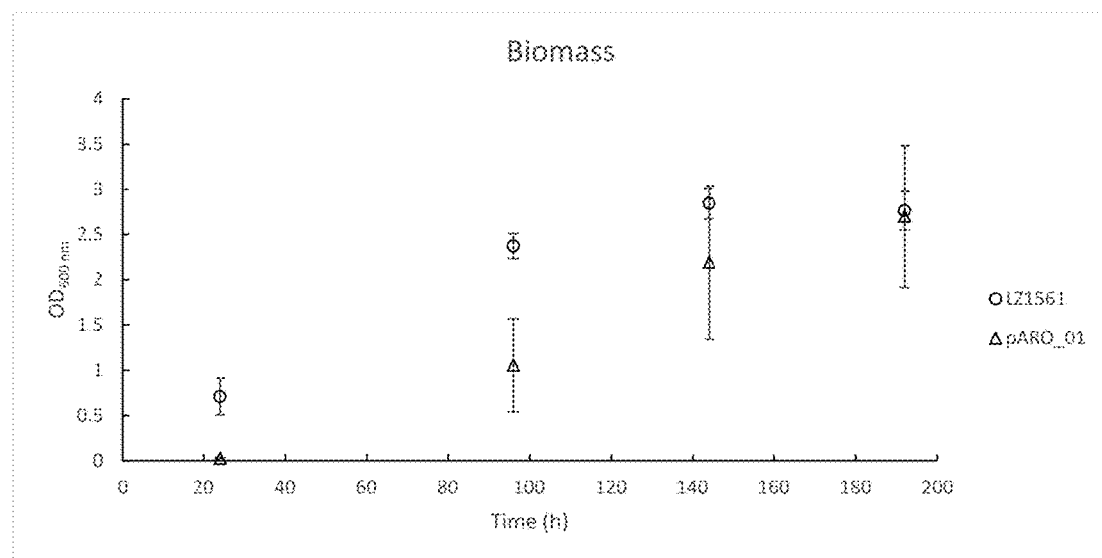
FIG. 8 is a graph showing biomass accumulation in test strains. Biomass was estimated by measuring the absorbance of culture samples at 600 nm at different time points. Data points represent the mean of n=3 replicate cultures ±1 standard deviation. LZ1561 refers to untransformed *C. autoethanogenum* LZ1561. pARO_01(1) and pARO_01(2) are biological replicates of *C. autoethanogenum* LZ1561 transformed with the pARO_01 plasmid.
Figure 9A:
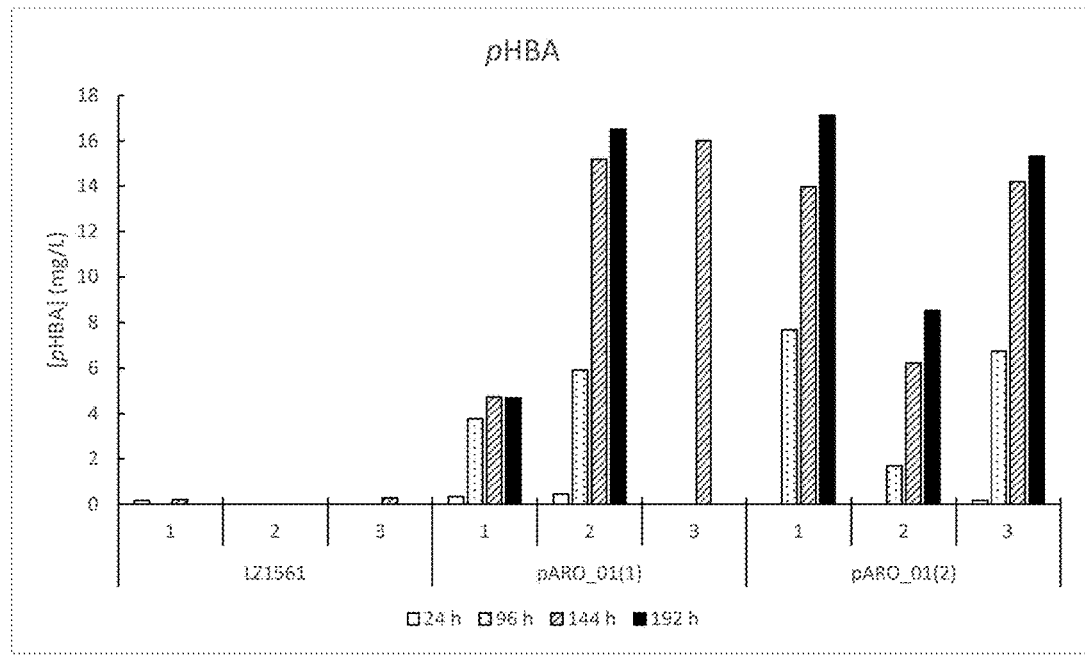
FIGS. 9a and 9b are graphs showing p-hydroxybenzoate accumulation in test strains.
Figure 9B:
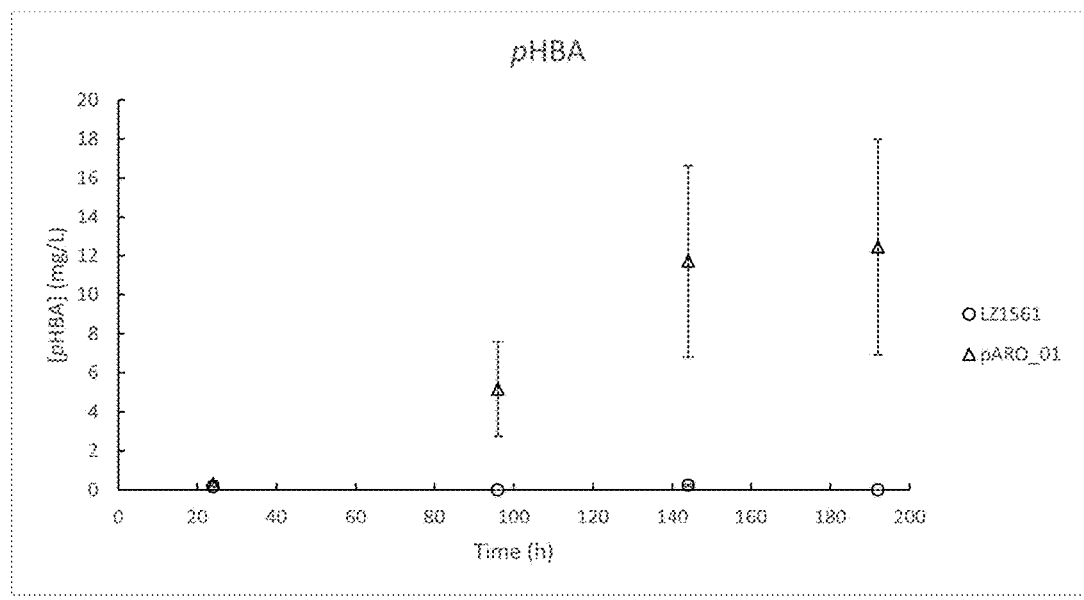

Liquid cultures were grown in 10 mL PETC-MES medium in serum bottles containing thiamphenicol and mill gas at 22 psi. Samples were taken daily to measure biomass (FIG. 8) and pHBA (FIG. 9a and FIG. 9b).

To measure pHBA, samples (100 µL) were spiked with 10 µL 0.1N NaOH, frozen, and then freeze dried. The samples were then derivatised with 100 µL BSTFA+TCMS (99:1) and pyridine 100 µL. The samples were then incubated at 60° C. for 30 min to form trimethyl silyl derivatives of the carboxylic acid functional group. Details of GC-MS method are: Inj. Vol. 1 uL; Inj. T 250° C.; split ratio 10:1. Initial T 50° C. (hold 5 min); final T 220° C. (20° C./min); const. flow 1 mL/min (He carrier gas); column Zebron ZB-5MS 30 m×0.25 mm×0.25 µm. Varian Ion Trap 4000 operated in full scan mode 40-400 m/z. Tune PFTBA In FIG. 9a, LZ1561 (the control strain) has three technical replicates (i.e., grown and sampled three times). Two biological replicates of LZ1561 with pARO_01, were also prepared, each with three technical replicates. "Technical replicate" refers to growing and sampling each strain in separate experiments, while "biological replicate" refers to reproducing the strain from scratch. In this way, the biological replicates account for background biological variation in the microorganism, while technical replicates account for variation due to technical aspects including culture, sampling, and analysis methods. FIG. 9a shows that pHBA was produced repeatedly in separate instances. FIG. 8 and FIG. 9b give an overall representation of growth and pHBA productivity.

Example 3

This example demonstrates the production of p-hydroxybenzoate via gas fermentation.

Figure 5:
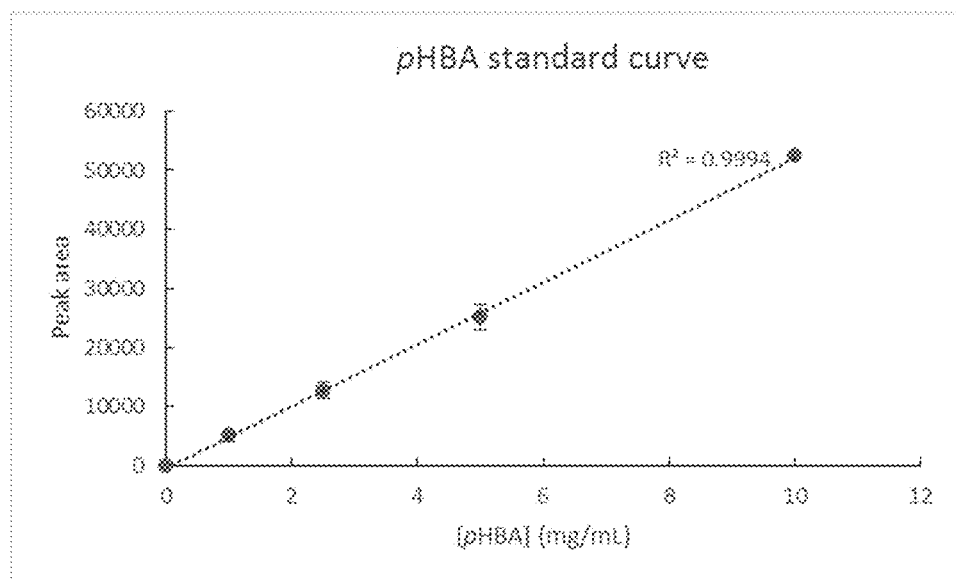
FIG. 5 is a graph of a standard curve showing quantitation of authentic pHBA standards.
Figure 6A:
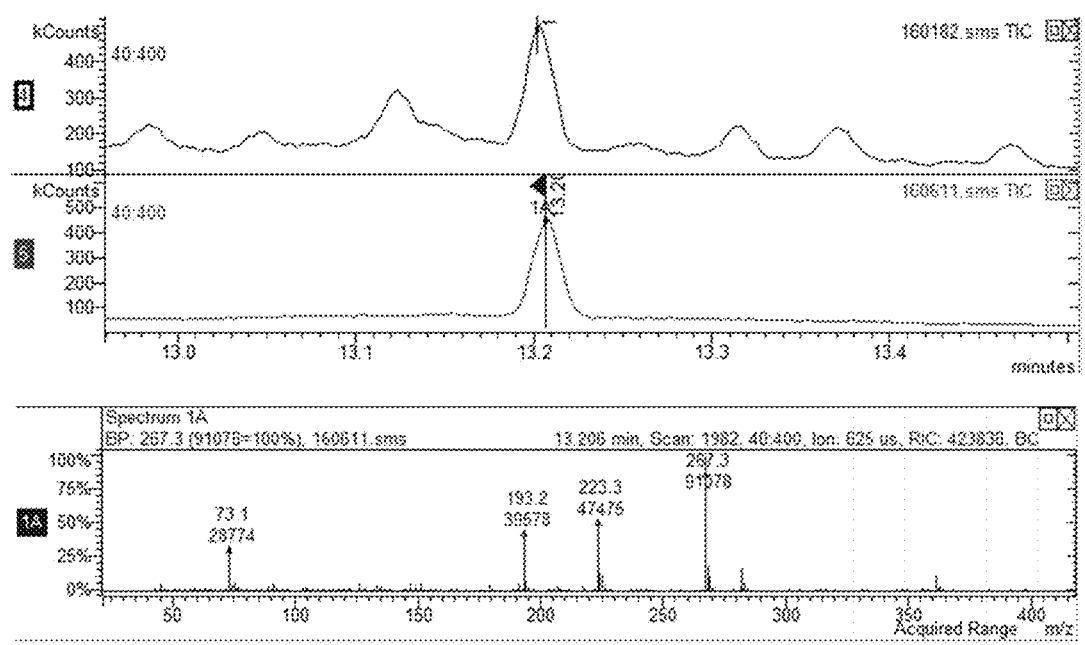
FIG. 6a is a graph showing the total ion count of authentic standards (i) authentic standard of pHBA (trimethylsilyated) prepared in supernatant from *C. autoethanogenum* LZ1561 culture medium, (ii) authentic standard of pHBA (trimethylsilyated) prepared in water, and (iii) mass spectrum of trimethylsilyated pHBA.
Figure 6B:
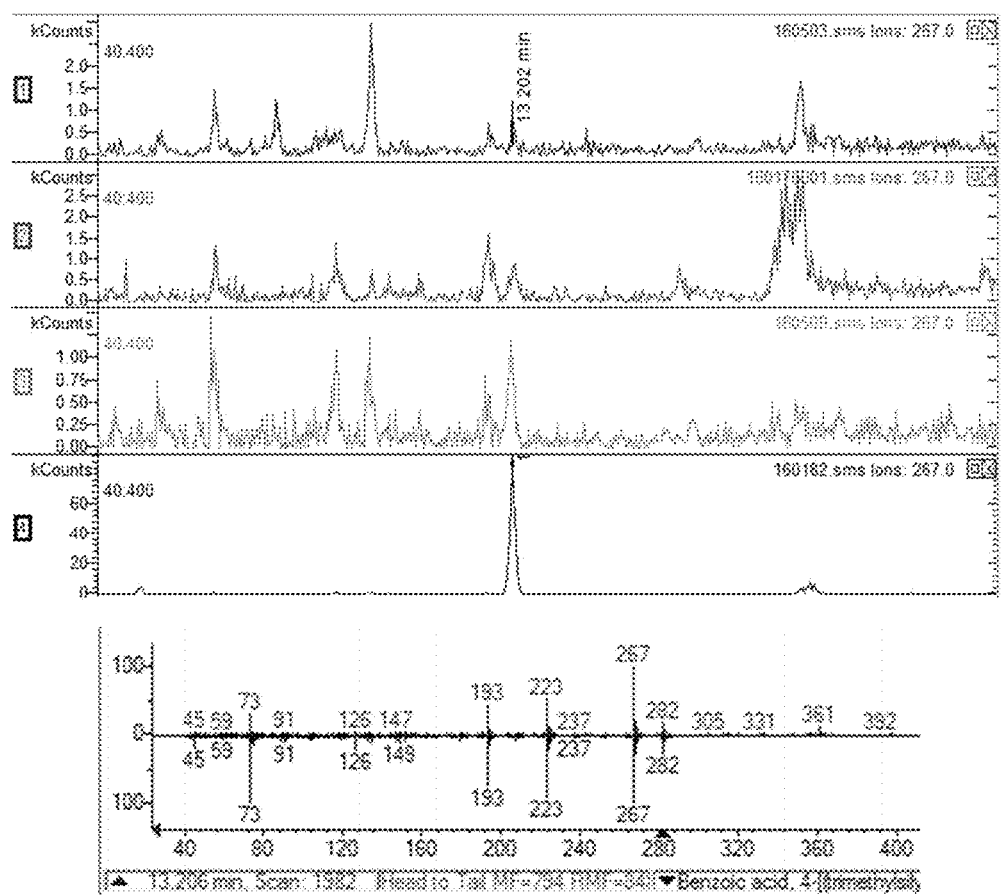
FIG. 6b is a graph showing selected ion monitoring of fermentation samples and standards: (i) *C. autoethanogenum* LZ1561 without pARO_01 plasmid, (ii) and (iii) samples from *C. autoethanogenum* LZ1561 bearing pARO_01 plasmid, (iv) authentic standard of pHBA, and (v) total ion count comparison between NIST database entry for pHBA and pHBA peak from LZ1561/pARO_01.

*C. autoethanogenum* harbouring plasmid pARO_01 (SEQ ID NO: 9) were grown on mill gas as described in Example 1. GC-MS analysis, performed as in Example 1, of the culture determined that pHBA was produced by the bacterium expressing chorismate pyruvate lyase. The linear range for analysis of pHBA using this method spanned 0-12.5 mg/mL (FIG. 5).

pHBA was validated by comparison to retention time and characteristic fragment ions of an authentic pHBA standard and predicted characteristic ions from the NIST mass spectrometry database (FIG. 6).

pHBA production was observed in all cultures expressing the chorismate-pyruvate lyase encoded on the pMTL8315 expression vector. The peak titre of pHBA observed in any one culture was 17 mg pHBA/L after eight days (FIG. 9b). No pHBA was observed in the control sample without the expression vector.

Detectable levels of pHBA were produced by the genetically engineered bacterium and present in the culture.

Example 4

This example demonstrates an experimental protocol for increasing the production of pHBA through enzyme engineering.

UbiC is subject to product inhibition through retention of pHBA. The nucleic acid sequence encoding ubiC may be modified such that amino acids involved in product retention by the enzyme are mutated and release of product is enhanced. To do this, the amino acids involved in pHBA binding are identified by analysis of existing structures with bound product. Product inhibition is then minimised by mutating the amino acids involved in pHBA binding and retention. To identify enzymes with the greatest catalytic efficiency for pHBA yield, a targeted library of ubiC mutants can be produced where different combinations of pHBA-binding amino acids are altered, and these mutant enzymes can be analysed with an enzyme assay. Improved mutants are then expressed in C. autoethanogenum LZ1561 to validate the strains with most improved pHBA productivity.

Example 5

This example demonstrates the construction of a strain comprising a salicylate expression plasmid.

The nucleotide sequences for pchA (SEQ ID NO: 4) and pchB (SEQ ID NO: 6) were codon optimized and cloned into the expression vector under control of a tetracycline-inducible promoter. The plasmid is transformed into C. autoethanogenum LZ1561 (DSM23693) via conjugation with E. coli strain CA434 as donor. Donor strains were grown overnight in LB media supplemented with 25 μg/mL chloramphenicol and 100 μg/mL spectinomycin. Cells from 1.5 mL culture were harvested by centrifugation and washed in phosphate buffered saline (PBS). Inside an anaerobic workstation, the donor cell pellet was resuspended in 200 μL of exponentially growing recipient C. autoethanogenum. The conjugation mixture was spotted on PETC-MES agar medium and incubated at 37° C. After 24 hours the cells were scraped from the conjugation plate and spread on PETC-MES agar medium supplemented with 7.5 μg thiamphenicol/mL (Sigma) and 10 μg trimethoprim/mL (Sigma). Three plasmid-bearing colonies (i.e. biological triplicates) isolates were grown in PETC-MES liquid medium containing 7.5 μg thiamphenicol/mL and with mill gas as the carbon source.

Liquid cultures were grown in 10 mL PETC-MES medium in serum bottles containing thiamphenicol and mill gas at 22 psi.

Biomass was monitored spectrophotometrically. At OD600 nm=0.3 expression of the salicylate biosynthetic pathway was induced by addition of 40 ng anhydrotetracycline/mL. Duplicate cultures (technical replicates of the three biological triplicates) were grown without the addition of anhydrotetracylcine such that the salicylate biosynthetic pathway remained uninduced. Samples were taken daily Salicylate concentrations were measured using gas chromatography mass spectrometry analysis (GCMS), employing a Thermo Scientific ISQ LT GCMS equipped an Agilent CP-SIL 5CB-MS (50 m×0.25 μm×0.25 μm) column and autosampler. Samples were prepared by diluting 300 μL of sample with 600 μL of acetonitrile and 50 μL 0.1N NaOH. The samples were vortexed then centrifuged for 3 minutes at 14,000 rpm; 800 μL of the supernatant was transferred to a glass vial and the sample was dried in a Thermo SpeedVac®. Once dry, the samples were then suspended in a solution of 100 μl of pyridine containing 22 mg/ml methoxyamine HCl then heated in a sealed glass vial for 60 minutes at 60° C. After which, 300 μL N,O-Bistrifluoroacetamide (BSTFA) was added then heated in a sealed glass vial for 60 minutes at 60° C. Samples were transferred to an autosampler for analysis using a 1.5 μL injection, a split ration of 20 to 1, and an inlet temperature of 250° C. Chromatography was performed with an oven program of 80° C. (no hold) to a ramp of 3° C./min to 140° C. to a ramp of 20° C./min to 230° C. with a 4-min final hold. The column flow rate was 38 cm²/min, with helium as the carrier gas. The MS ion source was kept at 280° C. Quantitation, was performed using 267 m/z for a quantification ion with 135 and 45 m/z used as qualifier ions.

Figure 11A:
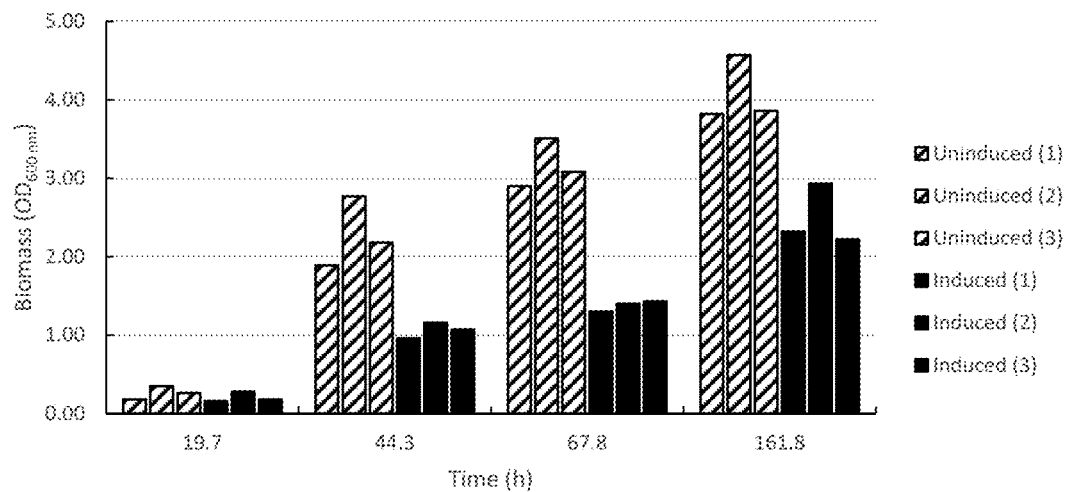
FIG. 11a is a graph showing biomass growth of the salicylate production strain with and without induction of the salicylate biosynthetic pathway.
Figure 11B:
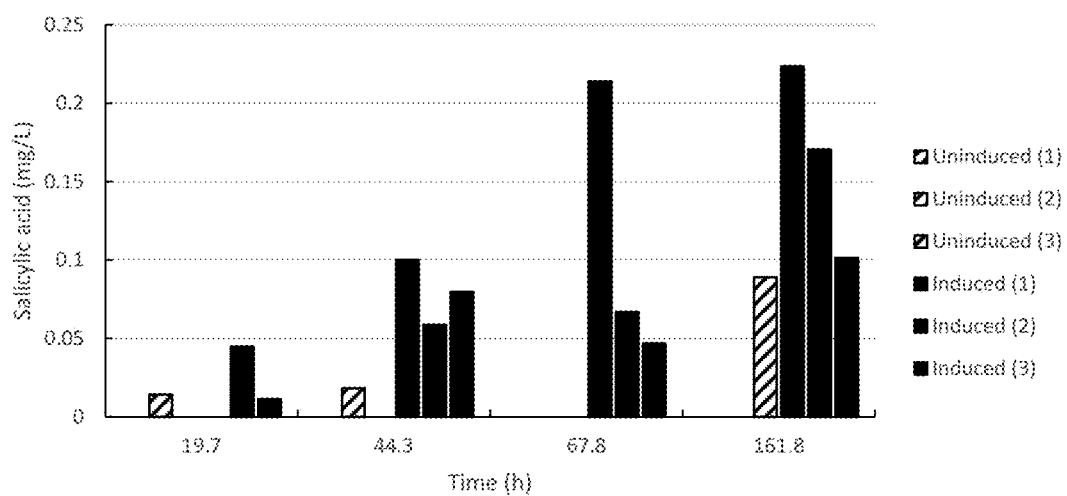
FIG. 11b is a graph showing the difference in accumulation of salicylate in liquid cultures of the test strain with and without induction of the salicylate biosynthetic pathway.

FIG. 11a shows a comparison of biomass growth in the induced and un-induced samples. FIG. 11b shows that salicylate was produced repeatedly.

Example 6

This example demonstrates knockout of pheA for enhanced production of chorismate-derived products.

pheA (e.g. from C. autoethanogenum, CAETHG_0905 (CP006763.1:973789 ... 974925)) is a gene that encodes the enzyme prephenate synthase. Prephenate synthase catalyses the conversion of chorismate to prephenate, which is a precursor to the aromatic amino acids phenylalanine and tyrosine. pheA function was knocked out by disrupting the gene using the ClosTron method (Heap et al., J Microbiol Methods. 2010, 80(1):49-55). The ClosTron plasmid pMTL007C-E2 was generated by DNA2.0 and transformed into C. autoethanogenum LZ1561 (DSM23693) via conjugation with E. coli strain CA434 as donor. Donor strains were grown overnight in LB media supplemented with 25 μg/mL chloramphenicol. Cells from 1.5 mL culture were harvested by centrifugation and washed in phosphate buffered saline (PBS). Inside an anaerobic workstation, the donor cell pellet was resuspended in 200 μL of exponentially growing recipient C. autoethanogenum LZ1561. The conjugation mixture was spotted on PETC agar media and incubated at 37° C. After 24 hours the cells were scraped and resuspended in 500 μL PBS and spread on PETC agar media supplemented with 7.5 μg/mL thiamphenicol (Sigma) and 10 μg/mL trimethoprim (Sigma). Plasmid-bearing isolates were grown in PETC-MES liquid medium containing 7.5 μg thiamphenicol/mL and with mill gas as the carbon source.

Colonies were streaked on PETC solid media containing the antibiotic clarithromycin (5 μg/mL). This step selected for integration of the intron retargeting sequence into the genome. Integration of the intron sequence into the target site results in an 1800 base pair insertion in the genome, which was screened for with colony PCR The PCR product of the positive ClosTron mutants were purified and sequenced to confirm the insertion site.

Liquid cultures were grown in 10 mL PETC-MES medium in serum bottles containing clarithromycin and mill gas at 22 psi. Glycerol stock was prepared from this serum bottle Bioreactor experiments were carried out in a 2 L BioFlo 115 water jacket system (New Brunswick Scientific Corp., Edison, N.J.) with a working volume of 1.5 L. The CSTR system was equipped with two six-bladed Rushton impellers and baffles enhance the mixing of fermentation broth and the gas to liquid mass transfer. A pH and an oxidation-reduction potential (ORP) electrode (Broadley-James Corporation) were inserted through the headplate and their readings were recorded at 5 min intervals. pH was maintained at 5.0 by automated addition of a 5 M solution of ammonium hydroxide.

The inoculum was prepared from a glycerol stock. One mL of glycerol stock was transferred into 50 mL of PETC media with 22 psi mill gas as carbon source. The culture was incubated at 37° C. for on a shaker two to three days until a visible growth was observed. The culture was then used to inoculate 200 mL of fresh media in 1 L-Schott bottle and mill gas was added to a pressure of 22 psi. The Schott bottle was incubated for another 24 to 36 hours before being transferring to the fermenters.

The agitation was set at 200 rpm and the gas flow was set at 35 mL/min/L. After one day, the stirring rate was increased by 25 rpm at 4 hours intervals to the maximum value of 900 rpm. The gas flow was increased by 25 mL/min/L at 4 hours intervals to the maximum flow rate that the target CO uptake can be achieved. The $Na_2S$ was added over the course of the fermentation with an initial pump rate of 0.3 mL/h and later increased in 0.2 mL/h increments when the $H_2S$ concentration in the headspace dropped below 200~ppm. The CO and $H_2$ consumption and $CO_2$ production along with the $H_2S$ concentration were measured hourly using gas chromatography (GC). Liquid samples were taken from the fermenter at regular intervals over the course of the fermentation to determine cell mass and metabolite concentrations using HPLC.

After starting up in batch mode, the fermenter was turned to continuous when the OD reached a value of 2. The media and nutrient inflow rates were controlled by one or more precision peristaltic pumps (Masterflex L/S digital drive pumps) while the fermenter volume was held constant by using a level probe that triggers a pump to remove fermentation broth from the CSTR. The dilution rate was set in one step to 0.5 day$^{-1}$ and further increased to 1 day$^{-1}$ then to 1.7 day$^{-1}$ at 24 hour intervals.

An additional equipment was added to the fermentation was a hollow fibre membrane (GE Healthcare) with a pore size of 0.2 µm and a surface area of 1,200 cm$^2$. The membrane was used to increase the cell concentration in the fermentation. The fermentation broth was pumped at high speed through the membrane and returned back to the fermenter while a stream of cell-free filtrate was pumped to the filtrate tank at a slower rate than the media pump rate. This allowed the retention time of the bacteria cell in the fermenter to increase.

Figure 10:
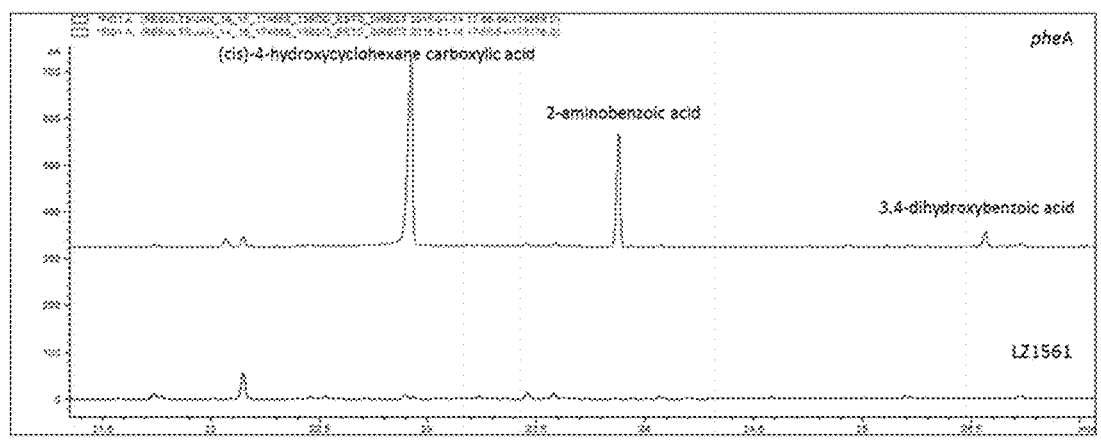
FIG. 10 is a graph showing production of new aromatic compounds in a genetically engineered *Clostridium* bacterium comprising a disruptive mutation in a nucleic acid encoding pheA. The ΔpheA strain produces 4-hydroxy cyclohexane carboxylic acid, 2-aminobenzoic acid, and 3,4-dihydroxybenzoic acid, while the control strain (LZ1561) does not.

As shown in FIG. 10, three new compounds were identified using GC-MS. These compounds were cis-4-hydroxycyclohexane carboxylic acid, 3,4-dihydroxybenzoic acid, and 2-aminobenzoic acid. These compounds were only detected in this pheA::CT culture and were not detected in the parental strain (LZ1561) culture.

3,4 dihydroxy benzoic acid, 2-aminobenzoic acid and cis-4-hydroxycyclohexanecarboxylic acid concentrations were measured using gas chromatography (GC) analysis, employing an Agilent 6890N GC equipped a Agilent CP-SIL 5CB-MS (50 m×0.25 µm×0.25 µm) column, autosampler and a flame ionization detector (FID). Samples were prepared by diluting 400 µL of sample with 400 µL of acetonitrile, followed by a 3 minute centrifugation at 14,000 rpm; the supernatant was transferred to a glass vial and the sample was dried in a Thermo SpeedVac®. Once dry, the samples were then suspended in a solution of 400 µL of N,O-Bistrifluoroacetamide (BSTFA) and pyridine (3:1 ratio) and heated in a sealed glass vial for 60 minutes at 60° C. Samples were transferred to an autosampler for analysis using a 1 µL injection, a split ration of 30 to 1, and an inlet temperature of 250° C. Chromatography was performed with an oven program of 70° C. (no hold) to a ramp of 3° C./min to 110° C. to a ramp of 15° C./min to 230° C., followed by a final ramp of 40° C./min to 310° C. with a 3-min hold. The column flow rate was 1.8 ml/min, with helium as the carrier gas. The FID was kept at 320° C., with hydrogen at 40 ml/min, air at 400 ml/min, and helium at 20 ml/min as the makeup gas.

Figure 12:
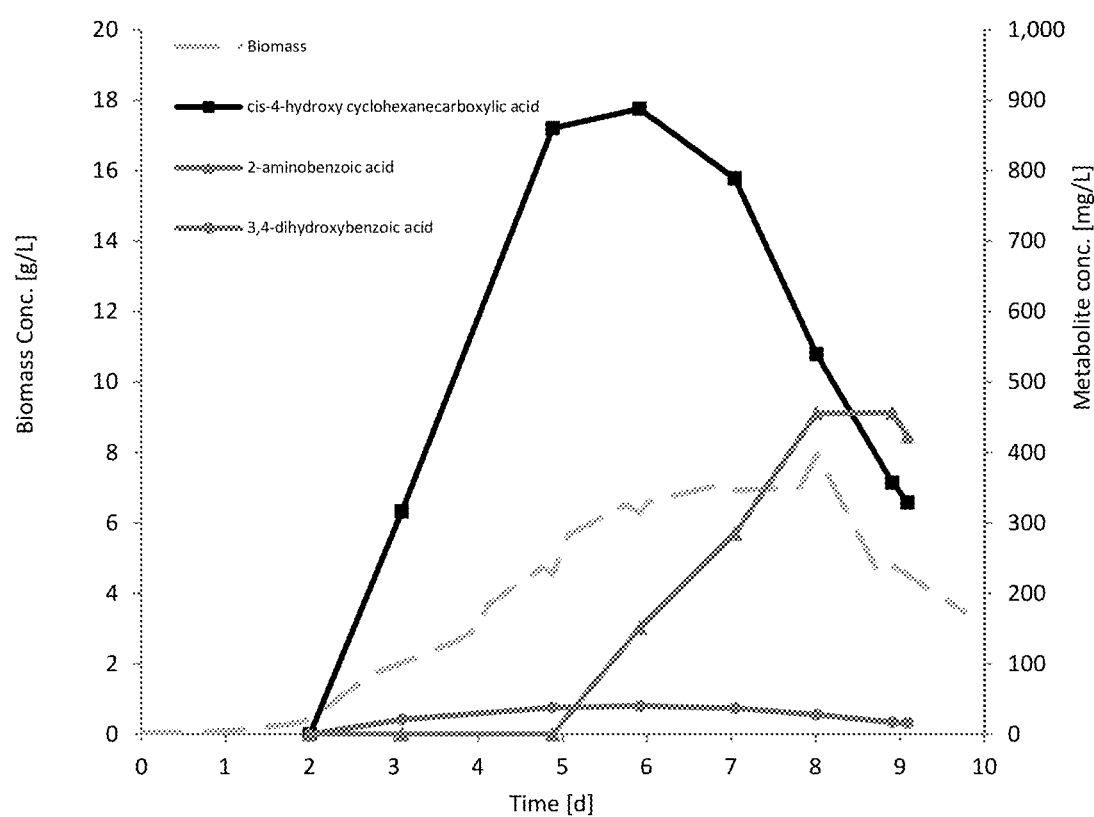
FIG. 12 is a graph showing concentration of 4-hydroxy cyclohexane carboxylic acid, 2-aminobenzoic acid, and 3,4-dihydroxybenzoic acid produced by fermentation of an engineered *Clostridium* bacterium comprising a disruptive mutation in a nucleic acid encoding pheA.

FIG. 12 shows the concentration of cis-4-hydroxycyclohexane carboxylic acid, 3,4-dihydroxybenzoic acid, and 2-aminobenzoic acid over the course of the fermentation run. As shown in FIG. 12, compound cis-4-hydroxycyclohexanecarboxylic acid increased to a concentration of about 0.9 g/L on day 6 of the fermentation. 2-aminobenzoic acid accumulated to a concentration of about 0.45 g/L on day 8-9 of the fermentation. 3,4-dihydroxybenzoic acid was produced in smaller amounts, peaking at a concentration of around 0.3 g/L between days 6-8. A total accumulation of cis-4-hydroxycyclohexanecarboxylic acid, 2-aminobenzoic acid and 3,4-dihydroxybenzoic acid of >1.3 g/L was observed on day 6.

Little is known in literature about the production of cis-4-hydroxycyclohexanecarboxylic acid. There is only one report that cis-4 hydroxycyclohexanecarboxylic acid was detected in a child's urine sample using GC-MS. It was hypothesized that the compound was a by-product of enteric bacterial metabolism (Kronick, *Clinica Chimica Acta*, 132: 205-208, 1983). It seems likely that this compound is a direct product of chorismate or prephanate as the reaction mechanism may be explained by a cleavage of the pyruvate molecule followed by a reduction requiring a further 2.5 $H_2$ molecules that may be provided through NAD(P)H.

2-Aminobenzoic acid is a known intermediate in the chorismate to tryptophan pathway. Anthranilate synthase catalyses the amination followed by the aromatization of chorismate to obtain the aromatic backbone of the tryptophan molecule. It is known that the gene expression of anthranilate synthase is highly regulated and subjected to feedback inhibition by the end product tryptophan (Dosselaere, *Crit Rev Microbiol*, 27: 75-131, 2001). 2-Aminobenzoic acid was only secreted into the fermentation broth when growth ceased indicating that it is an overflow product that was no longer reacted away when growth had stopped.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A genetically engineered C1-fixing bacterium capable of producing at least one chorismate-derived product, wherein the bacterium comprises at least one of:
   a. an exogenous chorismate pyruvate lyase,
   b. an exogenous isochorismate synthase,
   c. an exogenous isochorismate pyruvate lyase, and
   d. a prephenate synthase comprising a disruptive mutation that partially inactivates, fully inactivates, deletes, or knocks out the prephenate synthase.

2. The bacterium of claim 1, wherein the bacterium is a *Clostridium* bacterium capable of producing at least one chorismate-derived product by fermentation of a gaseous substrate.

3. The bacterium of claim 1, wherein the chorismate pyruvate lyase is ubiC.

4. The bacterium of claim 1, wherein the isochorismate synthase is pchA.

5. The bacterium of claim 1, wherein the isochorismate pyruvate lyase is pchB.

6. The bacterium of claim 1, wherein the prephenate synthase is pheA.

7. The bacterium of claim 1, wherein the disruptive mutation reduces or eliminates the expression or activity of the prephenate synthase.

8. The bacterium if claim 7, wherein the bacterium produces a reduced amount of prephenate or prephenate-derived products compared to a parental bacterium.

9. The bacterium of claim 7, wherein the bacterium produces substantially no tyrosine or phenylalanine.

10. The bacterium of claim 1, wherein the bacterium comprises at least one nucleic acid encoding at least one of:
    a. the exogenous chorismate pyruvate lyase,
    b. the exogenous isochorismate synthase,
    c. the exogenous isochorismate pyruvate lyase, and
    d. the prephenate synthase comprising a disruptive mutation.

11. The bacterium of claim 10, wherein the nucleic acid is codon optimized for expression in *Clostridium*.

12. The bacterium of claim 1, wherein the chorismate-derived product comprises a 6-membered carbon ring substituted with a carboxyl group or carboxylate anion and further substituted with one or more OH groups and/or one or more $NH_2$ groups.

13. The bacterium of claim 1, wherein the chorismate-derived product is selected from the group consisting of para-hydroxybenzoic acid, salicylate, 2-aminobenzoate, dihydroxybenzoate, 4-hydroxycyclohexane carboxylic acid, and salts and ions thereof.

14. The bacterium of claim 1, wherein the bacterium expresses a chorismate pyruvate lyase of ubiC and produces a chorismate-derived product of para-hydroxybenzoic acid.

15. The bacterium of claim 1, wherein the bacterium expresses an isochorismate synthase of pchA and an isochorismate pyruvate lyase of pchB and produces a chorismate-derived product of salicylate.

16. The bacterium of any one of claims 14 and 15, wherein the bacterium further expresses a feedback-insensitive DAHP synthase.

17. The bacterium of claim 1, wherein the bacterium comprises a prephenate synthase comprising a disruptive mutation and produces a chorismate-derived product of 2-aminobenzoate, 2,3-dihydroxybenzoate, or 4-hydroxycyclohexane carboxylic acid.

18. The bacterium of claim 1, wherein the bacterium produces at least one chorismate-derived product not produced by a parental bacterium.

19. The bacterium of claim 1, wherein the bacterium produces a greater amount of at least one chorismate-derived product than a parental bacterium.

20. The bacterium of claim 1, wherein the bacterium is derived from a parental bacterium selected from the group consisting of *Clostridium autoethanogenum, Clostridium ljungdahlii*, and *Clostridium ragsdalei*.

21. The bacterium of claim 20, wherein the *Clostridium autoethanogenum* is *Clostridium autoethanogenum* DSM23693.

22. The bacterium of claim 1, wherein the gaseous substrate comprises at least one of CO, $CO_2$, and $H_2$.

23. A method of producing a fermentation product, comprising fermenting the bacterium of claim 1 in the presence of a gaseous substrate to produce a fermentation product.

24. The method of claim 23, wherein the gaseous substrate comprises at least one of CO, $CO_2$, and $H_2$.

* * * * *

```
                            SEQUENCE LISTING

<160> NUMBER OF SEQ ID NOS: 11

<210> SEQ ID NO 1
<211> LENGTH: 165
<212> TYPE: PRT
<213> ORGANISM: Escherichia coli

<400> SEQUENCE: 1

Met Ser His Pro Ala Leu Thr Gln Leu Arg Ala Leu Arg Tyr Phe Lys
1               5                   10                  15

Glu Ile Pro Ala Leu Glu Pro Gln Leu Leu Asp Trp Leu Leu Leu Glu
            20                  25                  30

Asp Ser Met Thr Lys Arg Phe Glu Gln Gln Gly Lys Thr Val Ser Val
        35                  40                  45

Thr Met Ile Arg Glu Gly Phe Val Glu Gln Asn Glu Ile Pro Glu Glu
    50                  55                  60

Leu Pro Leu Leu Pro Lys Glu Ser Arg Tyr Trp Leu Arg Glu Ile Leu
65                  70                  75                  80

Leu Cys Ala Asp Gly Glu Pro Trp Leu Ala Gly Arg Thr Val Val Pro
                85                  90                  95

Val Ser Thr Leu Ser Gly Pro Glu Leu Ala Leu Gln Lys Leu Gly Lys
            100                 105                 110

Thr Pro Leu Gly Arg Tyr Leu Phe Thr Ser Ser Thr Leu Thr Arg Asp
        115                 120                 125

Phe Ile Glu Ile Gly Arg Asp Ala Gly Leu Trp Gly Arg Arg Ser Arg
    130                 135                 140

Leu Arg Leu Ser Gly Lys Pro Leu Leu Leu Thr Glu Leu Phe Leu Pro
145                 150                 155                 160

Ala Ser Pro Leu Tyr
                165

<210> SEQ ID NO 2
<211> LENGTH: 273
<212> TYPE: DNA
<213> ORGANISM: Escherichia coli

<400> SEQUENCE: 2
tttcccgcgc gctgggaaat cctagagatt ctttgagagc ccttggaaaa tatataggcg      60
cgttgcgcga aaattcgcgc gcttgcaaaa ggctctcgga gagattcccc ttagagagat     120
atagaggata ggggcccgga ggatatatag ggtttgggaa agagagatct gcgcgcgctg     180 agggaggag agagagatcg ctctagatcg atagcggata gacctctaga gatcccgcgc     240
gatagagaaa gggcctctcg agagatcgcg caa                                  273

<210> SEQ ID NO 3
<211> LENGTH: 476
<212> TYPE: PRT
<213> ORGANISM: Pseudomonas aeruginosa

<400> SEQUENCE: 3

Met Ser Arg Leu Ala Pro Leu Ser Gln Cys Leu His Ala Leu Arg Gly
1               5                   10                  15
```

```
Thr Phe Glu Arg Ala Ile Gly Gln Ala Gln Ala Leu Asp Arg Pro Val
             20                  25                  30
Leu Val Ala Ala Ser Phe Glu Ile Asp Pro Leu Asp Pro Leu Gln Val
         35                  40                  45
Phe Gly Ala Trp Asp Asp Arg Gln Thr Pro Cys Leu Tyr Trp Glu Gln
 50                  55                  60
Pro Glu Leu Ala Phe Phe Ala Trp Gly Cys Ala Leu Glu Leu Gln Gly
 65                  70                  75                  80
His Gly Glu Gln Arg Phe Ala Arg Ile Glu Glu Asn Trp Gln Leu Leu
                 85                  90                  95
Cys Ala Asp Ala Val Val Glu Gly Pro Leu Ala Pro Arg Leu Cys Gly
                100                 105                 110
Gly Phe Arg Phe Asp Pro Arg Gly Pro Arg Glu Glu His Trp Gln Ala
            115                 120                 125
Phe Ala Asp Ala Ser Leu Met Leu Ala Gly Ile Thr Val Leu Arg Glu
130                 135                 140
Gly Glu Arg Tyr Arg Val Leu Cys Gln His Leu Ala Lys Pro Gly Glu
145                 150                 155                 160
Asp Ala Leu Ala Leu Ala Ala Tyr His Cys Ser Ala Leu Leu Arg Leu
                165                 170                 175
Arg Gln Pro Ala Arg Arg Pro Ser Gly Pro Thr Ala Gly Ala Gln
            180                 185                 190
Gly Asp Ala Ser Ala Gln Glu Arg Gln Trp Glu Ala Lys Val Ser
            195                 200                 205
Asp Ala Val Ser Ser Val Arg Gln Gly Arg Phe Gly Lys Val Val Leu
210                 215                 220
Ala Arg Thr Gln Ala Arg Pro Leu Gly Asp Ile Glu Pro Trp Gln Val
225                 230                 235                 240
Ile Glu His Leu Arg Leu Gln His Ala Asp Ala Gln Leu Phe Ala Cys
                245                 250                 255
Arg Arg Gly Asn Ala Cys Phe Leu Gly Ala Ser Pro Glu Arg Leu Val
            260                 265                 270
Arg Ile Arg Ala Gly Glu Ala Leu Thr His Ala Leu Ala Gly Thr Ile
        275                 280                 285
Ala Arg Gly Gly Asp Ala Gln Glu Asp Ala Arg Leu Gly Gln Ala Leu
290                 295                 300
Leu Asp Ser Ala Lys Asp Arg His Glu His Gln Leu Val Val Glu Ala
305                 310                 315                 320
Ile Arg Thr Ala Leu Glu Pro Phe Ser Glu Val Leu Glu Ile Pro Asp
                325                 330                 335
Ala Pro Gly Leu Lys Arg Leu Ala Arg Val Gln His Leu Asn Thr Pro
            340                 345                 350
Ile Arg Ala Arg Leu Ala Asp Ala Gly Gly Ile Leu Arg Leu Leu Gln
        355                 360                 365
Ala Leu His Pro Thr Pro Ala Val Gly Gly Tyr Pro Arg Ser Ala Ala
370                 375                 380
Leu Asp Tyr Ile Arg Gln His Glu Gly Met Asp Arg Gly Trp Tyr Ala
385                 390                 395                 400
Ala Pro Leu Gly Trp Leu Asp Gly Glu Gly Asn Gly Asp Phe Leu Val
                405                 410                 415
Ala Leu Arg Ser Ala Leu Leu Thr Pro Gly Arg Gly Tyr Leu Phe Ala
            420                 425                 430
Gly Cys Gly Leu Val Gly Asp Ser Glu Pro Ala His Glu Tyr Arg Glu
```

435                 440                 445
Thr Cys Leu Lys Leu Ser Ala Met Arg Glu Ala Leu Ser Ala Ile Gly
         450                 455                 460

Gly Leu Asp Glu Val Pro Leu Gln Arg Gly Val Ala
465                 470                 475

<210> SEQ ID NO 4
<211> LENGTH: 1431
<212> TYPE: DNA
<213> ORGANISM: Pseudomonas aeruginosa

<400> SEQUENCE: 4

| | |
|---|---|
| atgagccggc tggcgcccct gagccagtgc ctgcacgcct gcgcggcac cttcgagcgc | 60 |
| gccatcggcc aggcgcaggc gctcgatcgt ccggtgctgg tggcggcatc gttcgagatc | 120 |
| gacccattgg acccgctgca ggtattcggt gcctgggacg accggcaaac gccctgcctg | 180 |
| tactgggaac agcccgagct ggcgttcttc gcctggggct cgccctgga gctgcaaggc | 240 |
| cacggcgaac agcgcttcgc ccggatcgag gaaaactggc aattgctctg cgccgacgcc | 300 |
| gtggtcgagg gcccgctggc gccgcgcctg tgcggcggat ccgcttcga tccgcgcggc | 360 |
| ccgcgcgagg aacactggca agccttcgcc gatgccagcc tgatgctcgc cggcatcacc | 420 |
| gtgctgcgcg agggcgaacg ctaccgggta tctgccaac acctggccaa gcccggcgaa | 480 |
| gatgccctgg ccctggccgc ctaccactgc tcggcgctac tgcgcctgag gcagccggcc | 540 |
| agacgccggc cctcggggcc gaccgctggc gcgcagggcg acgcttcggc gcaggagcgc | 600 |
| aggcaatggg aagccaaggt gagcgacgcg gtaagcagtg tccgccaggg acgcttcggc | 660 |
| aaggtcgtgc tggcccgcac ccaggcccgg cctctcggcg acatcgagcc gtggcaggtc | 720 |
| atcgaacacc tgcgtctgca acatgccgac gcccagctgt tcgcctgtcg ccgcggcaac | 780 |
| gcctgcttcc tcggcgccct cccggaacgc ctggtccgca ttcgcgccgg cgaggcactc | 840 |
| acccatgccc tggccgggac catcgcccgc ggcggcgatg cccaggaaga tgcgcggctc | 900 |
| ggacaggccc tgctggacag cgccaaggac aggcacgaac accagttggt ggtggaggcg | 960 |
| atccgtacgg ccctggaacc cttcagcgag gtgctggaaa tccccgatgc gcccggcctg | 1020 |
| aaacgactgg cgcgagtcca gcacctgaac acgccgatcc gcgcccgcct cgctgacgca | 1080 |
| ggcggcatcc tgcggctgct acaagcgctg catccgaccc ccgcggtggg cggctaccca | 1140 |
| cgcagcgcgg cgctggacta catccgccag cacgaaggga tggaccgcgg ctggtacgcc | 1200 |
| gcgccgctgg gctggctcga cggcgaaggc aacggcgatt tcctggtggc gctgcgctcg | 1260 |
| gccctgctca cgccgggccg gggctacctg ttcgccggct gcggtctggt aggcgattcg | 1320 |
| gaaccggccc acgagtatcg cgaaacctgc cttaagctca gtgccatgcg ggaagctcta | 1380 |
| tccgccatag gcggcctgga cgaagtgccc ttgcagcgcg gcgtcgcctg a | 1431 |

<210> SEQ ID NO 5
<211> LENGTH: 102
<212> TYPE: PRT
<213> ORGANISM: Pseudomonas aeruginosa

<400> SEQUENCE: 5

Met Met Lys Thr Pro Glu Asp Cys Thr Gly Leu Ala Asp Ile Arg Glu
1               5                   10                  15

Ala Ile Asp Arg Ile Asp Leu Asp Ile Val Gln Ala Leu Gly Arg Arg
            20                  25                  30

Met Asp Tyr Val Lys Ala Ala Ser Arg Phe Lys Ala Ser Glu Ala Ala

```
            35                  40                  45
Ile Pro Ala Pro Glu Arg Val Ala Ala Met Leu Pro Glu Arg Ala Arg
 50                  55                  60

Trp Ala Glu Glu Asn Gly Leu Asp Ala Pro Phe Val Glu Gly Leu Phe
 65                  70                  75                  80

Ala Gln Ile Ile His Trp Tyr Ile Ala Glu Gln Ile Lys Tyr Trp Arg
                 85                  90                  95

Gln Thr Arg Gly Ala Ala
            100

<210> SEQ ID NO 6
<211> LENGTH: 309
<212> TYPE: DNA
<213> ORGANISM: Pseudomonas aeruginosa

<400> SEQUENCE: 6
atgatgaaaa ctcccgaaga ctgcaccggc ctggcggaca tccgcgaggc catcgaccgg      60
atcgacctgg atatcgtcca ggccctcggc cgccgcatgg actacgtcaa ggcggcgtcg     120
cgcttcaagg ccagcgaggc ggcgattccg gcgcccgagc gggtcgccgc gatgctcccc     180
gagcgcgccc gctgggccga gaaaacggga ctcgacgcgc ccttcgtcga gggactgttc     240
gcgcagatca tccactggta catcgccgag cagatcaagt actggcgcca gacacggggt     300
gccgcatga                                                             309

<210> SEQ ID NO 7
<211> LENGTH: 350
<212> TYPE: PRT
<213> ORGANISM: Escherichia coli

<400> SEQUENCE: 7

Met Asn Tyr Gln Asn Asp Asp Leu Arg Ile Lys Glu Ile Lys Glu Leu
  1               5                  10                  15

Leu Pro Pro Val Ala Leu Leu Glu Lys Phe Pro Ala Thr Glu Asn Ala
                 20                  25                  30

Ala Asn Thr Val Ala His Ala Arg Lys Ala Ile His Lys Ile Leu Lys
             35                  40                  45

Gly Asn Asp Asp Arg Leu Leu Val Val Ile Gly Pro Cys Ser Ile His
 50                  55                  60

Asp Pro Val Ala Ala Lys Glu Tyr Ala Thr Arg Leu Leu Ala Leu Arg
 65                  70                  75                  80

Glu Glu Leu Lys Asp Glu Leu Glu Ile Val Met Arg Val Tyr Phe Glu
                 85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
            115                 120                 125

Leu Leu Leu Asp Ile Asn Asp Ser Gly Leu Pro Ala Ala Gly Glu Phe
        130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Asp Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
```

```
                195                 200                 205
Phe Leu Ser Val Thr Lys Trp Gly His Ser Ala Ile Val Asn Thr Ser
            210                 215                 220
Gly Asn Gly Asp Cys His Ile Ile Leu Arg Gly Lys Glu Pro Asn
225                 230                 235                 240
Tyr Ser Ala Lys His Val Ala Glu Val Lys Glu Leu Asn Lys Ala
                245                 250                 255
Gly Leu Pro Ala Gln Val Met Ile Asp Phe Ser His Ala Asn Ser Ser
            260                 265                 270
Lys Gln Phe Lys Lys Gln Met Asp Val Cys Ala Asp Val Cys Gln Gln
                275                 280                 285
Ile Ala Gly Gly Glu Lys Ala Ile Ile Gly Val Met Val Glu Ser His
            290                 295                 300
Leu Val Glu Gly Asn Gln Ser Leu Glu Ser Gly Glu Pro Leu Ala Tyr
305                 310                 315                 320
Gly Lys Ser Ile Thr Asp Ala Cys Ile Gly Trp Glu Asp Thr Asp Ala
                325                 330                 335
Leu Leu Arg Gln Leu Ala Asn Ala Val Lys Ala Arg Arg Gly
            340                 345                 350
```

<210> SEQ ID NO 8
<211> LENGTH: 1053
<212> TYPE: DNA
<213> ORGANISM: Escherichia coli

<400> SEQUENCE: 8

```
atgaattatc aaaatgatga tttaagaata aagaaattaa agaattatt  acctcctgta      60
gctttattag aaaatttcc  tgcaactgaa atgcagcaa  atactgtagc acatgcaaga    120
aaagcaatac ataaaatact aaaggtaat  gatgatagat tattagtagt aataggacct    180
tgtagtatac atgatcctgt agcagcaaaa gaatatgcaa ctagacttt  agcattaaga    240
gaagaattaa aagatgaatt agaaatagta atgagagtat atttgaaaa  acctagaact    300
actgtaggat ggaaaggact tataaatgat cctcatatgg ataatagttt tcaaataaat    360
gatggactta gaatagcaag aaaattactt ttagatataa atgatagtgg attacctgca    420
gctggtgaat ttttagatat gataactcct caatatttag cagatttaat gagttgggga    480
gcaattggag caagaactac tgaaagtcaa gtacatagaa agatgcaagt ggacttagt     540
tgtcctgtag gatttaaaaa tggaactgat ggaactataa agtagcaat  agatgcaata    600
aatgcagctg gtgcacctca ttgttttctt agtgtaacaa atggggaca  tagtgcaata    660
gtaaatacta gtggaaatgg tgattgtcat ataatactta gaggtggaaa agaacctaat    720
tattctgcaa acatgtagc  agaagtaaaa gaaggactta taaagctgg  acttcctgca    780
caggtaatga tagattttc tcatgcaaat agtagtaaac aatttaagaa acaaatggat    840
gtatgtcag  atgtatgtca gcaaatagct ggaggtgaaa agcaataat  tggagtaatg    900
gtagaaagtc atttagtaga aggtaatcaa agtttagaaa gtggtgaacc tttagcttat    960
ggaaaaagta taactgatgc atgtatagga tgggaagata ctgatgcact tcttagacaa   1020
cttgcaaatg cagtaaaagc aagaagagga taa                                1053
```

<210> SEQ ID NO 9
<211> LENGTH: 6561
<212> TYPE: DNA
<213> ORGANISM: Artificial sequence
<220> FEATURE:

<223> OTHER INFORMATION: Synthetic nucleic acid

<400> SEQUENCE: 9

```
cctgcaggat aaaaaaattg tagataaatt ttataaaata gttttatcta caatttttttt    60
atcaggaaac agctatgacc gcggccgcag atagtcataa tagttccaga atagttcaat   120
ttagaaatta gactaaactt caaaatgttt gttaaatata taccaaacta gtatagatat   180
tttttaaata ctggacttaa acagtagtaa tttgcctaaa aaattttttc aattttttttt   240
aaaaaatcct tttcaagttg tacattgtta tggtaatatg taattgaaga gttatgtag    300
taatattgta aacgtttctt gattttttta catccatgta gtgcttaaaa aaccaaaata   360
tgtcacatgc aattgtatat ttcaaataac aatatttatt ttctcgttaa attcacaaat   420
aatttattaa taatatcaat aaccaagatt atacttaaat ggatgtttat tttttaacac   480
ttttatagta aatatattta ttttatgtag taaaaaggtt ataattataa ttgtatttat   540
tacaattaat taaaataaaa ataggggtttt aggtaaaatt aagttatttt aagaagtaat   600
tacaataaaa attgaagtta ttgctttaag gagggaatta ttcatatgag tcatcctgca   660
cttactcaac ttagagcatt aagatatttt aaagaaatac ctgcattaga acctcaatta   720
ttagattggt tattacttga agatagtatg actaaaagat ttgaacaaca gggaaaaact   780
gtaagtgtaa ctatgataag agaaggattt gtagaacaaa atgaaatacc tgaagaatta   840
cctttattac ctaaagaaag tagatattgg ttaagagaaa tattactttg tgcagatggt   900
gaaccttggt tagctggaag aactgtagta cctgtaagta ctttaagtgg acctgaactt   960
gcacttcaaa aattaggaaa aactccttta ggaagatatc tttttactag tagtactttta  1020
actagagatt ttatagaaat tggaagagat gcaggattat ggggaagaag aagtagatta  1080
agattaagtg gaaaaccttt attacttact gaattatttc ttcctgcaag tcctctcttat  1140
taagaattcg agctcggtag gaggtcagaa tgaattatca aaatgatgat ttaagaataa  1200
aagaaattaa agaattatta cctcctgtag ctttattaga aaaatttcct gcaactgaaa  1260
atgcagcaaa tactgtagca catgcaagaa aagcaataca taaaatactt aaaggtaatg  1320
atgatagatt attagtagta ataggaccttt gtagtataca tgatcctgta gcagcaaaag  1380
aatatgcaac tagactttta gcattaagag aagaattaaa agatgaatta gaaatagtaa  1440
tgagagtata ttttgaaaaa cctagaacta ctgtaggatg gaaaggactt ataaatgatc  1500
ctcatatgga taatagttttt caaataaatg atggacttag aatagcaaga aaattacttt  1560
tagatataaa tgatagtgga ttacctgcag ctggtgaatt tttagatatg ataactcctc  1620
aatatttagc agatttaatg agttggggag caattggagc aagaactact gaaagtcaag  1680
tacatagaga agatgcaagt ggacttagtt gtcctgtagg atttaaaaat ggaactgatg  1740
gaactataaa agtagcaata gatgcaataa atgcagctgg tgcacctcat tgtttttctta  1800
gtgtaacaaa atggggacat agtgcaatag taaatactag tggaaatggt gattgtcata  1860
taatacttag aggtggaaaa gaacctaatt attctgcaaa acatgtagca gaagtaaaag  1920
aaggacttaa taaagctgga cttcctgcac aggtaatgat agattttttct catgcaaata  1980
gtagtaaaca atttaagaaa caatggatg tatgtcaga tgtatgtcag caaatagctg  2040
gaggtgaaaa agcaataatt ggagtaatgg tagaaagtca tttagtagaa ggtaatcaaa  2100
gtttagaaag tggtgaacct ttagcttatg gaaaaagtat aactgatgca tgtataggat  2160
gggaagatac tgatgcactt cttagacaac ttgcaaatgc agtaaaagca agaagaggat  2220
aactctagag tcgacgtcac gcgtccatgg agatctcgag gcctgcagac atgcaagctt  2280
```

```
ggcactggcc gtcgttttac aacgtcgtga ctgggaaaac cctggcgtta cccaacttaa  2340
tcgccttgca gcacatcccc ctttcgccag ctggcgtaat agcgaagagg cccgcaccga  2400
tcgcccttcc caacagttgc gcagcctgaa tggcgaatgg cgctagcata aaaataagaa  2460
gcctgcattt gcaggcttct tattttatg gcgcgccgcc attatttttt tgaacaattg  2520
acaattcatt tcttattttt tattaagtga tagtcaaaag cataacagt gctgaataga  2580 aagaaattta cagaaaagaa aattatagaa tttagtatga ttaattatac tcatttatga  2640
atgtttaatt gaatacaaaa aaaaatactt gttatgtatt caattacggg ttaaaatata  2700
gacaagttga aaaatttaat aaaaaaataa gtcctcagct cttatatatt aagctaccaa  2760
cttagtatat aagccaaaac ttaaatgtgc taccaacaca tcaagccgtt agagaactct  2820
atctatagca atatttcaaa tgtaccgaca tacaagagaa acattaacta tatatattca  2880
atttatgaga ttatcttaac agatataaat gtaaattgca ataagtaaga tttagaagtt  2940
tatagccttt gtgtattgga agcagtacgc aaaggcttt ttatttgata aaaattagaa  3000
gtatatttat tttttcataa ttaatttatg aaaatgaaag ggggtgagca aagtgacaga  3060
ggaaagcagt atcttatcaa ataacaaggt attagcaata tcattattga ctttagcagt  3120
aaacattatg acttttatag tgcttgtagc taagtagtac gaaaggggga gctttaaaaa  3180
gctccttgga atacagaa ttcataaatt aatttatgaa agaagggcg tatatgaaaa  3240 cttgtaaaaa ttgcaaagag tttattaaag atactgaaat atgcaaaata cattcgttga  3300
tgattcatga taaacagta gcaacctatt gcagtaaata caatgagtca agatgtttac  3360
ataaagggaa agtccaatgt attaattgtt caaagatgaa ccgatatgga tggtgtgcca  3420
taaaaatgag atgttttaca gaggaagaac agaaaaaaga acgtacatgc attaaatatt  3480
atgcaaggag ctttaaaaaa gctcatgtaa agaagagtaa aagaaaaaa taatttattt  3540 attaatttaa tattgagagt gccgacacag tatgcactaa aaaatatatc tgtggtgtag  3600
tgagccgata caaaaggata gtcactcgca ttttcataat acatcttatg ttatgattat  3660
gtgtcggtgg gacttcacga cgaaaaccca caataaaaaa agagttcggg gtagggttaa  3720
gcatagttga ggcaactaaa caatcaagct aggatatgca gtagcagacc gtaaggtcgt  3780
tgtttaggtg tgttgtaata catacgctat taagatgtaa aaatacggat accaatgaag  3840 ggaaagtat aattttttgga tgtagtttgt ttgttcatct atgggcaaac tacgtccaaa  3900
gccgtttcca aatctgctaa aaagtatatc cttctaaaa tcaaagtcaa gtatgaaatc  3960
ataaataaag tttaattttg aagttattat gatattatgt ttttctatta aaataaatta  4020
agtatataga atagtttaat aatagtatat acttaatgtg ataagtgtct gacagtgtca  4080
cagaaaggat gattgttatg gattataagc ggccggccag tgggcaagtt gaaaaattca  4140
caaaaatgtg gtataatatc tttgttcatt agagcgataa acttgaattt gagagggaac  4200
ttagatggta tttgaaaaaa ttgataaaaa tagttggaac agaaaagagt attttgacca  4260
ctactttgca agtgtaccett gtacctacag catgaccgtt aaagtggata tcacacaaat  4320
aaaggaaaag ggaatgaaac tatatcctgc aatgctttat tatattgcaa tgattgtaaa  4380
ccgccattca gagtttagga cggcaatcaa tcaagatggt gaattgggga tatatgatga  4440
gatgatacca agctatacaa tatttcacaa tgatactgaa acattttcca gcctttggac  4500
tgagtgtaag tctgactttta aatcattttt agcagattat gaaagtgata cgcaacggta  4560
tggaaacaat catagaatgg aaggaaagcc aaatgctccg gaaaacattt ttaatgtatc  4620
```

| | |
|---|---:|
| tatgataccg tggtcaacct tcgatggctt aatctgaat ttgcagaaag gatatgatta | 4680 |
| tttgattcct attttacta tggggaaata ttataaagaa gataacaaaa ttatacttcc | 4740 |
| tttggcaatt caagttcatc acgcagtatg tgacggattt cacatttgcc gttttgtaaa | 4800 |
| cgaattgcag gaattgataa atagttaact tcaggtttgt ctgtaactaa aaacaagtat | 4860 |
| ttaagcaaaa acatcgtaga aatacggtgt tttttgttac cctaagttta aactccttt | 4920 |
| tgataatctc atgaccaaaa tcccttaacg tgagttttcg ttccactgag cgtcagaccc | 4980 |
| cgtagaaaag atcaaaggat cttcttgaga tccttttttt ctgcgcgtaa tctgctgctt | 5040 |
| gcaaacaaaa aaaccaccgc taccagcggt ggtttgtttg ccggatcaag agctaccaac | 5100 |
| tcttttccg aaggtaactg gcttcagcag agcgcagata ccaaatactg ttcttctagt | 5160 |
| gtagccgtag ttaggccacc acttcaagaa ctctgtagca ccgcctacat acctcgctct | 5220 |
| gctaatcctg ttaccagtgg ctgctgccag tggcgataag tcgtgtctta ccgggttgga | 5280 |
| ctcaagacga tagttaccgg ataaggcgca gcggtcgggc tgaacggggg gttcgtgcac | 5340 |
| acagcccagc ttggagcgaa cgacctacac cgaactgaga tacctacagc gtgagctatg | 5400 |
| agaaagcgcc acgcttcccg aagggagaaa ggcggacagg tatccggtaa gcggcagggt | 5460 |
| cggaacagga gagcgcacga gggagcttcc agggggaaac gcctggtatc tttatagtcc | 5520 |
| tgtcgggttt cgccacctct gacttgagcg tcgattttg tgatgctcgt caggggggcg | 5580 |
| gagcctatgg aaaaacgcca gcaacgcggc ctttttacgg ttcctggcct tttgctggcc | 5640 |
| ttttgctcac atgttctttc ctgcgttatc ccctgattct gtggataacc gtattaccgc | 5700 |
| ctttgagtga gctgataccg ctcgccgcag ccgaacgacc gagcgcagcg agtcagtgag | 5760 |
| cgaggaagcg gaagagcgcc caatacgcag ggcccctgc ttcggggtca ttatagcgat | 5820 |
| tttttcggta tatccatcct ttttcgcacg atatacagga ttttgccaaa gggttcgtgt | 5880 |
| agactttcct tggtgtatcc aacggcgtca gccgggcagg ataggtgaag taggcccacc | 5940 |
| cgcgagcggg tgttccttct tcactgtccc ttattcgcac ctggcggtgc tcaacgggaa | 6000 |
| tcctgctctg cgaggctggc cggctaccgc cggcgtaaca gatgagggca gcggatggc | 6060 |
| tgatgaaacc aagccaacca ggaagggcag cccacctatc aaggtgtact gccttccaga | 6120 |
| cgaacgaaga gcgattgagg aaaaggcggc ggcggccggc atgagcctgt cggcctacct | 6180 |
| gctggccgtc ggccagggct acaaaatcac gggcgtcgtg gactatgagc acgtccgcga | 6240 |
| gctggcccgc atcaatggcg acctgggccg cctgggcggc ctgctgaaac tctggctcac | 6300 |
| cgacgacccg cgcacggcgc ggttcggtga tgccacgatc ctcgccctgc tggcgaagat | 6360 |
| cgaagagaag caggacgagc ttggcaaggt catgatgggc gtggtccgcc gagggcagga | 6420 |
| gccatgactt ttttagccgc taaaacggcc gggggtgcg cgtgattgcc aagcacgtcc | 6480 |
| ccatgcgctc catcaagaag agcgacttcg cggagctggt gaagtacatc accgacgagc | 6540 |
| aaggcaagac cgatcgggcc c | 6561 |

<210> SEQ ID NO 10
<211> LENGTH: 1137
<212> TYPE: DNA
<213> ORGANISM: Clostridium autoethanogenum

<400> SEQUENCE: 10

| | |
|---|---:|
| ttggaagatt tggagtattt aagagatgag ataaataaaa tagataaaga aatgattgaa | 60 |
| cttttttgaaa agagggcaaa agtatctcgc aaagtagcag aatataaaat ggaaaattct | 120 |
| atggatatac ttgataaatc aagagaagaa gaggtaataa aggttaactt aaaaaatctt | 180 |

```
aaagataagt ctataaaaga tgaaactaaa atcttttttga agaatgttat ggaaataagc    240
aggaacatac aaaaaagaga attcaaacaa tcttctaaaa gtagtgaaat taagcctaaa    300
gggcaaaata gtgatttatt taaaattgga tttcaaggag taccagcatc tttcagtcat    360
gaagcactgt tagagtattt tggaaatgaa tcagaagcat taaactttga aagctttaaa    420
gatgtatttg aagctctaaa aaatggggct ataaagtatg gcgttcttcc tattgaaaat    480
tcctctacag gtggcatccc acaggtttat gatcttatag gagaatatga cttttacata    540
gttggagaaa atgtattga gtaaatcac aatttattag gagtaaaggg agcgtctatt    600
tccgatataa aagaagttta ttctcatagt caagcattta tgcaaagtag taaatttctg    660
gagaaacaca agaattggaa gctaaatccc tattttaata cagctagaag tgccaaatat    720
ataagtgagc aaaatgttaa gagtaaagct gctatagcaa gtaaaaatgc agcaaaactt    780
tatggacttg atataataga aaaaaatata aattataaca gcaataatta cactagattt    840
ataataatag gaaaaaatat agaaagtgat aaacaacgtg acaagataag tatattgatt    900
actctgccgc atgaaccagg aactctttat aatgttttga agtatttcca tgaaaataac    960
ttgaatatga ctaaaataga gtcaaggcct ataataaata aatcctggca gtacttcttt    1020
tacattgatt ttaatggaaa tattatggat aaagatacta ggtatgcttt aaatggtata    1080
gaagaagaaa gcgcatattt taaacttttg gggaattaca aaggagattg ttttttag    1137

<210> SEQ ID NO 11
<211> LENGTH: 378
<212> TYPE: PRT
<213> ORGANISM: Clostridium autoethanogenum

<400> SEQUENCE: 11

Met Glu Asp Leu Glu Tyr Leu Arg Asp Glu Ile Asn Lys Ile Asp Lys
1               5                   10                  15

Glu Met Ile Glu Leu Phe Glu Lys Arg Ala Lys Val Ser Arg Lys Val
                20                  25                  30

Ala Glu Tyr Lys Met Glu Asn Ser Met Asp Ile Leu Asp Lys Ser Arg
            35                  40                  45

Glu Glu Glu Val Ile Lys Val Asn Leu Lys Asn Leu Lys Asp Lys Ser
        50                  55                  60

Ile Lys Asp Glu Thr Lys Ile Phe Leu Lys Asn Val Met Glu Ile Ser
65                  70                  75                  80

Arg Asn Ile Gln Lys Arg Glu Phe Lys Gln Ser Ser Lys Ser Ser Glu
                85                  90                  95

Ile Lys Pro Lys Gly Gln Asn Ser Asp Leu Phe Lys Ile Gly Phe Gln
            100                 105                 110

Gly Val Pro Ala Ser Phe Ser His Glu Ala Leu Leu Glu Tyr Phe Gly
        115                 120                 125

Asn Glu Ser Glu Ala Leu Asn Phe Glu Ser Phe Lys Asp Val Phe Glu
    130                 135                 140

Ala Leu Lys Asn Gly Ala Ile Lys Tyr Gly Val Leu Pro Ile Glu Asn
145                 150                 155                 160

Ser Ser Thr Gly Gly Ile Pro Gln Val Tyr Asp Leu Ile Gly Glu Tyr
                165                 170                 175

Asp Phe Tyr Ile Val Gly Glu Lys Cys Ile Glu Val Asn His Asn Leu
            180                 185                 190

Leu Gly Val Lys Gly Ala Ser Ile Ser Asp Ile Lys Glu Val Tyr Ser
        195                 200                 205
```

-continued

```
His Ser Gln Ala Phe Met Gln Ser Ser Lys Phe Leu Glu Lys His Lys
    210                 215                 220
Asn Trp Lys Leu Asn Pro Tyr Phe Asn Thr Ala Arg Ser Ala Lys Tyr
225                 230                 235                 240
Ile Ser Glu Gln Asn Val Lys Ser Lys Ala Ala Ile Ala Ser Lys Asn
                245                 250                 255
Ala Ala Lys Leu Tyr Gly Leu Asp Ile Ile Glu Lys Asn Ile Asn Tyr
                260                 265                 270
Asn Ser Asn Asn Tyr Thr Arg Phe Ile Ile Ile Gly Lys Asn Ile Glu
        275                 280                 285
Ser Asp Lys Gln Arg Asp Lys Ile Ser Ile Leu Ile Thr Leu Pro His
    290                 295                 300
Glu Pro Gly Thr Leu Tyr Asn Val Leu Lys Tyr Phe His Glu Asn Asn
305                 310                 315                 320
Leu Asn Met Thr Lys Ile Glu Ser Arg Pro Ile Ile Asn Lys Ser Trp
                325                 330                 335
Gln Tyr Phe Phe Tyr Ile Asp Phe Asn Gly Asn Ile Met Asp Lys Asp
                340                 345                 350
Thr Arg Tyr Ala Leu Asn Gly Ile Glu Glu Glu Ser Ala Tyr Phe Lys
        355                 360                 365
Leu Leu Gly Asn Tyr Lys Gly Asp Cys Phe
    370                 375
```